United States Patent
Oeser et al.

(10) Patent No.: US 12,365,890 B2
(45) Date of Patent: *Jul. 22, 2025

(54) OPTIMIZATION OF YEAST HOST CELLS FOR THE PRODUCTION OF HETEROLOGOUS PROTEINS

(71) Applicant: DANSTAR FERMENT AG, Zug (CH)

(72) Inventors: Michelle Oeser, Croydon, NH (US); Janet Fisher, Ossipee, NH (US); Aaron Argyros, Lebanon, NH (US)

(73) Assignee: DANSTAR FERMENT AG, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/545,514

(22) Filed: Dec. 19, 2023

(65) Prior Publication Data

US 2024/0182882 A1 Jun. 6, 2024

Related U.S. Application Data

(63) Continuation of application No. 17/277,220, filed as application No. PCT/IB2019/057944 on Sep. 19, 2019, now Pat. No. 11,891,641.

(60) Provisional application No. 62/733,471, filed on Sep. 19, 2018.

(51) Int. Cl.
*C12N 15/81* (2006.01)
*C12N 9/00* (2006.01)
*C12N 9/88* (2006.01)

(52) U.S. Cl.
CPC .............. *C12N 9/88* (2013.01); *C12N 9/00* (2013.01); *C12N 15/81* (2013.01)

(58) Field of Classification Search
CPC ............. C12N 15/21; C12N 9/00; C12N 9/88
See application file for complete search history.

(56) References Cited

U.S. PATENT DOCUMENTS

| | | |
|---|---|---|
| 11,891,641 B2 * | 2/2024 | Oeser ................. C12N 9/00 |
| 2005/0239164 A1 | 10/2005 | Perrone et al. |
| 2010/0167363 A1 | 7/2010 | Bramucci et al. |
| 2014/0096439 A1 | 4/2014 | Bramucci et al. |

FOREIGN PATENT DOCUMENTS

WO     WO 2017/158189 A1     9/2017

OTHER PUBLICATIONS

GenBank, "*Saccharomyces cerevisae* strain NCIM3107 chromosome 10 sequence," Accession No. CP009954, Dec. 30, 2014. (101 pages).
Shanmugavel et al., "Probing functional roles of Wilson disease protein (ATP7B) copper-binding domains in yeast," *Metallomics* 9:981-988, 2017.
Ulaganathan et al., "Genome Sequence of *Saccharomyces cerevisae* NCIM3107, Used in Biotethanol Production," *Genome Announcements* 3(1):1-2, Feb. 2015.
Nevoight, "Progress in Metabolic Engineering of *Saccharomyces cerevisiae*," *Microbiology and Molecular Biology Reviews* 72(3):379-412, 2008.

* cited by examiner

*Primary Examiner* — Tekchand Saidha
(74) *Attorney, Agent, or Firm* — Seed IP Law Group LLP

(57) ABSTRACT

The present disclosure concerns yeast host cell especially suited for the expression of heterologous proteins, such as heterologous enzymes. The yeast host cell of the present disclosure exhibits an alteration in the cAMP signaling pathway which allows achieving increased heterologous protein yield and associated biological activity. The yeast host cell can also exhibit polyploidy.

21 Claims, 17 Drawing Sheets

Specification includes a Sequence Listing.

```
S288C   ATGTCATCAAAACCTGATACTGGTTCGGAAATTTCTGGCCCTCAGCGACAGGAAGAACAA  60
M18151  ATGTCATCAAAACCTGATACTGGTTCGGAAATTTCTGGCCCTCAGCGACAGGAAGAACAA  60
M18152  ATGTCATCAAAACCTGATACTGGTTCGGAAATTTCTGGCCCTCAGCGACAGGAAGAACAA  60
        ************************************************************

S288C   GAACAACAGATAGAGCAGAGCTCACCTACGGAAGCAAACGATAGAAGCATTCATGATGAG  120
M18151  GAACAACAGATAGAGCAGAGCTCACCTACGGAAGCAAACGATAGAAGCATTCATGATGAG  120
M18152  GAACAACAGATAGAGCAGAGCTCGCCTACGGAAGCAAACGATAGAAGCATTCATGATGAG  120
        *********************** ************************************

S288C   GTACCAAAAGTCAAGAAGCGTCACGAACAAAATAGTGGTCACAAATCAAGAAGGAATAGC  180
M18151  GTACCAAAAGTCAAGAAGCGTCACGAACAAAATAGTGGTCACAAATCAAGAAGGAATAGC  180
M18152  GTACCAAAAGTCAAGAAGCGTCACGAACAAAATAGTGGTCACAAATCAAGAAGGAATAGC  180
        ************************************************************

S288C   GCATATAGTTATTACAGCCCACGGTCGCTTTCTATGACCAAAAGCAGGGAGAGTATCACT  240
M18151  GCATATAGTTATTACAGCCCACGGTCGCTTTCTATGACCAAAAGCAGGGAGAGTATCACT  240
M18152  GCATATAGTTATTACAGCCCACGGTCGCTTTCTATGACCAAAAGCAGGGAGAGTATCACT  240
        ************************************************************

S288C   CCAAATGGTATGGATGATGTAAGTATTTCGAACGTGGAACATCCAAGGCCGACAGAACCG  300
M18151  CCAAATGGTATGGATGATGTAAGTATTTCGAACGTGGAACATCCAAGGCCGACAGAACCG  300
M18152  CCAAATGGTATGGATGATGTAAGTATTTCGAACGTGGAACATCCAAGGCCGACAGAACCG  300
        ************************************************************

S288C   AAAATCAAAAGGGGTCCATATTTACTGAAGAAAACATTGAGCAGTCTTTCAATGACGAGC  360
M18151  AAAATCAAAAGGGGTCCATATTTACTGAAGAAAACATTGAGCAGTCTTTCAATGACGAGC  360
M18152  AAAATCAAAAGGGGTCCATATTTACTGAAGAAAACATTGAGCAGTCTTTCAATGACGAGC  360
        ************************************************************

S288C   GCGAATAGTACTCATGATGATAATAAAGACCACGGTTACGCTTTGAATTCATCCAAGACG  420
M18151  GCGAATAGTACTCATGATGATAATAAAGACCACGGTTACGCTTTGAATTCATCCAAGACG  420
M18152  GCGAATAGTACTCATGATGATAATAAAGACCACGGTTACGCTTTGAATTCATCCAAGACG  420
        ************************************************************

S288C   CACAACTACACATCTACTCATAACCATCATGACGGTCATCATGATCATCATCATGTTCAG  480
M18151  CACAACTACACATCTACTCATAACCATCATGACGGTCATCATGATCATCATCATGTTCAG  480
M18152  CACAACTACACATCTACTCATAACCATCATGACGGTCATCATGATCATCATCATGTTCAG  480
        ************************************************************

S288C   TTTTTTCCCAATAGGAAGCCATCATTAGCGGAAACCCTATTCAAAAGGTTTTCAGGGTCA  540
M18151  TTTTTTCCCAATAGGAAGCCATCATTAGCGGAAACCCTATTCAAAAGGTTTTCAGGGTCA  540
M18152  TTTTTTCCCAATAGGAAGCCATCATTAGCGGAAACCCTATTCAAAAGGTTTTCAGGGTCA  540
        ************************************************************

S288C   AACAGTCACGATGGCAATAAGTCAGGAAAGGAAAGTAAAGTTGCTAACCTTTCCCTTTCA  600
M18151  AACAGTCACGATGGCAATAAGTCAGGAAAGGAAAGTAAAGTTGCTAACCTTTCCCTTTCA  600
M18152  AACAGTCACGATGGCAATAAGTCAGGAAAGGAAAGTAAAGTTGCTAACCTTTCCCTTTCA  600
        ************************************************************

S288C   ACGGTAAATCCTGCACCTGCTAATAGGAAACCTTCTAAAGACTCCACTTTATCTAATCAC  660
M18151  ACGGTAAATCCTGCACCTGCTAATAGGAAACCTTCTAAAGACTCCACTTTATCTAATCAC  660
M18152  ACGGTAAATCCTGCACCTGCTAATAGGAAACCTTCTAAAGACTCCACTTTATCTAATCAC  660
        ************************************************************

S288C   TTGGCTGATAACGTGCCAAGCACTTTACGAAGGAAAGTGTCCTCATTGGTACGTGGTTCT  720
M18151  TTGGCTGATAACGTGCCAAGCACTTTACGAAGGAAAGTGTCCTCATTGGTACGTGGTTCT  720
M18152  TTGGCTGATAACGTGCCAAGCACTTTACGAAGGAAAGTGTCCTCATTGGTACGTGGTTCT  720
        ************************************************************
```

FIG. 6A

```
S288C   TCCGTCCATGATATAAATAATGGTATTGCAGATAAACAGATTAGACCAAAGCTGTTGCG  780
M18151  TCCGTCCATGATATAAATAATGGTATTGCAGATAAACAGATTAGACCAAAGCTGTTGCG  780
M18152  TCCGTCCATGATATAAATAATGGTATTGCAGATAAACAGATTAGACCAAAGCTGTTGCG  780
        *********************************************** *******

S288C   CAATCAGAAAATACATTACATTCATCCGATGTTCCCAATAGCAAACGCTCGCACAGAAAA  840
M18151  CAATCAGAAAATACATTACATTCATCCGATGTTCCCAATAGCAAACGCTCGCACAGAAAA  840
M18152  CAATCAGAAAATACATTACATTCATCCGATGTTCCCAATAGCAAACGCTCGCACAGAAAA  840
        ************************************************************

S288C   AGCTTTCTGCTAGGCTCCACATCTTCTTCAAGCAGTAGAAGAGGTTCAAATGTCAGTTCA  900
M18151  AGCTTTCTGCTAGGCTCCACATCTTCTTCAAGCAGTAGAAGAGGTTCAAATGTCAGTTCA  900
M18152  AGCTTTCTGCTAGGCTCCACATCTTCTTCAAGCAGTAGAAGAGGTTCAAATGTCAGTTCA  900
        ************************************************************

S288C   ATGACTAACAGTGACAGTGCAAGTATGGCGACGTCGGGTAGTCATGTTCTCCAACATAAC  960
M18151  ATGACTAACAGTGACAGTGCAAGTATGGCGACGTCGGGTAGTCATGTTCTCCAACATAAC  960
M18152  ATGACTAACAGTGACAGTGCAAGTATGGCGACGTCGGGTAGTCATGTTCTCCAACATAAC  960
        ************************************************************

S288C   GTATCTAATGTTTCTCCAACTACTAAAAGTAAGGACAGCGTTAACAGCGAATCCGCCGAT  1020
M18151  GTATCTAATGTTTCTCCAACTACTAAAAGTAAGGACAGCGTTAACAGCGAATCCGCCGAT  1020
M18152  GTATCTAATGTTTCTCCAACTACTAAAAGTAAGGACAGCGTTAACAGCGAATCCGCCGAT  1020
        ************************************************************

S288C   CACACTAATAATAAATCCGAGAAAGTGACTCCAGAATATAATGAGAACATTCCGGAAAAT  1080
M18151  CACACTAATAATAAATCCGAGAAAGTGACTCCAGAATATAATGAGAACATTCCGGAAAAT  1080
M18152  CACACTAATAATAAATCCGAGAAAGTGACTCCAGAATATAATGAGAACATTCCGGAAAAT  1080
        ************************************************************

S288C   TCTAACTCTGACAACAAACGCGAAGCCACAACGCCTACTATAGAAACACCCATTTCATGT  1140
M18151  TCTAACTCTGACAACAAACGCGAAGCCACAACGCCTACTATAGAAACACCCATTTCATGT  1140
M18152  TCTAACTCTGACAACAAACGCGAAGCCACAACGCCTACTATAGAAACACCCATTTCATGT  1140
        ************************************************************

S288C   AAACCATCCCTTTTCAGGCTAGATACAAACCTTGAGGATGTTACTGATATTACAAAGACG  1200
M18151  AAACCATCCCTTTTCAGGCTAGATACAAACCTTGAGGATGTTACTGATATTACAAAGACG  1200
M18152  AAACCATCCCTTTTCAGGCTAGATACAAACCTTGAGGATGTTACTGATATTACAAAGACG  1200
        ************************************************************

S288C   GTGCCACCCACCGCTGTCAATTCTACACTAAATTCTACACACGGGACTGAGACTGCCTCA  1260
M18151  GTGCCACCCACCGCTGTCAATTCTACACTAAATTCTACACACGGGACTGAGACTGCCTCA  1260
M18152  GTGCCACCCACCGCTGTCAATTCTACACTAAATTCTACACACGGGACTGAGACTGCCTCA  1260
        ************************************************************

S288C   CCCAAAACGGTGATCATGCCTGAAGGTCCTAGGAAGTCGGTGTCAATGGCTGATCTCTCC  1320
M18151  CCCAAAACGGTGATCATGCCTGAAGGTCCTAGGAAGTCGGTGTCAATGGCTGATCTCTCC  1320
M18152  CCCAAAACGGTGATCATGCCTGAAGGTCCTAGGAAGTCGGTGTCAATGGCTGATCTCTCC  1320
        ************************************************************

S288C   GTCGCTGCCGCAGCACCTAATGGTGAATTCACATCAACTTCCAATGATAGATCACAATGG  1380
M18151  GTCGCTGCCGCAGCACCTAATGGTGAATTCACATCAACTTCCAATGATAGATCACAATGG  1380
M18152  GTCGCTGCCGCAGCACCTAATGGTGAATTCACATCAACTTCCAATGATAGATCACAATGG  1380
        ************************************************************

S288C   GTAGCACCTCAAAGCTGGGATGTGGAAACCAAAAGGAAAAAAACAAAACCTAAAGGGAGA  1440
M18151  GTAGCACCTCAAAGCTGGGATGTGGAAACCAAAAGGAAAAAAACAAAACCTAAAGGGAGA  1440
M18152  GTAGCACCTCAAAGCTGGGATGTGGAAACCAAAAGGAAAAAAACAAAACCTAAAGGGAGA  1440
        ************************************************************
```

FIG. 6A (cont.)

```
S288C   TCGAAATCAAGAAGGTCAAGTATAGATGCTGATGAACTTGATCCCATGTCACCGGGGCCA 1500
M18151  TCGAAATCAAGAAGGTCAAGTATAGATGCTGATGAACTTGATCCCATGTCACCGGGGCCA 1500
M18152  TCGAAATCAAGAAGGTCAAGTATAGATGCTGATGAACTTGATCCCATGTCACCGGGGCCA 1500
        ************************************************************

S288C   CCTTCAAAAAAGACTCTC------------------------------GTCATCATCACGATCGA 1536
M18151  CCTTCAAAAAAGACTCTCGTCATCGTAAGAACCGACACTCTCGTCATCATCACGATCGA 1560
M18152  CCTTCAAAAAAGACTCTCGTCATCGTAAGAACCGACACTCTCGTCATCATCACGATCGA 1560
        ******************                            ******************

S288C   AAGGATAACGAATCAATGGTCACTGCGGGTGACAGTAACTCAAGTTTTGTTGATATATGT 1596
M18151  AAGGATAACGAATCAATGGTCACTGCGGGTGACAGTAACTCAAGTTTTGTTGATATATGT 1620
M18152  AAGGATAACGAATCAATGGTCACTGCGGGTGACAGTAACTCAAGTTTTGTTGATATATGT 1620
        ************************************************************

S288C   AAAGAAAACGTTCCGAATGATAGCAAGACCGCACTCGATACTAAATCTGTGAACCGCTTA 1656
M18151  AAAGAAAACGTTCCGAATGATAGCAAGACCGCACTCGATACTAAATCTGTGAACCGCTTA 1680
M18152  AAAGAAAACGTTCCGAATGATAGCAAGACCGCACTCGATACTAAATCTGTGAACCGCTTA 1680
        ************************************************************

S288C   AAAAGTAATTTGGCTATGAGTCCCCAAGTATACGATATGCTCCATCAAATTTAGATGGG 1716
M18151  AAAAGTAATTTGGCTATGAGTCCCCAAGTATACGATATGCTCCATCAAATTTAGATGGG 1740
M18152  AAAAGTAATTTGGCTATGAGTCCCCAAGTATACGATATGCTCCATCAAATTTAGATGGG 1740
        ************************************************************

S288C   GACTACGACACGTCTTCCACTTCCTCATCTTTACCGTCCTCATCTATTAGTTCAGAAGAT 1776
M18151  GACTACGACACGTCTTCCACTTCCTCATCTTTACCGTCCTCATCTATTAGTTCAGAAGAT 1800
M18152  GACTACGACACGTCTTCCACTTCCTCATCTTTACCGTCCTCATCTATTAGTTCAGAAGAT 1800
        ************************************************************

S288C   ACATCTTCCTGCAGCGATTCCTCTTCGTACACTAACGCGTATATGGAGGCCAACCGAGAG 1836
M18151  ACATCTTCCTGCAGCGATTCCTCTTCGTACACTAACGCGTATATGGAGGCCAACCGAGAG 1860
M18152  ACATCTTCCTGCAGCGATTCCTCTTCGTACACTAACGCGTATATGGAGGCCAACCGAGAG 1860
        ************************************************************

S288C   CAGGATAATAAAACACCGATCCTGAATAAAACGAAATCGTATACCAAGAAATTTACATCC 1896
M18151  CAGGATAATAAAACACCGATCCTGAATAAAACGAAATCGTATACCAAGAAATTTACATCC 1920
M18152  CAGGATAATAAAACACCGATCCTGAATAAAACGAAATCGTATACCAAGAAATTTACATCC 1920
        ************************************************************

S288C   TCTTCGGTAAATATGAATTCACCAGATGGTGCCCAGAGTTCTGGATTATTACTACAAGAT 1956
M18151  TCTTCGGTAAATATGAATTCACCAGATGGTGCCCAGAGTTCTGGATTATTACTACAAGAT 1980
M18152  TCTTCGGTAAATATGAATTCACCAGATGGTGCCCAGAGTTCTGGATTATTACTACAAGAT 1980
        ************************************************************

S288C   GAGAAGGACGATGAGGTCGAGTGCCAACTGGAACATTACTATAAAGATTTCAGTGATTTA 2016
M18151  GAGAAGGACGATGAGGTCGAGTGCCAACTGGAACATTACTATAAAGATTTCAGTGATTTA 2040
M18152  GAGAAGGACGATGAGGTCGAGTGCCAACTGGAACATTACTATAAAGATTTCAGTGATTTA 2040
        ************************************************************

S288C   GATCCAAAGAGGCACTATGCTATTCGTATATTCAATACTGATGACACTTTTACGACTCTC 2076
M18151  GATCCAAAGAGGCACTATGCTATTCGTATATTCAATACTGATGACACTTTTACGACTCTC 2100
M18152  GATCCAAAGAGGCACTATGCTATTCGTATATTCAATACTGATGACACTTTTACGACTCTC 2100
        ************************************************************

S288C   TCATGTACTCCAGCGACTACCGTCGAAGAGATAATACCTGCACTTAAAAGAAAATTTAAC 2136
M18151  TCATGTACTCCAGCGACTACCGTCGAAGAGATAATACCTGCACTTAAAAGAAAATTTAAC 2160
M18152  TCATGTACTCCAGCGACTACCGTCGAAGAGATAATACCTGCACTTAAAAGAAAATTTAAC 2160
        ************************************************************
```

FIG. 6A (cont.)

```
S288C   ATTACAGCGCAAGGGAATTTTCAAATTTCCCTGAAGGTGGGAAAGTTGTCAAAAATTTTG  2196
M18151  ATTACAGCGCAAGGGAATTTTCAAATTTCCCTGAAGGTGGGAAAGTTGTCAAAAATTTTG  2220
M18152  ATTACAGCGCAAGGGAATTTTCAAATTTCCCTGAAGGTGGGAAAGTTGTCAAAAATTTTG  2220
        ************************************************************

S288C   AGACCAACTTCGAAACCTATTTTAATTGAAAGAAAACTTTTACTTTTGAATGGTTATCGA  2256
M18151  AGACCAACTTCGAAACCTATTTTAATTGAAAGAAAACTTTTACTTTTGAATGGTTATCGA  2280
M18152  AGACCAACTTCGAAACCTATTTTAATTGAAAGAAAACTTTTACTTTTGAATGGTTATCGA  2280
        ************************************************************

S288C   AAGTCAGACCCACTTCATATTATGGGTATAGAGGATTTAAGTTTTGTTTTTAAGTTTCTT  2316
M18151  AAGTCAGACCCACTTCATATTATGGGTATAGAGGATTTAAGTTTTGTTTTTAAGTTTCTT  2340
M18152  AAGTCAGACCCACTTCATATTATGGGTATAGAGGATTTAAGTTTTGTTTTTAAGTTTCTT  2340
        ************************************************************

S288C   TTCCATCCTGTCACACCTTCTCACTTTACTCCTGAACAAGAACAAAGAATAATGAGAAGC  2376
M18151  TTCCATCCTGTCACACCTTCTCACTTTACTCCTGAACAAGAACAAAGAATAATGAGAAGC  2400
M18152  TTCCATCCTGTCACACCTTCTCACTTTACTCCTGAACAAGAACAAAGAATAATGAGAAGC  2400
        ************************************************************

S288C   GAATTTGTTCACGTAGATTTAAGGAATATGGATCTGACTACACCTCCCATCATTTTTTAC  2436
M18151  GAATTTGTTCACGTAGATTTAAGGAATATGGATCTGACTACACCTCCCATCATTTTTTAC  2460
M18152  GAATTTGTTCACGTAGATTTAAGGAATATGGATCTGACTACACCTCCCATCATTTTTTAC  2460
        ************************************************************
                                                    ↓
S288C   CAGCATACGTCAGAAATAGAAAGTTTAGACGTTTCTAATAACGCAAATATATTCCTACCT  2496
M18151  CAGCATACGTCAGAAATAGAAAGTTTAGACGTTTCTAATAACGTAAATATATTCCTACCT  2520
M18152  CAGCATACGTCAGAAATAGAAAGTTTAGACGTTTCTAATAACGCAAATATATTCCTACCT  2520
        *******************************************  ***************

S288C   CTGGAGTTCATTGAAAGCTCGATTAAATTATTAAGTTTGAGAATGGTTAATATTAGAGCA  2556
M18151  CTGGAGTTCATTGAAAGCTCGATTAAATTATTAAGTTTGAGAATGGTTAATATTAGAGCA  2580
M18152  CTGGAGTTCATTGAAAGCTCGATTAAATTATTAAGTTTGAGAATGGTTAATATTAGAGCA  2580
        ************************************************************
                               ↓
S288C   TCTAAATTCCTTCCAATATCACTAAGGCGTATAAACTAGTATCTTTGGAATTACAGAGA  2616
M18151  TCTAAATTCCTTCCAATATCACTAAGGCGTATAAACTAGTATCTTTGGAATTACAGAGA  2640
M18152  TCTAAATTCCTTCCAATATCACTGAGGCGTATAAACTAGTATCTTTGGAATTACAGAGA  2640
        ***********************  ***********************************

S288C   AACTTCATAAGAAAAGTACCGAACTCAATCATGAAACTGAGTAATTTAACGATATTAAAC  2676
M18151  AACTTCATAAGAAAAGTACCGAACTCAATCATGAAACTGAGTAATTTAACGATATTAAAC  2700
M18152  AACTTCATAAGAAAAGTACCGAACTCAATCATGAAACTGAGTAATTTAACGATATTAAAC  2700
        ************************************************************

S288C   CTTCAATGTAATGAGCTTGAAAGCCTACCGGCTGGATTTGTTGAACTGAAAAATCTGCAA  2736
M18151  CTTCAATGTAATGAGCTTGAAAGCCTACCGGCTGGATTTGTTGAACTGAAAAATCTGCAA  2760
M18152  CTTCAATGTAATGAGCTTGAAAGCCTACCGGCTGGATTTGTTGAACTGAAAAATCTGCAA  2760
        ************************************************************

S288C   TTGCTAGACTTGTCTTCAAACAAGTTCATGCACTACCCAGAAGTTATTAACTACTGCACC  2796
M18151  TTGCTAGACTTGTCTTCAAACAAGTTCATGCACTACCCAGAAGTTATTAACTACTGCACC  2820
M18152  TTGCTAGACTTGTCTTCAAACAAGTTCATGCACTACCCAGAAGTTATTAACTACTGCACC  2820
        ************************************************************

S288C   AATCTTTTACAAATAGACCTATCATATAATAAAATCCAAAGCTTACCACAGTCCACTAAG  2856
M18151  AATCTTTTACAAATAGACCTATCATATAATAAAATCCAAAGCTTACCACAGTCCACTAAG  2880
M18152  AATCTTTTACAAATAGACCTATCATATAATAAAATCCAAAGCTTACCACAGTCCACTAAG  2880
        ************************************************************
```

FIG. 6A (cont.)

```
S288C   TACCTAGTAAAGCTTGCGAAGATGAACCTTTCTCATAACAAACTAAATTTTATAGGCGAC  2916
M18151  TACCTAGTAAAGCTTGCGAAGATGAACCTTTCTCATAACAAACTAAATTTTATAGGCGAC  2940
M18152  TACCTAGTAAAGCTTGCGAAGATGAACCTTTCTCATAACAAACTAAATTTTATAGGCGAC  2940
        ************************************************************

S288C   TTATCGGAAATGACAGATTTGAGGACGCTGAACCTAAGATATAACAGAATATCATCAATT  2976
M18151  TTATCGGAAATGACAAATTTGAGGACGCTGAACCTAAGATATAACAGAATATCATCAATT  3000
M18152  TTATCGGAAATGACAAATTTGAGGACGCTGAACCTAAGATATAACAGAATATCATCAATT  3000
        *************** ********************************************

S288C   AAGACAAATGCGTCTAACTTGCAGAACCTTTTTTTAACAGATAATAGAATTTCGAACTTT  3036
M18151  AAGACAAATGCGTCTAACTTGCAGAACCTTTTTTTAACAGATAATAGAATTTCGAACTTT  3060
M18152  AAGACAAATGCGTCTAACTTGCAGAACCTTTTTTTAACAGATAATAGAATTTCGAACTTT  3060
        ************************************************************

S288C   GAAGACACTTTGCCGAAACTAAGAGCCCTTGAAATTCAAGAGAATCCAATCACTTCTATA  3096
M18151  GAAGACACTTTGCCGAAACTAAGAGCCCTTGAAATTCAAGAGAATCCAATCACTTCTATA  3120
M18152  GAAGACACTTTGCCGAAACTAAGAGCCCTTGAAATTCAAGAGAATCCAATCACTTCTATA  3120
        ************************************************************

S288C   TCCTTCAAAGATTTTTATCCAAAAAACATGACAAGTTTGACGTTGAACAAGGCACAGTTA  3156
M18151  TCCTTCAAAGATTTTTATCCAAAAAACATGACAAGTTTGACGTTGAACAAGGCACAGTTA  3180
M18152  TCCTTCAAAGATTTTTATCCAAAAAACATGACAAGTTTGACGTTGAACAAGGCACAGTTA  3180
        ************************************************************

S288C   TCGAGTATTCCTGGAGAATTACTCACCAAACTATCTTTCCTCGAGAAACTTGAACTTAAT  3216
M18151  TCGAGTATTCCTGGAGAATTACTCACCAAACTATCTTTCCTCGAGAAACTTGAACTTAAT  3240
M18152  TCGAGTATTCCTGGAGAATTACTCACCAAACTATCTTTCCTCGAGAAACTTGAACTTAAT  3240
        ************************************************************

S288C   CAGAATAATTTGACTAGACTGCCACAGGAGATATCCAAGTTGACTAAATTAGTTTTCCTT  3276
M18151  CAGAATAATTTGACTAGACTGCCACAGGAGATATCCAAGTTGACTAAATTAGTTTTCCTT  3300
M18152  CAGAATAATTTGACTAGACTGCCACAGGAGATATCCAAGTTGACTAAATTAGTTTTCCTT  3300
        ************************************************************

S288C   TCAGTGGCGAGAAACAAACTAGAGTATATTCCACCCGAGCTATCTCAACTGAAAAGTTTG  3336
M18151  TCAGTGGCGAGAAACAAACTAGAGTATATTCCACCCGAGCTATCTCAACTGAAAAGTTTG  3360
M18152  TCAGTGGCGAGAAACAAACTAGAGTATATTCCACCCGAGCTATCTCAACTGAAAAGTTTG  3360
        ************************************************************

S288C   AGGACATTAGATCTACATTCTAACAACATAAGGGACTTTGTTGACGGTATGGAAAACCTT  3396
M18151  AGGACATTAGATCTACATTCTAACAACATAAGGGACTTTGTTGACGGTATGGAAAACCTT  3420
M18152  AGGACATTAGATCTACATTCTAACAACATAAGGGACTTTGTTGACGGTATGGAAAACCTT  3420
        ************************************************************

S288C   GAACTAACATCGCTAAATATTTCATCGAATGCATTCGGTAACTCTAGCTTAGAAAATTCT  3456
M18151  GAACTAACATCGCTAAATATTTCATCGAATGCATTCGGTAACTCTAGCTTAGAAAATTCT  3480
M18152  GAACTAACATCGCTAAATATTTCATCGAATGCATTCGGTAACTCTAGCTTAGAAAATTCT  3480
        ************************************************************

S288C   TTTTACCATAACATGTCATATGGGTCAAAGTTATCTAAAAGCCTGATGTTTTTTATTGCT  3516
M18151  TTTTACCATAACATGTCATATGGGTCAAAGTTATCTAAAAGCCTGATGTTTTTTATTGCT  3540
M18152  TTTTACCATAACATGTCATATGGGTCAAAGTTATCTAAAAGCCTGATGTTTTTTATTGCT  3540
        ************************************************************

S288C   GCAGACAATCAATTTGATGATGCTATGTGGCCTCTTTTCAATTGCTTTGTCAATCTGAAA  3576
M18151  GCAGACAATCAATTTGATGATGCTATGTGGCCTCTTTTCAATTGCTTTGTCAATCTGAAA  3600
M18152  GCAGACAATCAATTTGATGATGCTATGTGGCCTCTTTTCAATTGCTTTGTCAATCTGAAA  3600
        ************************************************************
```

FIG. 6A (cont.)

```
S288C   GTGCTAAATCTTTCTTACAACAATTTTTCAGATGTATCGCACATGAAACTTGAGAGCATT   3636
M18151  GTGCTAAATCTTTCTTACAACAATTTTTCAGATGTATCGCACATGAAACTTGAGAGCATT   3660
M18152  GTGCTAAATCTTTCTTACAACAATTTTTCAGATGTATCGCACATGAAACTTGAGAGCATT   3660
        ************************************************************

S288C   ACCGAATTGTACCTCTCCGGTAATAAGCTCACGACATTGTCGGGTGATACAGTTTTGAAA   3696
M18151  ACCGAATTGTACCTCTCCGGTAATAAGCTCACGACATTGTCGGGTGATACAGTTTTGAAA   3720
M18152  ACCGAATTGTACCTCTCCGGTAATAAGCTCACGACATTGTCGGGTGATACAGTTTTGAAA   3720
        ************************************************************

S288C   TGGAGCTCTTTAAAGACTTTAATGTTGAATAGTAACCAAATGTTATCTCTGCCTGCAGAA   3756
M18151  TGGAGCTCTTTAAAGACTTTAATGTTGAATAGTAACCAAATGTTATCTCTGCCTGCAGAA   3780
M18152  TGGAGCTCTTTAAAGACTTTAATGTTGAATAGTAACCAAATGTTATCTCTGCCTGCAGAA   3780
        ************************************************************

S288C   TTATCAAATCTCTCACAGCTAAGTGTATTTGATGTTGGAGCAAATCAATTAAAGTATAAT   3816
M18151  TTATCAAATCTCTCACAGCTAAGTGTATTTGATGTTGGAGCAAATCAATTAAAGTATAAT   3840
M18152  TTATCAAATCTCTCACAGCTAAGTGTATTTGATGTTGGAGCAAATCAATTAAAGTATAAT   3840
        ************************************************************

S288C   ATATCAAACTATCATTACGATTGGAACTGGAGGAATAATAAAGAACTAAAATATTTGAAT   3876
M18151  ATATCAAACTATCATTACGATTGGAACTGGAGGAATAATAAAGAACTAAAATATTTGAAT   3900
M18152  ATATCAAACTATCATTACGATTGGAACTGGAGGAATAATAAAGAACTAAAATATTTGAAT   3900
        ************************************************************

S288C   TTTTCAGGAAATCGAAGGTTTGAAATAAAGTCATTTATAAGTCACGATATTGATGCTGAT   3936
M18151  TTTTCAGGAAATCGAAGGTTTGAAATAAAGTCATTTATAAGTCACGATATTGATGCTGAT   3960
M18152  TTTTCAGGAAATCGAAGGTTTGAAATAAAGTCATTTATAAGTCACGATATTGATGCTGAT   3960
        ************************************************************

S288C   TTGTCAGATCTGACAGTATTACCTCAGTTAAAGGTACTAGGTTTAATGGACGTAACTTTA   3996
M18151  TTGTCAGATCTGACAGTATTACCTCAGTTAAAGGTACTAGGTTTAATGGACGTAACTTTA   4020
M18152  TTGTCAGATCTGACAGTATTACCTCAGTTAAAGGTACTAGGTTTAATGGACGTAACTTTA   4020
        ************************************************************

S288C   AATACTACCAAAGTACCGGATGAAAATGTCAATTTCCGTTTAAGGACAACTGCATCAATA   4056
M18151  AATACTACCAAAGTACCGGATGAAAATGTCAATTTCCGTTTAAGGACAACTGCATCAATA   4080
M18152  AATACTACCAAAGTACCGGATGAAAATGTCAATTTCCGTTTAAGGACAACTGCATCAATA   4080
        ************************************************************

S288C   ATAAATGGGATGCGCTACGGTGTTGCTGATACATTAGGTCAAAGAGACTATGTGTCATCT   4116
M18151  ATAAATGGGATGCGCTACGGTGTTGCTGATACATTAGGTCAAAGAGACTATGTGTCATCT   4140
M18152  ATAAATGGGATGCGCTACGGTGTTGCTGATACATTAGGTCAAAGAGACTATGTGTCATCT   4140
        ************************************************************

S288C   CGTGATGTTACCTTTGAAAGATTCCGCGGAAATGACGACGAATGCTTACTATGTCTTCAT   4176
M18151  CGTGATGTTACCTTTGAAAGATTCCGCGGAAATGACGACGAATGCTTACTATGTCTTCAT   4200
M18152  CGTGATGTTACCTTTGAAAGATTCCGCGGAAATGACGACGAATGCTTACTATGTCTTCAT   4200
        ************************************************************

S288C   GATAGTAAAAACCAAAATGCAGATTATGGCCACAATATATCAAGAATTGTTAGAGATATT   4236
M18151  GATAGTAAAAACCAAAATGCAGATTATGGCCACAATATATCAAGAATTGTTAGAGATATT   4260
M18152  GATAGTAAAAACCAAAATGCAGATTATGGCCACAATATATCAAGAATTGTTAGAGATATT   4260
        ************************************************************
                                                   ↓
S288C   TACGATAAAATACTGATCAGACAACTGGAAAGGTATGGAGACGAAACAGATGATAATATA   4296
M18151  TACGATAAAATACTGATCAGACAACTGGAAAGGTATGGAGACGAAACAGATGATAATATA   4320
M18152  TACGATAAAATACTGATCAGACAACTGGAAAGGTATGGAGACGACACAGATGATAATATA   4320
        ******************************************* ****************
```

FIG. 6A (cont.)

```
S288C   AAAACTGCACTTCGTTTCAGTTTTTTGCAACTGAATAAGGAGATTAACGGAATGCTAAAT  4356
M18151  AAAACTGCACTTCGTTTCAGTTTTTTGCAACTGAATAAGGAGATTAACGGAATGCTAAAT  4380
M18152  AAAACTGCACTTCGTTTCAGTTTTTTGCAACTGAATAAGGAGATTAACGGAATGCTAAAT  4380
        ************************************************************

S288C   TCTGTTGATAATGGTGCCGATGTTGCCAATCTTTCATATGCAGACTTGCTAAGTGGCGCT  4416
M18151  TCTGTTGATAATGGTGCCGATGTTGCCAATCTTTCATATGCAGACTTGCTAAGTGGCGCT  4440
M18152  TCTGTTGATAATGGTGCCGATGTTGCCAATCTTTCATATGCAGACTTGCTAAGTGGCGCT  4440
        ************************************************************

S288C   TGCTCTACTGTGATATATATCAGAGGGAAGAAACTCTTCGCTGCAAATTTAGGTGACTGT  4476
M18151  TGCTCTACTGTGATATATATCAGAGGGAAGAAACTCTTCGCTGCAAATTTAGGTGACTGT  4500
M18152  TGCTCTACTGTGATATATATCAGAGGGAAGAAACTCTTCGCTGCAAATTTAGGTGACTGT  4500
        ************************************************************

S288C   ATGGCTATTTTATCCAAAAACAATGGTGACTACCAAACGCTAACCAAACAACATCTCCCA  4536
M18151  ATGGCTATTTTATCCAAAAACAATGGTGACTACCAAACGCTAACCAAACAACATCTCCCA  4560
M18152  ATGGCTATTTTATCCAAAAACAATGGTGACTACCAAACGCTAACCAAACAACATCTCCCA  4560
        ************************************************************

S288C   ACAAAGCGGGAAGAATACGAGAGGATCAGAATATCTGGCGGGTATGTCAACAATGGAAAA  4596
M18151  ACAAAGCGGGAAGAATACGAGAGGATCAGAATATCTGGCGGGTATGTCAACAATGGAAAA  4620
M18152  ACAAAGCGGGAAGAATACGAGAGGATCAGAATATCTGGCGGGTATGTCAACAATGGAAAA  4620
        ************************************************************

S288C   TTAGATGGTGTTGTAGATGTGTCTAGAGCAGTGGGTTTTTTGATTTGCTTCCCCACATT   4656
M18151  TTAGATGGTGTTGTAGATGTGTCTAGAGCAGTGGGTTTTTTGATTTGCTTCCCCACATT   4680
M18152  TTAGATGGTGTTGTAGATGTGTCTAGAGCAGTGGGTTTTTTGATTTGCTTCCCCACATT   4680
        ************************************************************

S288C   CATGCTTCTCCCGACATATCTGTCGTGACATTAACAAAAGCAGACGAGATGCTTATTGTA  4716
M18151  CATGCTTCTCCCGACATATCTGTCGTGACATTAACAAAAGCAGACGAGATGCTTATTGTA  4740
M18152  CATGCTTCTCCCGACATATCTGTCGTGACATTAACAAAAGCAGACGAGATGCTTATTGTA  4740
        ************************************************************

S288C   GCAACGCATAAGTTATGGGAATACATGGACGTGGATACAGTTTGTGATATCGCGCGTGAG  4776
M18151  GCAACGCATAAGTTATGGGAATACATGGACGTGGATACAGTTTGTGATATCGCGCGTGAG  4800
M18152  GCAACGCATAAGTTATGGGAATACATGGACGTGGATACAGTTTGTGATATCGCGCGTGAG  4800
        ************************************************************

S288C   AATAGTACTGATCCACTCCGTGCCGCAGCTGAGTTGAAGGATCATGCCATGGCTTACGGC  4836
M18151  AATAGTACTGATCCACTCCGTGCCGCAGCTGAGTTGAAGGATCATGCCATGGCTTACGGC  4860
M18152  AATAGTACTGATCCACTCCGTGCCGCAGCTGAGTTGAAGGATCATGCCATGGCTTACGGC  4860
        ************************************************************

S288C   TGTACAGAGAATATTACAATTTTGTGCCTTGCTCTTTACGAGAACATTCAGCAACAAAAT  4896
M18151  TGTACAGAGAATATTACAATTTTGTGCCTTGCTCTTTACGAGAACATTCAGCAACAAAAT  4920
M18152  TGTACAGAGAATATTACAATTTTGTGCCTTGCTCTTTACGAGAACATTCAGCAACAAAAT  4920
        ************************************************************

S288C   CGGTTCACTTTAAATAAAAACTCTTTAATGACTAGAAGAAGTACTTTCGAGGATACTACA  4956
M18151  CGGTTCACTTTAAATAAAAACTCTTTAATGACTAGAAGAAGTACTTTCGAGGATACTACA  4980
M18152  CGGTTCACTTTAAATAAAAACTCTTTAATGACTAGAAGAAGTACTTTCGAGGATACTACA  4980
        ************************************************************

S288C   TTAAGAAGACTTCAACCTGAGATTTCTCCGCCAACAGGTAACCTAGCAATGGTCTTCACT  5016
M18151  TTAAGAAGACTTCAACCTGAGATTTCTCCGCCAACAGGTAACCTAGCAATGGTCTTCACT  5040
M18152  TTAAGAAGACTTCAACCTGAGATTTCTCCGCCAACAGGTAACCTAGCAATGGTCTTCACT  5040
        ************************************************************
```

FIG. 6A (cont.)

```
S288C   GATATCAAAAGCTCAACCTTCTTATGGGAGCTATTCCCTAACGCAATGAGGACCGCAATA   5076
M18151  GATATCAAAAGCTCAACCTTCTTATGGGAGCTATTCCCTAACGCAATGAGGACCGCAATA   5100
M18152  GATATCAAAAGCTCAACCTTCTTATGGGAGCTATTCCCTAACGCAATGAGGACCGCAATA   5100
        ************************************************************

S288C   AAAACTCACAATGACATTATGCGTCGTCAACTACGAATTTACGGTGGTTACGAAGTAAAG   5136
M18151  AAAACTCACAATGACATTATGCGTCGTCAACTACGAATTTACGGTGGTTACGAAGTAAAG   5160
M18152  AAAACTCACAATGACATTATGCGTCGTCAACTACGAATTTACGGTGGTTACGAAGTAAAG   5160
        ************************************************************

S288C   ACAGAAGGAGACGCCTTTATGGTGGCATTTCCTACGCCAACTAGTGGTCTGACATGGTGC   5196
M18151  ACAGAAGGAGACGCCTTTATGGTGGCATTTCCTACGCCAACTAGTGGTCTGACATGGTGC   5220
M18152  ACAGAAGGAGACGCCTTTATGGTGGCATTTCCTACGCCAACTAGTGGTCTTACATGGTGC   5220
        ************************************************** *********

S288C   TTAAGTGTTCAATTAAAACTCTTGGATGCACAATGGCCGGAGGAAATTACCTCAGTTCAA   5256
M18151  TTAAGTGTTCAATTAAAACTCTTGGATGCACAATGGCCGGAGGAAATTACCTCAGTTCAA   5280
M18152  TTAAGTGTTCAATTAAAACTCTTGGATGCACAATGGCCGGAGGAAATTACCTCAGTTCAA   5280
        ************************************************************

S288C   GACGGCTGCCAAGTTACGGATAGAAATGGTAACATTATCTATCAAGGCCTATCAGTTAGA   5316
M18151  GACGGCTGCCAAGTTACGGATAGAAATGGTAACATTATCTATCAAGGCCTATCAGTTAGA   5340
M18152  GACGGCTGCCAAGTTACGGATAGAAATGGTAACATTATCTATCAAGGCCTATCAGTTAGA   5340
        ************************************************************

S288C   ATGGGTATTCATTGGGGCTGCCCAGTTCCAGAGCTTGATTTAGTGACTCAAAGAATGGAC   5376
M18151  ATGGGTATTCATTGGGGCTGCCCAGTTCCAGAGCTTGATTTAGTGACTCAAAGAATGGAC   5400
M18152  ATGGGTATTCATTGGGGCTGCCCAGTTCCAGAGCTTGATTTAGTGACTCAAAGAATGGAC   5400
        ************************************************************

S288C   TATTTGGGGCCGATGGTCAATAAGGCAGCAAGGGTCCAGGGCGTCGCTGACGGTGGTCAG   5436
M18151  TATTTGGGGCCGATGGTCAATAAGGCAGCAAGGGTCCAGGGCGTCGCTGACGGTGGTCAG   5460
M18152  TATTTGGGGCCGATGGTCAATAAGGCAGCAAGGGTCCAGGGCGTCGCTGACGGTGGTCAG   5460
        ************************************************************

S288C   ATTGCAATGAGTAGTGATTTTTACTCTGAATTCAACAAGATAATGAAGTATCATGAGCGA   5496
M18151  ATTGCAATGAGTAGTGATTTTTACTCTGAATTCAACAAGATAATGAAGTATCATGAGCGA   5520
M18152  ATTGCAATGAGTAGTGATTTTTACTCTGAATTCAACAAGATAATGAAGTATCATGAACGA   5520
        ******************************************************* ***

S288C   GTAGTGAAGGGCAAGGAATCTCTCAAGGAAGTTTATGGTGAAGAAATTATCGGAGAGGTT   5556
M18151  GTAGTGAAGGGCAAGGAATCTCTCAAGGAAGTTTATGGTGAAGAAATTATCGGAGAGGTT   5580
M18152  GTAGTGAAGGGCAAGGAATCTCTCAAGGAAGTTTATGGTGAAGAAATTATCGGAGAGGTT   5580
        ************************************************************

S288C   CTTGAAAGAGAAATTGCCATGCTGGAAAGTATTGGTTGGGCATTTTTTGACTTTGGCGAG   5616
M18151  CTTGAAAGAGAAATTGCCATGCTGGAAAGTATTGGTTGGGCATTTTTTGACTTTGGCGAG   5640
M18152  CTTGAAAGAGAAATTGCCATGCTGGAAAGTATTGGTTGGGCATTTTTTGACTTTGGCGAG   5640
        ************************************************************

S288C   CATAAGCTAAAGGGACTCGAAACCAAAGAACTCGTTACTATTGCGTATCCTAAGATTCTT   5676
M18151  CATAAGCTAAAGGGACTCGAAACCAAAGAACTCGTTACTATTGCGTATCCTAAGATTCTT   5700
M18152  CATAAGCTAAAGGGACTCGAAACCAAAGAACTCGTTACTATTGCGTATCCTAAGATTCTT   5700
        ************************************************************

S288C   GCTTCCAGACACGAATTTGCATCTGAAGATGAGCAGTCAAAATTAATCAATGAAACGATG   5736
M18151  GCTTCCAGACACGAATTTGCATCTGAAGATGAGCAGTCAAAATTAATCAATGAAACGATG   5760
M18152  GCTTCCAGACACGAATTTGCATCTGAAGATGAGCAGTCAAAATTAATCAATGAAACGATG   5760
        ************************************************************
```

FIG. 6A (cont.)

```
S288C   TTGTTTCGTTTAAGAGTCATTTCAAACAGACTGGAATCTATAATGTCAGCTTTAAGCGGC  5796
M18151  TTGTTTCGTTTAAGAGTCATTTCAAACAGACTGGAATCTATAATGTCAGCTTTAAGCGGC  5820
M18152  TTGTTTCATTTAAGAGTCATTTCAAACAGACTGGAATCTATAATGTCAGCTTTAAGCGGC  5820
        ******* ****************************************************

S288C   GGATTTATTGAACTAGACTCTCGGACGGAGGGAAGTTATATTAAATTTAACCCTAAAGTT  5856
M18151  GGATTTATTGAACTAGACTCTCGGACGGAGGGAAGTTATATTAAATTTAACCCTAAAGTT  5880
M18152  GGATTTATTGAACTAGACTCTCGGACGGAGGGAAGTTATATTAAATTTAACCCTAAAGTT  5880
        ************************************************************

S288C   GAAAATGGTATTATGCAATCGATTTCTGAGAAGGATGCGTTGTTATTTTTTGATCATGTA  5916
M18151  GAAAATGGTATTATGCAATCGATTTCTGAGAAGGATGCGTTGTTATTTTTTGATCATGTA  5940
M18152  GAAAATGGTATTATGCAATCGATTTCTGAGAAGGATGCGTTGTTATTTTTTGATCATGTA  5940
        ************************************************************

S288C   ATTACTAGAATCGAATCCAGTGTGGCATTATTACATTTACGACAACAGAGGTGTTCAGGA  5976
M18151  ATTACTAGAATCGAATCCAGTGTGGCATTATTACATTTACGACAACAGAGGTGTTCAGGA  6000
M18152  ATTACTAGAATCGAATCCAGTGTGGCATTATTACATTTACGACAACAGAGGTGTTCAGGA  6000
        ************************************************************

S288C   CTGGAAATTTGCAGAAACGATAAAACATCTGCTCGAAGCAATATTTTCAATGTTGTTGAC  6036
M18151  CTGGAAATTTGCAGAAACGATAAAACATCTGCTCGAAGCAATATTTTCAATGTTGTTGAC  6060
M18152  CTGGAAATTTGCAGAAACGATAAAACATCTGCTCGAAGCAATATTTTCAATGTTGTTGAC  6060
        ************************************************************

S288C   GAACTTTTACAAATGGTTAAGAACGCAAAGGATTTATCAACTTGA  6081 (SEQ ID NO : 1)
M18151  GAACTTTTACAAATGGTTAAGAACGCAAAGGATTTATCAACTTGA  6105 (SEQ ID NO : 5)
M18152  GAACTTTTACAAATGGTTAAGAACGCAAAGGATTTATCAACTTGA  6105 (SEQ ID NO : 7)
        *********************************************
```

FIG. 6A (cont.)

```
S288C    MSSKPDTGSEISGPQRQEEQEQQIEQSSPTEANDRSIHDEVPKVKKRHEQNSGHKSRRNS    60
M18151   MSSKPDTGSEISGPQRQEEQEQQIEQSSPTEANDRSIHDEVPKVKKRHEQNSGHKSRRNS    60
M18152   MSSKPDTGSEISGPQRQEEQEQQIEQSSPTEANDRSIHDEVPKVKKRHEQNSGHKSRRNS    60
         ************************************************************

S288C    AYSYYSPRSLSMTKSRESITPNGMDDVSISNVEHPRPTEPKIKRGPYLLKKTLSSLSMTS   120
M18151   AYSYYSPRSLSMTKSRESITPNGMDDVSISNVEHPRPTEPKIKRGPYLLKKTLSSLSMTS   120
M18152   AYSYYSPRSLSMTKSRESITPNGMDDVSISNVEHPRPTEPKIKRGPYLLKKTLSSLSMTS   120
         ************************************************************

S288C    ANSTHDDNKDHGYALNSSKTHNYTSTHNHHDGHHDHHHVQFFPNRKPSLAETLFKRFSGS   180
M18151   ANSTHDDNKDHGYALNSSKTHNYTSTHNHHDGHHDHHHVQFFPNRKPSLAETLFKRFSGS   180
M18152   ANSTHDDNKDHGYALNSSKTHNYTSTHNHHDGHHDHHHVQFFPNRKPSLAETLFKRFSGS   180
         ************************************************************

S288C    NSHDGNKSGKESKVANLSLSTVNPAPANRKPSKDSTLSNHLADNVPSTLRRKVSSLVRGS   240
M18151   NSHDGNKSGKESKVANLSLSTVNPAPANRKPSKDSTLSNHLADNVPSTLRRKVSSLVRGS   240
M18152   NSHDGNKSGKESKVANLSLSTVNPAPANRKPSKDSTLSNHLADNVPSTLRRKVSSLVRGS   240
         ************************************************************
                                      ↓
S288C    SVHDINNGIADKQIRPKAVAQSENTLHSSDVPNSKRSHRKSFLLGSTSSSSSRRGSNVSS   300
M18151   SVHDINNGIADKQIRPKTVAQSENTLHSSDVPNSKRSHRKSFLLGSTSSSSSRRGSNVSS   300
M18152   SVHDINNGIADKQIRPKAVAQSENTLHSSDVPNSKRSHPKSFLLGSTSSSSSRRGSNVSS   300
         *****************:*******************:**********************

S288C    MTNSDSASMATSGSHVLQHNVSNVSPTTKSKDSVNSESADHTNNKSEKVTPEYNENIPEN   360
M18151   MTNSDSASMATSGSHVLQHNVSNVSPTTKSKDSVNSESADHTNNKSEKVTPEYNENIPEN   360
M18152   MTNSDSASMATSGSHVLQHNVSNVSPTTKSKDSVNSESADHTNNKSEKVTPEYNENIPEN   360
         ************************************************************

S288C    SNSDNKREATTPTIETPISCKPSLFRLDTNLEDVTDITKTVPPTAVNSTLNSTHGTETAS   420
M18151   SNSDNKREATTPTIETPISCKPSLFRLDTNLEDVTDITKTVPPTAVNSTLNSTHGTETAS   420
M18152   SNSDNKREATTPTIETPISCKPSLFRLDTNLEDVTDITKTVPPTAVNSTLNSTHGTETAS   420
         ************************************************************

S288C    PKTVIMPEGPRKSVSMADLSVAAAAPNGEFTSTSNDRSQWVAPQSWDVETKRKKTKPKGR   480
M18151   PKTVIMPEGPRKSVSMADLSVAAAAPNGEFTSTSNDRSQWVAPQSWDVETKRKKTKPKGR   480
M18152   PKTVIMPEGPRKSVSMADLSVAAAAPNGEFTSTSNDRSQWVAPQSWDVETKRKKTKPKGR   480
         ************************************************************

S288C    SKSRRSSIDADELDPMSPGPPSKKDS--------RHHHDRKDNESMVTAGDSNSSFVDIC   532
M18151   SKSRRSSIDADELDPMSPGPPSKKDSRHRKNRHSRHHHDRKDNESMVTAGDSNSSFVDIC   540
M18152   SKSRRSSIDADELDPMSPGPPSKKDSRHRKNRHSRHHHDRKDNESMVTAGDSNSSFVDIC   540
         *************************        ***************************

S288C    KENVPNDSKTALDTKSVNRLKSNLAMSPPSIRYAPSNLDGDYDTSSTSSSLPSSSISSED   592
M18151   KENVPNDSKTALDTKSVNRLKSNLAMSPPSIRYAPSNLDGDYDTSSTSSSLPSSSISSED   600
M18152   KENVPNDSKTALDTKSVNRLKSNLAMSPPSIRYAPSNLDGDYDTSSTSSSLPSSSISSED   600
         ************************************************************

S288C    TSSCSDSSSYTNAYMEANREQDNKTPILNKTKSYTKKFTSSSVNMNSPDGAQSSGLLLQD   652
M18151   TSSCSDSSSYTNAYMEANREQDNKTPILNKTKSYTKKFTSSSVNMNSPDGAQSSGLLLQD   660
M18152   TSSCSDSSSYTNAYMEANREQDNKTPILNKTKSYTKKFTSSSVNMNSPDGAQSSGLLLQD   660
         ************************************************************

S288C    EKDDEVECQLEHYYKDFSDLDPKRHYAIRIFNTDDTFTTLSCTPATTVEEIIPALKRPKFN   712
M18151   EKDDEVECQLEHYYKDFSDLDPKRHYAIRIFNTDDTFTTLSCTPATTVEEIIPALKRPKFN   720
M18152   EKDDEVECQLEHYYKDFSDLDPKRHYAIRIFNTDDTFTTLSCTPATTVEEIIPALKRPKFN   720
         ************************************************************
```

FIG. 6B

```
S288C   ITAQGNFQISLKVGKLSKILRPTSKPILIERKLLLNGYRKSDPLHIMGIEDLSFVFKFL    772
M18151  ITAQGNFQISLKVGKLSKILRPTSKPILIERKLLLNGYRKSDPLHIMGIEDLSFVFKFL    780
M18152  ITAQGNFQISLKVGKLSKILRPTSKPILIERKLLLNGYRKSDPLHIMGIEDLSFVFKFL    780
        **********************************************************
                                                  ↓
S288C   FHPVTPSHFTPEQEQRIMRSEFVHVDLRNMDLTTPPIIFYQHTSEIESLDVSNNANIFLP   832
M18151  FHPVTPSHFTPEQEQRIMRSEFVHVDLRNMDLTTPPIIFYQHTSEIESLDVSNNVNIFLP   840
M18152  FHPVTPSHFTPEQEQRIMRSEFVHVDLRNMDLTTPPIIFYQHTSEIESLDVSNNANIFLP   840
        ****************************************************.******
                          ↓
S288C   LEFIESSIKLLSLRMVNIRASKFPSNITKAYKLVSLELQRNFIRKVPNSIMKLSNLTILN   892
M18151  LEFIESSIKLLSLRMVNIRASKFPSNITKAYKLVSLELQRNFIRKVPNSIMKLSNLTILN   900
M18152  LEFIESSIKLLSLRMVNIRASKFPSNITEAYKLVSLELQRNFIRKVPNSIMKLSNLTILN   900
        ****************************:*******************************

S288C   LQCNELESLPAGFVELKNLQLLDLSSNKFMHYPEVINYCTNLLQIDLSYNKIQSLPQSTK   952
M18151  LQCNELESLPAGFVELKNLQLLDLSSNKFMHYPEVINYCTNLLQIDLSYNKIQSLPQSTK   960
M18152  LQCNELESLPAGFVELKNLQLLDLSSNKFMHYPEVINYCTNLLQIDLSYNKIQSLPQSTK   960
        ************************************************************

S288C   YLVKLAKMNLSHNKLNFIGDLSEMTDLRTLNLRYNRISSIKTNASNLQNLFLTDNRISNF   1012
M18151  YLVKLAKMNLSHNKLNFIGDLSEMTNLRTLNLRYNRISSIKTNASNLQNLFLTDNRISNF   1020
M18152  YLVKLAKMNLSHNKLNFIGDLSEMTNLRTLNLRYNRISSIKTNASNLQNLFLTDNRISNF   1020
        *************************:**********************************

S288C   EDTLPKLRALEIQENPITSISFKDFYPKNMTSLTLNKAQLSSIPGELLTKLSFLEKLELN   1072
M18151  EDTLPKLRALEIQENPITSISFKDFYPKNMTSLTLNKAQLSSIPGELLTKLSFLEKLELN   1080
M18152  EDTLPKLRALEIQENPITSISFKDFYPKNMTSLTLNKAQLSSIPGELLTKLSFLEKLELN   1080
        ************************************************************

S288C   QNNLTRLPQEISKLTKLVFLSVARNKLEYIPPELSQLKSLRTLDLHSNNIRDFVDGMENL   1132
M18151  QNNLTRLPQEISKLTKLVFLSVARNKLEYIPPELSQLKSLRTLDLHSNNIRDFVDGMENL   1140
M18152  QNNLTRLPQEISKLTKLVFLSVARNKLEYIPPELSQLKSLRTLDLHSNNIRDFVDGMENL   1140
        ************************************************************

S288C   ELTSLNISSNAFGNSSLENSFYHNMSYGSKLSKSLMFFIAADNQFDDAMWPLFNCFVNLK   1192
M18151  ELTSLNISSNAFGNSSLENSFYHNMSYGSKLSKSLMFFIAADNQFDDAMWPLFNCFVNLK   1200
M18152  ELTSLNISSNAFGNSSLENSFYHNMSYGSKLSKSLMFFIAADNQFDDAMWPLFNCFVNLK   1200
        ************************************************************

S288C   VLNLSYNNFSDVSHMKLESITELYLSGNKLTTLSGDTVLKWSSLKTLMLNSNQMLSLPAE   1252
M18151  VLNLSYNNFSDVSHMKLESITELYLSGNKLTTLSGDTVLKWSSLKTLMLNSNQMLSLPAE   1260
M18152  VLNLSYNNFSDVSHMKLESITELYLSGNKLTTLSGDTVLKWSSLKTLMLNSNQMLSLPAE   1260
        ************************************************************

S288C   LSNLSQLSVFDVGANQLKYNISNYHYDWNWRNNKELKYLNFSGNPRFEIKSFISHDIDAD   1312
M18151  LSNLSQLSVFDVGANQLKYNISNYHYDWNWRNNKELKYLNFSGNPRFEIKSFISHDIDAD   1320
M18152  LSNLSQLSVFDVGANQLKYNISNYHYDWNWRNNKELKYLNFSGNPRFEIKSFISHDIDAD   1320
        ************************************************************

S288C   LSDLTVLPQLKVLGLMDVTLNTTKVPDENVNFPLRTTASIINGMRYGVADTLGQRDYVSS   1372
M18151  LSDLTVLPQLKVLGLMDVTLNTTKVPDENVNFPLRTTASIINGMRYGVADTLGQRDYVSS   1380
M18152  LSDLTVLPQLKVLGLMDVTLNTTKVPDENVNFPLRTTASIINGMRYGVADTLGQRDYVSS   1380
        ************************************************************
                                                                ↓
S288C   RDVTFERFRGNDDECLLCLHDSKNQNADYGHNISRIVRDIYDKILIRQLERYGDETDDNI   1432
M18151  RDVTFERFRGNDDECLLCLHDSKNQNADYGHNISRIVRDIYDKILIRQLERYGDETDDNI   1440
M18152  RDVTFERFRGNDDECLLCLHDSKNQNADYGHNISRIVRDIYDKILIRQLERYGDDTDDNI   1440
        *****************************************************:******
```

FIG. 6B (cont.)

```
S288C   KTALRFSFLQLNKEINGMLNSVDNGADVANLSYADLLSGACSTVIYIRGKKLFAANLGDC   1492
M18151  KTALRFSFLQLNKEINGMLNSVDNGADVANLSYADLLSGACSTVIYIRGKKLFAANLGDC   1500
M18152  KTALRFSFLQLNKEINGMLNSVDNGADVANLSYADLLSGACSTVIYIRGKKLFAANLGDC   1500
        ************************************************************

S288C   MAILSKNNGDYQTLTKQHLPTKREEYERIRISGGYVNNGKLDGVVDVSPAVGFFDLLPHI   1552
M18151  MAILSKNNGDYQTLTKQHLPTKREEYERIRISGGYVNNGKLDGVVDVSPAVGFFDLLPHI   1560
M18152  MAILSKNNGDYQTLTKQHLPTKREEYERIRISGGYVNNGKLDGVVDVSRAVGFFDLLPHI   1560
        ************************************************ **********

S288C   HASPDISVVTLTKADEMLIVATHKLWEYMDVDTVCDIARENSTDPLRAAAELKDHAMAYG   1612
M18151  HASPDISVVTLTKADEMLIVATHKLWEYMDVDTVCDIARENSTDPLRAAAELKDHAMAYG   1620
M18152  HASPDISVVTLTKADEMLIVATHKLWEYMDVDTVCDIARENSTDPLRAAAELKDHAMAYG   1620
        ************************************************************

S288C   CTENITILCLALYENIQQNRFTLNKNSLMTRRSTFEDTTLRPLQPEISPPTGNLAMVFT   1672
M18151  CTENITILCLALYENIQQNRFTLNKNSLMTRRSTFEDTTLRPLQPEISPPTGNLAMVFT   1680
M18152  CTENITILCLALYENIQQNRFTLNKNSLMTRRSTFEDTTLRPLQPEISPPTGNLAMVFT   1680
        ***********************************************************

S288C   DIKSSTFLWELFPNAMPTAIKTHNDIMRRQLRIYGGYEVKTEGDAFMVAFPTPTSGLTWC   1732
M18151  DIKSSTFLWELFPNAMPTAIKTHNDIMRRQLRIYGGYEVKTEGDAFMVAFPTPTSGLTWC   1740
M18152  DIKSSTFLWELFPNAMPTAIKTHNDIMRRQLRIYGGYEVKTEGDAFMVAFPTPTSGLTWC   1740
        ************************************************************

S288C   LSVQLKLLDAQWPEEITSVQDGCQVTDPNGNIIYQGLSVRMGIHWGCPVPELDLVTQRMD   1792
M18151  LSVQLKLLDAQWPEEITSVQDGCQVTDPNGNIIYQGLSVRMGIHWGCPVPELDLVTQRMD   1800
M18152  LSVQLKLLDAQWPEEITSVQDGCQVTDPNGNIIYQGLSVRMGIHWGCPVPELDLVTQRMD   1800
        ************************************************************

S288C   YLGPMVNKAAPVQGVADGGQIAMSSDFYSEFNKIMKYHERVVKGKESLREVYGEEIIGEV   1852
M18151  YLGPMVNKAAPVQGVADGGQIAMSSDFYSEFNKIMKYHERVVKGKESLREVYGEEIIGEV   1860
M18152  YLGPMVNKAAPVQGVADGGQIAMSSDFYSEFNKIMKYHERVVKGKESLREVYGEEIIGEV   1860
        ************************************************************

S288C   LEREIAMLESIGWAFFDFGEHKLKGLETKELVTIAYPKILASRHEFASEDEQSKLINETM   1912
M18151  LEREIAMLESIGWAFFDFGEHKLKGLETKELVTIAYPKILASRHEFASEDEQSKLINETM   1920
M18152  LEREIAMLESIGWAFFDFGEHKLKGLETKELVTIAYPKILASRHEFASEDEQSKLINETM   1920
        ************************************************************

S288C   LFRLRVISNRLESIMSALSGGFIELDSRTEGSYIKFNPKVENGIMQSISEKDALLFFDHV   1972
M18151  LFRLRVISNRLESIMSALSGGFIELDSRTEGSYIKFNPKVENGIMQSISEKDALLFFDHV   1980
M18152  LFHLRVISNRLESIMSALSGGFIELDSRTEGSYIKFNPKVENGIMQSISEKDALLFFDHV   1980
        ** *********************************************************

S288C   ITRIESSVALLHLRQQRCSGLEICRNDKTSARSNIFNVVDELLQMVKNAKDLST   2026 (SEQ ID NO:2)
M18151  ITRIESSVALLHLRQQRCSGLEICRNDKTSARSNIFNVVDELLQMVKNAKDLST   2034 (SEQ ID NO:6)
M18152  ITRIESSVALLHLRQQRCSGLEICRNDKTSARSNIFNVVDELLQMVKNAKDLST   2034 (SEQ ID NO:8)
        ******************************************************
```

FIG. 6B (cont.)

SEQUENCE LISTING

```
Sequence total quantity: 8
SEQ ID NO: 1               moltype = DNA   length = 6081
FEATURE                    Location/Qualifiers
source                     1..6081
                           mol_type = other DNA
                           organism = Saccharomyces cerevisiae
SEQUENCE: 1
atgtcatcaa aacctgatac tggttcggaa atttctggcc ctcagcgaca ggaagaacaa   60
gaacaacaga tagagcagag ctcacctacg gaagcaaacg atagaagcat tcatgatgag  120
gtaccaaaag tcaagaagcg tcacgaacaa aatagtggtc acaaatcaag aaggaatagc  180
gcatatagtt attacagccc acggtcgctt tctatgacca aaagcaggga gagtatcact  240
ccaaatggta tggatgatgt aagtatttcg aacgtggaac atccaaggcc gacagaaccg  300
aaaatcaaaa ggggtccata tttactgaag aaaacattga gcagtctttc aatgacgagc  360
gcgaatagta ctcatgatga taataaagac cacggttacg ctttgaattc atccaagacg  420
cacaactaca catctactca taaccatcat gacggtcatc atgatcatca tcatgttcag  480
tttttttccca ataggaagcc atcattagcg gaaaccctat tcaaaaggtt ttcagggtca  540
aacagtcacg atggcaataa gtcaggaaag gaaagtaaag ttgctaacct ttcccttttca  600
acggtaaatc ctgcacctgc taataggaaa ccttctaaag actccacttt atctaatcac  660
ttggctgata acgtgccaag cacttacga aggaaagtgt cctcattggt acgtggttct  720
tccgtccatg catataaataa tggtattgca gataaacaga ttagaccaaa ggctgttgcg  780
caatcagaaa atacattaca ttcatccgat gttcccaata gcaaacgctc gcacagaaaa  840
agctttctgc taggctccac atcttcttca agcagtagaa gaggttcaaa tgtcagttca  900
atgactaaca gtgacagtgc aagtatggcg acgtcgggta gtcatgttct ccaacataac  960
gtatctaatg tttctccaac tactaaaagt aaggacagcg ttaacagcga atccgccgat 1020
cacactaata ataaatccga gaagtgact ccagaatata atgagaacat tccgaaaat 1080
tctaactctg acaacaaacg cgaagccaca acgcctacta tagaaacacc catttcatgt 1140
aaaccatccc ttttcaggct agatacaaac cttgaggatg ttactgatat tacaaagacg 1200
gtgccaccca ccgctgtcaa ttctacacta aattctacac acgggactga gactgcctca 1260
cccaaaacgg tgatcatgcc tgaaggtcct aggaagtcgg tgtcaatggc tgatctctcc 1320
gtcgctgccg cagcacctaa tggtgaattc acatcaactt ccaatgatag atcacaatgg 1380
gtagcacctc aaagctggga tgtggaaacc aaaaggaaaa aaacaaaacc taagggaga 1440
tcgaaatcaa gaaggtcaag tatagatgct gatgaacttg atcccatgtc accggggcca 1500
ccttcaaaaa aagactctcg tcatcatcac gatcgaaagg ataacgaatc aatggtcact 1560
gcgggtgaca gtaactcaag ttttgttgat atatgtaaag aaaacgttcc gaatgatagc 1620
aagaccgcac tcgatactaa atctgtgaac cgcttaaaaa gtaatttggc tatgagtccc 1680
ccaagtatac gatatgctcc atcaaattta gatggggact acgacacgtc ttccacttcc 1740
tcatctttac cgtcctcatc tattagttca gaagatacat cttcctgcag cgattcctct 1800
tcgtacacta acgcgtatat ggaggccaac cgagagcagg ataataaaac accgatcctg 1860
aataaaacga aatcgtatac caagaaattt acatcctctt cggtaaatat gaattcacca 1920
gatggtgccc agagttctgg attattacta caagatgaga aggacgatga ggtcgagtgc 1980
caactggaac attactataa agatttcagt gatttagatc caaagaggca ctatgctatt 2040
cgtatattca atactgatga cacttttacg actctctcat gtactccagc gactaccgtc 2100
gaagagataa tacctgcact taaagaaaaa tttaacatta cagcgcaagg gaattttcaa 2160
atttccctga aggtgggaaa gttgtcaaaa attttgagac caacttcgaa acctatttta 2220
attgaaagaa aacttttact tttgaatggt tatcgaaagt cagacccact tcatatatg 2280
ggtatagagg atttaagttt tgttttaag tttcttttcc atcctgtcac accttctcac 2340
tttactcctg aacaagaaca aagaataatg agaagcgaat tgttcacgt agatttaagg 2400
aatatggatc tgactacacc tcccatcatt ttttaccagc atacgtcaga aatagaaagt 2460
ttagacgttt ctaataacgc aaatatattc ctacctctgg agttcattga agctcgatt 2520
aaattattaa gtttgagaat ggttaatatt agagcatcta aattccttc caatatcact 2580
aaggcgtata aactagtatc tttggaatta cagagaaact tcataagaaa agtaccgaac 2640
tcaatcatga aatcgagtaa tttaacgata ttaaaccttc aatgtaatga gcttaaagc 2700
ctaccggctg gatttgttga actgaaaaat ctgcaattgc tagacttgtc ttcaaacaag 2760
ttcatgcact acccagaagt tattaactac tgcaccaatc ttttacaaat agacctatca 2820
tataataaaa tccaaagctt accacagtcc actaagtacc tagtaaagct tgcgaagatg 2880
aacctttctc ataacaaact aaatttttata ggcgacttat cggaaatgac agatttgagg 2940
acgctgaacc taagatataa cagaatatca tcaattaaga caaatgcgtc taacttgcag 3000
aacctttttt taacagataa tagaatttcg aactttgaag acactttgcc gaaactaaga 3060
gcccttgaaa ttcaagagaa tccatcacct tctatatcct tcaaagattt ttatccaaaa 3120
aacatgacaa gtttgacgtt gaacaaggca cagtatcga gtattcctgg agaattactc 3180
accaaactat cttttcctga gaaacttgaa cttaatcaga ataatttgac tagactgcca 3240
caggagatat ccaagttgac taaattagtt ttccttttcag tggcgagaaa caaactagag 3300
tatattccac ccgagctatc tcaactgaaa agtttgagga cattagatct acattctaac 3360
aacataaggg acttttgttga cggtatgaa aaccttgaac taacatcgct aaatatttca 3420
tcgaatgcat tcggtaactc tagcttagaa aattcttttt accataacat gtcatatggg 3480
tcaaagttat ctaaaagcct gatgtttttt attgctgcag acaatcaatt tgatgatgct 3540
atgtggcctc ttttcaattg cttttgtcaat ctgaaagtgc taaatctttc ttacaacaat 3600
ttttcagatg tatcgcacat gaaacttgag agcattaccg aattgtacct ctccggtaat 3660
aagctcacga cattgtcggg tgatacagtt ttgaaatgga gctcttttaaa gactttaatg 3720
ttgaatagta accaaatgtt atctctgcct gcagaattat caaatctctc acagctaagt 3780
gtatttgatg ttggagcaaa tcaattaaag tataatatat caaactatca ttacgattgg 3840
aactggagga ataataaaga actaaatata ttgaattttt caggaaatcg aaggtttgaa 3900
ataagtcat ttataagtca cgatattgat gctgatttgt ctgactgac agtattacct 3960
cagttaaagg tactaggttt aatggacgta actttaaata ctaccaaagt accggatgaa 4020
aatgtcaatt tccgtttaag gacaactgca tcaataataa atgggatgcg ctacggtgtt 4080
gctgatacat taggtcaaag agactatgtg tcatctcgtg atgttacctt tgaaagattc 4140
cgcggaaatg acgacgaatg cttactatgt cttcatgata gtaaaaacca aaatgcagat 4200
tatggccaca atatatcaag aattgttaga gatatttacg ataaaatact gatcagacaa 4260
```

-continued

```
ctggaaaggt atggagacga aacagatgat aatataaaaa ctgcacttcg tttcagtttt   4320
ttgcaactga ataaggagat taacggaatg ctaaattctg ttgataatgg tgccgatgtt   4380
gccaatcttt catatgcaga cttgctaagt ggcgcttgct ctactgtgat atatatcaga   4440
gggaagaaac tcttcgctgc aaatttaggt gactgtatgg ctattttatc caaaaacaat   4500
ggtgactacc aaacgctaac caaacaacat ctcccaacaa agcggggaaga atacgagagg   4560
atcagaatat ctggcgggta tgtcaacaat ggaaaattag atggtgttgt agatgtgtct   4620
agagcagtgg gttttttttga tttgcttccc cacattcatg cttctcccga catatctgtc   4680
gtgacattaa caaaagcaga cgagatgctt attgtagcaa cgcataagtt atgggaatac   4740
atggacgtgg atacagtttg tgatatcgcg cgtgagaata gtactgatcc actccgtgcc   4800
gcagctgagt tgaaggatca tgccatggct tacggctgta cagagaatat tacaattttg   4860
tgccttgctc tttacgagaa cattcagcaa caaatcggt tcactttaaa taaaaactct   4920
ttaatgacta gaagaagtac tttcgaggat actacattaa gaagacttca acctgagatt   4980
tctccgccaa caggtaacct agcaatggtc ttcactgata tcaaaagctc aacctcttta   5040
tgggagctat tccctaaagc aatgaggacc gcaataaaaa ctcacaatga cattatgcgt   5100
cgtcaactac gaattttacgg tggttacgaa gtaaagacag aaggagacgc ctttatggtg   5160
gcatttccta cgccaactag tggtctgaca tggtgcttaa gtgttcaatt aaaactcttg   5220
gatgcacaat ggccggagga aattacctca gttcaagacg gctgccaagt tacggataga   5280
aatggtaaca ttatcatca aggcctatca gttagaatgg ttcattg gggctgccca   5340
gttccagagc ttgatttagt gactcaaaga atggactatt ggggccgat ggtcaataag   5400
gcagcaaggg tccagggcgt cgctgacggt ggtcagattg caatgagtag tgattttttac   5460
tctgaattca acaagataat gaagtatcat gagcgagtag tgaagggcaa ggaatctctc   5520
aaggaagttt atggtgaaga aaatatcgga gaggttcttg aaagagaaat tgccatgctg   5580
gaaagtattg gttgggcatt ttttgacttt ggcgagcata agctaaaggg actcgaaacc   5640
aaagaactcg ttactattgc gtatcctaag attcttgctt ccagacacga atttgcatct   5700
gaagatgagc agtcaaaatt aatcaatgaa acgatgttgt ttcgtttaag agtcatttca   5760
aacagactgg aatctataat gtcagcttta agcggccgat ttattgaact agactctgag   5820
acggagggaa gttatattaa atttaaccct aaagttgaaa atggtattat gcaatcgatt   5880
tctgagaagg atgcgttgtt attttttgat catgtaatta ctagaatcga atccagtgtg   5940
gcattattac atttacgaca acagaggtgt tcaggactgg aaatttgcag aaacgataaa   6000
acatctgctc gaagcaatat tttcaatgtt gttgacgaac ttttacaaat ggttaagaac   6060
gcaaaggatt tatcaacttg a                                            6081
```

```
SEQ ID NO: 2           moltype = AA   length = 2026
FEATURE                Location/Qualifiers
source                 1..2026
                       mol_type = protein
                       organism = Saccharomyces cerevisiae
SEQUENCE: 2
MSSKPDTGSE ISGPQRQEEQ EQQIEQSSPT EANDRSIHDE VPKVKKRHEQ NSGHKSRRNS     60
AYSYYSPRSL SMTKSRESIT PNGMDDVSIS NVEHPRPTEP KIKRGPYLLK KTLSSLSMTS    120
ANSTHDDNKD HGYALNSSKT HNYTSTHNHH DGHHDHHHVQ FFPNRKPSLA ETLFKRFSGS    180
NSHDGNKSGK ESKVANLSLS TVNPAPANRK PSKDSTLSNH LADNVPSTLR RKVSSLVRGS    240
SVHDINNGIA DKQIRPKAVA QSENTLSGNK VPNSKRSHRK SFLLGSTSSS SSRRGSNVSS    300
MTNSDSASMA TSGSHVLQHN VSNVSPTTKS KDSVNSESAD HTNNKSEKVT PEYNENIPEN    360
SNSDNKREAT TPTIETPISC KPSLFRLDTN LEDVTDITKT VPPTAVNSTL NSTHGTETAS    420
PKTVIMPEGP RKSVSMADLS VAAAAPNGEF TSTSNDRSQW VAPQSWDVET KRKKTKPKGR    480
SKSRRSSIDA DELDPMSPGP PSKKDSRHHH DRKDNESNVT AGDSNSSFVD ICKENVPNDS    540
KTALDTKSVN RLKSNLAMSP PSIRYAPSNL DGDYDTSSTS SSLPSSSISS EDTSSCSDSS    600
SYTNAYMEAN REQDNKTPIL NKTKSYTKKF TSSSVNMNSP DGAQSSGLLL QDEKDDEVEC    660
QLEHYYKDFS DLDPKRHYAI RIFNTDDTFT TLSCTPATTV EEIIPALKRK FNITAQGNFQ    720
ISLKVGKLSK ILRPTSKPIL IERKLLLLNG YRKSDPLHIM GIEDLSFVFK FLFHPVTPSH    780
FTPEQEQRIM RSEFVHVDLR NMDLTTPPII FYQHTSEIES LDVSNNANIF LPLEFIESSI    840
KLLSLRMVNI RASKFPSNIT KAYKLVSLEL QRNFIRKVPN SIMKLSNLTI LNLQCNELES    900
LPAGFVELKN LQLLDLSSNK FMHYPEVINY CTNLLQIDLS YNKIQSLPQS TKYLVKLAKM    960
NLSHNKLNFI GDLSEMTDLR TLNLRYNRIS SIKTNASNLQ NHLFLTDNRIS NFEDTLPKLR   1020
ALEIQENPIT SISFKDFYPK NMTSLTLNKA QLSSIPGELL TKLSFLEKLE LNQNNLTRLP   1080
QEISKLTKLV FLSVARNKLE YIPPELSQLK SLRTLDLHSN NIRDFVDGME NLELTSLNIS   1140
SNAFGNSSLE NSFYHNMSYG SKLSKSLMFF IAADNQFDDA MWPLFNCFVN LKVLNLSYNN   1200
FSDVSHMKLE SITELYLSGN KLTTLSGDTV LKWSSLKTLM LNSNQMLSLP AELSNLSQLS   1260
VFDVGANQLK YNISNYHYDW NWRNNKELKY LNFSGNRRFE IKSFISHDID ADLSDLTVLP   1320
QLKVLGLMDV TLNTTKVPDE NVNFRLRTTA SIINGMRYGV ADTLGQRDYV SSRDVTFERF   1380
RGNDDECLLC LHDSKNQNAD YGHNISRIVR DIYDKILIRQ LERYGDETDD NIKTALRFSF   1440
LQLNKEINGM LNSVDNGADV ANLSYADLLS GACSTVIYIR GKKLFAANLG DCMAILSKNN   1500
GDYQTLTKQH LPTKREEYER IRISGGYVNN GKLDGVVDVS RAVGFFDLLP HIHASPDISV   1560
VTLTKADEML IVATHKLWEY MDVDTVCDIA RENSTDPLRA AAELKDHAMA YGCTENITIL   1620
CLALYENIQQ QNRFTLNKNS LMTRRSTFED TTLRRLQPEI SPPTGNLAMV FTDIKSSTFL   1680
WELFPNAMRT AIKTHNDIMR RQLRIYGGYE VKTEGDAFMV AFPTPTSGLT WCLSVQLKLL   1740
DAQWPEEITS VQDGCQVTDR NGNIIYQGLS VRMGIHWGCP VPELDLVTQR MDYLGPMVNK   1800
AARVQGVADG GQIAMSSDFY SEFNKIMKYH ERVVKGKESL KEVYGEEIIG EVLEREIAML   1860
ESIGWAFFDF GEHKLKGLET KELVTIAYPK ILASRHEFAS EDEQSKLINE TMLFRLRVIS   1920
NRLESIMSAL SGGFIELDSR TEGSYIKFNP KVENGIMQSI SEKDALLFFD HVITRIESSV   1980
ALLHLRQQRC SGLEICRNDK TSARSNIFNV VDELLQMVKN AKDLST                  2026
```

```
SEQ ID NO: 3           moltype = AA   length = 686
FEATURE                Location/Qualifiers
source                 1..686
                       mol_type = protein
                       organism = Geobacillus stearothermophilus
SEQUENCE: 3
```

```
SSSASVKGDV  IYQIIIDRFY  DGDTTNNNPA  KSYGLYDPTK  SKWKMYWGGD  LEGVRQKLPY   60
LKQLGVTTIW  LSPVLDNLDT  LAGTDNTGYH  GYWTRDFKQI  EEHFGNWTTF  DTLVNDAHQN  120
GIKVIVDFVP  NHSTPFKAND  STFAEGGALY  NNGTYMGNYF  DDATKGYFHH  NGDISNWDDR  180
YEAQWKNFTD  PAGFSLADLS  QENGTIAQYL  TDAAVQLVAH  GADGLRIDAV  KHFNSGFSKS  240
LADKLYQKKD  IFLVGEWYGD  DPGTANHLEK  VRYANNSGVN  VLDFDLNTVI  RNVFGTFTQT  300
MYDLNNMVNQ  TGNEYKYKEN  LITFIDNHDM  SRFLSVNSNK  ANLHQALAFI  LTSRGTPSIY  360
YGTEQYMAGG  NDPYNRGMMP  AFDTTTTAPK  EVSTLAGLRR  NNAAIQYGTT  TQRWINNDVY  420
IYERKFFNDV  VLVAINRNTQ  SSYSISGLQT  ALPNGSYADY  LSGLLGGNGI  SVSNGSVASF  480
TLAPGAVSVW  QYSTSASAPQ  IGSVAPNMGI  PGNVVTIDGK  GFGTTQGTVT  FGGVTATVKS  540
WTSNRIEVYV  PNMAAGLTDV  KVTAGGVSSN  LYSYNILSGT  QTSVVFTVKS  APPTNLGDKI  600
YLTGNIPELG  NWSTDTSGAV  NNAQGPLLAP  NYPDWFYVFS  VPAGKTIQFK  FFIKRADGTI  660
QWENGSNHVA  TTPTGATGNI  TVTWQN                                          686

SEQ ID NO: 4            moltype = AA  length = 434
FEATURE                 Location/Qualifiers
source                  1..434
                        mol_type = protein
                        organism = Pyrococcus furiosus
SEQUENCE: 4
KYLELEEGGV  IMQAFYWDVP  GGGIWWDHIR  SKIPEWYEAG  ISAIWLPPPS  KGMSGGYSMG   60
YDPYDYFDLG  EYYQKGTVET  RFGSKEELVR  LIQTAHAYGI  KVIADVVINH  RAGGDLEWNP  120
FVGDYTWTDF  SKVASGKYTA  NYLDFPHPNEL HCCDEGTFGG  FPDICHHKEW  DQYWLWKSNE  180
SYAAYLRSIG  FDGWRFDYVK  GYGAWVVRDW  LNWWGGWAVG  EYWDTNVDAL  LSWAYESGAK  240
VFDFPLYYKM  DEAFDNNNIP  ALVYALQNGQ  TVVSRDPFKA  VTFVANHDTD  IIWNKYPAYA  300
FILTYEGQPV  IFYRDFEEWL  NKDKLINLIW  IHDHLAGGST  TIVYYDNDEL  IFVRNGDSRR  360
PGLITYINLS  PNWVGRWVYV  PKFAGACIHE  YTGNLGGWVD  KRVDSSGWVY  LEAPPHDPAN  420
GYYGYSVWSY  CGVG                                                       434

SEQ ID NO: 5            moltype = DNA  length = 6105
FEATURE                 Location/Qualifiers
source                  1..6105
                        mol_type = other DNA
                        organism = Saccharomyces cerevisiae
SEQUENCE: 5
atgtcatcaa  aacctgatac  tggttcggaa  atttctggcc  ctcagcgaca  ggaagaacaa    60
gaacaacaga  tagagcagag  ctcacctacg  gaagcaaacg  ataagagcat  tcatgatgag   120
gtaccaaaag  tcaagaagcg  tcacgaacaa  aatagtggtc  acaaatcaag  aaggaatagc   180
gcatatagtt  attacagccc  acggtcgctt  tctatgacca  aaagcaggga  gagtatcact   240
ccaaatggta  tggatgatgt  aagtatttcg  aacgtggaac  atccaaggcc  gacagaaccg   300
aaaatcaaaa  ggggtccata  tttactgaag  aaaacattga  gcagtctttc  aatgacgagc   360
gcgaatagta  ctccatgatga taataaagac  cacggttacg  ctttgaattc  atccaagacg   420
cacaactaca  catctactca  taaccatcat  gacggtcatc  atgatcatca  tcatgttcag   480
tttttttccca atggaagcc  atcattagcg  gaaacctctat tcaaaaggtt  ttcagggtca   540
aacagtcacg  atggcaataa  gtcaggaaag  gaaagtaaag  ttgctaacct  ttcccttttca  600
acggtaaatc  ctgcacctgc  taataggaaa  ccttctaaag  actccacttt  atctaatcac   660
ttggctgata  acgtgccaag  cacttttcga  aggaaagtgt  cctcattggt  acgtggttct   720
tccgtccatg  atataaataa  tggtattgca  gataaacaga  ttagaccaaa  gactgttgcg   780
caatcagaaa  atacattaca  ttcatccgat  gttcccaata  gcaaacgctc  gcacagaaaa   840
agctttctgc  taggctccac  atcttcttca  agcagtagaa  gaggttcaaa  tgtcagttca   900
atgactaaca  gtgacagtgc  aagtatgcg  acgtcgggta  gtcatgttct  ccaacataac   960
gtatctaatg  ttttctccaac tactaaaagt  aaggacagcg  ttaacagcga  atccgcgat  1020
cacactaata  ataaatccga  gaaagtgact  ccagaatata  atgagaacat  tccgaaaat  1080
tctaactctg  acaacaaacg  cgaagccaca  acgcctacta  tagaaacacc  catttcatgt  1140
aaaccatccc  ttttcaggct  agatacaaac  cttgaggatg  ttactgatat  tacaaagacg  1200
gtgccaccca  ccgctgtcaa  ttctacacta  aattctacac  acgggactga  gactgcctca  1260
cccaaaacgg  tgatcatgcc  tgaaggtcct  aggaagtcgg  tgtcaatggc  tgatctctcc  1320
gtcgctgccg  cagcacctaa  tggtgaattc  acatcaactt  ccaatgatag  atcacaatgg  1380
gtagcacctc  aaagctggga  tgtggaaacc  aaaaggaaaa  aaacaaaacc  taaggggaga  1440
tcgaaatcaa  gaaggtcaag  tatgatgct  gatgaacttg  atcccatgtc  accggggcca  1500
ccttcaaaaa  aagactctcg  tcatcgtaag  aaccgacact  ctcgtcatca  tcacgatcga  1560
aaggataacg  aatcaatggt  cactgcgggt  gacagtaact  caagttttgt  tgatatatgt  1620
aaagaaaacg  ttccgaatga  tagcaagacc  gcactcgata  ctaaatcgt  gaaccgctta  1680
aaaagtaatt  tggctatgag  tcccccaagt  atacgatatg  ctccatcaaa  tttagatggg  1740
gactacgaca  cgtcttccac  ttcctcatct  ttaccgtact  catctattag  ttcagaagat  1800
acatcttcct  gcagcgattc  ctcttcgtac  actaacgcgt  atatggaggc  caaccgagag  1860
caggataata  aaacaccgat  cctgaataaa  acgaaatcgt  ataccaagaa  atttacatcc  1920
tcttcggtaa  atatgaattc  accagatggt  gcccagagtt  ctggattatt  actacaagat  1980
gagaaggacg  atgaggtcga  gtgccaactg  gaacattact  ataaagattt  cagtgattta  2040
gatccaaaga  ggcactgatc  tattcgtata  ttcaatactg  atgacttt  tacgactctc  2100
tcatgtactc  cagcgactac  cgtcgaagag  ataatacctg  cacttaaaag  aaaatttaac  2160
attacagcgc  aagggaattt  tcaaatttcc  ctgaaggtgg  gaaagttgtc  aaaaattttg  2220
agaccaactt  cgaaacctat  tttaattgaa  agaaaacttt  tactttgaa  tggttatcga  2280
aagtcagacc  cacttcatat  tatgggtata  gaggatttaa  gttttgtttt  taagtttctt  2340
ttccatctca  tcacaccttc  tcacttttact  cctgaacaag  aacaagaat  atgagaagc  2400
gaatttgttc  acgtagattt  aaggaatatg  gatctgacta  cacctccat  catttttttac  2460
cagcatacgt  cagaaatagaa agtttagac  gttctaata  acgtaaatat  attcctacct  2520
ctggagttca  ttgaaagctc  gattaaatta  ttaagtttga  gaatggttaa  tattagagca  2580
tctaaatttc  cttccaatat  cactaaggcg  tataaactag  tatctttgga  attacagaga  2640
aacttcataa  gaaaagtacc  gaactcaatc  atgaaactga  gtaattaaac  gatattaaac  2700
```

```
cttcaatgta atgagcttga aagcctaccg gctggatttg ttgaactgaa aaatctgcaa   2760
ttgctagact tgtcttcaaa caagttcatg cactacccag aagttattaa ctactgcacc   2820
aatctttac aaatagacct atcatataat aaaatccaaa gcttaccaca gtccactaag    2880
tacctagtaa agcttgcgaa gatgaacctt tctcataaca aactaaattt tataggcgac   2940
ttatcggaaa tgcaaatttt gaggacgctg aacctaagat ataacagaat atcatcaatt   3000
aagacaaatg cgtctaactt gcagaacctt tttttaacag ataatagaat ttcgaactt    3060
gaagacactt tgccgaaact aagagccctt gaaattcaag agaatccaat cacttctata   3120
tccttcaaag atttttatcc aaaaaacatg acaagtttga cgttaacaa ggcacagtta    3180
tcgagtattc ctggagaatt actcaccaaa ctatctttcc tcgagaaact tgaacttaat   3240
cagaataatt tgactagact gccacaggag atatccaagt tgactaaatt agttttcctt   3300
tcagtggcga gaaacaaact agagtatatt ccacccgagc tatctcaact gaaaagtttg   3360
aggacattag atctacattc taacaacata agggactttg ttgacggtat ggaaaacctt   3420
gaactaacat cgctaaatat ttcatcgaat gcattcggta actcagctt agaaaattct    3480
ttttaccata acatgtcata tgggtcaaag ttatctaaca gcctgatgtt ttttattgct   3540
gcagacaatc aatttgatga tgctatgtgg cctctttca attgctttgt caatctgaaa    3600
gtgctaaatc tttcttacaa caattttca gatgtatcgc acatgaaact tgagagcatt    3660
accgaattgt acctctccgg taataagctc acgacattgt cgggtgatac agttttgaaa   3720
tggagctctt taaagacttt aatgttgaat agtaaccaaa tgttatctct gcctgcagaa   3780
ttatcaaatc tctcacagct aagtgtattt gatgttggag caaatcaatt aaagtataat   3840
atatcaaact atcattacga ttggaactgg aggaataata aagaactaaa atatttgaat   3900
ttttcaggaa atcgaaggtt tgaaataaag tcatttataa gtcacgatat tgatgctgat   3960
ttgtcagatc tgacagtatt acctcagtta aaggtactag gtttaatgta cgtaacttta   4020
aatactacca aagtaccgga tgaaaatgtc aatttccgtt taaggacaac tgcatcaata   4080
ataaatggga tgcgctacgg tgttgctgat acattaggtc aaagagacta tgtgtcatct   4140
cgtgatgtta cctttgaaag attccgcgga aatgacgacg aatgcttact atgtcttcat   4200
gatagtaaaa accaaaatgc agattatggc cacaatatat caagaattgt tagagatatt   4260
tacgataaaa tactgatcag acaactggaa aggtatggaa acgaaacaga tgataatata   4320
aaaactgcac ttcgtttcag tttttttgcaa ctgaataagg agattaacgg aatgctaaat   4380
tctgttgata atggtgccga tgttgccaat ctttcatatg cagacttgct aagtggcgct   4440
tgctctactg tgatatatat cagagggaag aaactcttcg ctgcaaattt aggtgactgt   4500
atggctattt tatccaaaaa caatggtgac taccaaacgc taaccaaaca acatctccca   4560
acaaagcggg aagaatacga gaggatcaga atatctggcg ggtatgtcaa caatggaaaa   4620
ttagatggtg ttgtagatgt gtctagagca gtgggttttt tgatttgct tccccacatt    4680
catgcttctc ccgacatatc tgtcgtgaca ttaacaaag cagacgagat gcttattgta   4740
gcaacgcata agttatggga tacatggac gtggatacag tttgtgatat cgcgcgtgag   4800
aatagtactg atccactccg tgccgcagct gagttgaagg atcatgccat ggcttacggc   4860
tgtacagaga atattacaat tttgtgcctt gctctttacg agaacattca gcaacaaat    4920
cggttcactt taaataaaaa ctctttaatg actagaagaa gtacttcga ggatactaca    4980
ttaagaagac ttcaacctga gatttctccg ccaacaggta acctagcact ggtcttcact   5040
gatatcaaaa gctcaacctt cttatgggag ctattcccta acgcaatgag gaccgcaata   5100
aaaactcaca atgacattat gcgtcgtcaa ctacgaattt acggtggtta cgaagtaaag   5160
acagaaggag acgcctttat ggtggcattt cctacgccaa ctagtggtct gacatggtgc   5220
ttaagtgttc aattaaaact cttggatgca caatggccgg aggaaattac ctcagttcaa   5280
gacggctgcc aagttacgga tagaaatggt aacattatct atcaaggcct atcagttaga   5340
atgggtattc attggggctg cccagttcca gagcttgatt tagtgactca agaatggac    5400
tatttgggc cgatggtcaa taaggcagca agggtccagg gcgtcgctga cggtggtcag   5460
attgcaatga gtagtgattt ttactctgaa ttcaacaaga taatgaagta tcatgagcga   5520
gtagtgaagg gcaaggaatc tctcaaggaa gtttatggtg aagaaattat cggagaggtt   5580
cttgaaagag aaatttgccat gctggaaagt attggttggg catttttga ctttggcgag   5640
cataagctaa agggactcga aaccaaagaa ctcgttacta ttgcgtatcc taagattctt   5700
gcttccagac acgaatttgc atctgaagat gagcagtcaa aattaatcaa tgaaacgatg   5760
ttgtttcgtt taagagtcat ttcaaacaga ctgaatccta aatgtcagc tttaagcggc   5820
ggatttattg aactagactc tcggacggag ggaagttata ttaaatttaa ccctaaagtt   5880
gaaaatggta ttatgcaatc gatttctgag aaggatgcgt tgttattttt tgatcatgta   5940
attactagaa tcgaatccag tgtggcatta ttacatttac gacaacagag gtgttcagga   6000
ctggaaattt gcagaaacga taaaacatct gctcgaagca atattttcaa tgttgttgac   6060
gaactttac aaatggttaa gaacgcaaag gatttatcga cttga                   6105

SEQ ID NO: 6           moltype = AA   length = 2034
FEATURE                Location/Qualifiers
source                 1..2034
                       mol_type = protein
                       organism = Saccharomyces cerevisiae
SEQUENCE: 6
MSSKPDTGSE ISGPQRQEEQ EQQIEQSSPT EANDRSIHDE VPKVKKRHEQ NSGHKSRRNS    60
AYSYYSPRSL SMTKSRESIT PNGMDDVSIS NVEHPRPTEP KIKRGPYLLK KTLSSLSMTS   120
ANSTHDDNKD HGYALNSSKT HNYTSTHNHH DGHHDHHHVQ FFPNRKPSLA ETLFKRFSGS   180
NSHDGNKSGK ESKVANLSLS TVNPAPANRK PSKDSTLSNH LADNVPSTLR RKVSSLVRGS   240
SVHDINNGIA DKQIRPKTVA QSENTLHSSD VPNSKRSHRK SFLLGSTSSS SSRRGSNVSS   300
MTNSDSASMA TSGSHVLQHN VSNVSPTTKS KDSVNSESAD HTNNKSEKVT PEYNENIPEN   360
SNSDNKREAT TPTIETPISC KPSLFRLDTN LEDVTDITKT VPPTAVNSTL NSTHGTETAS   420
PKTVIMPEGP RKSVSMADLS VAAAAPNGEF TSTSNDRSQW VAPQSWDVET KRKKTKPKGR   480
SKSRRSSIDA DELDPMSPGP PSKKDSRHRK NRHSRHHHDR KDNESMVTAG DSNSSFVDIC   540
KENVPNDSKT ALDTKSVNRL KSNLAMSPPS IRYAPSNLDG DYDTSSTSSS LPSSSISSED   600
TSSCSDSSSY TNAYMEANRE QDNKTPILNK TKSYTKKFTS SSVNMNSPDG AQSSGLLLQD   660
EKDDEVECQL EHYYKDFSDL DPKRHYAIRI FNTDDTFTTL SCTPATTVEE IIPALKRKFN   720
ITAQGNFQIS LKVGKLSKIL RPTSKPILIE RKLLLLNGYR KSDPLHIMGI EDLSFVFKFL   780
FHPVTPSHFT PEQEQRIMRS EFVHVDLRNM DLTTPPIIFY QHTSEIESLD VSNNVNIFLP   840
LEFIESSIKL LSLRMVNIRA SKFPSNITKA YKLVSLELQR NFIRKVPNSI MKLSNLTILN   900
```

```
LQCNELESLP AGFVELKNLQ LLDLSSNKFM HYPEVINYCT NLLQIDLSYN KIQSLPQSTK    960
YLVKLAKMNL SHNKLNFIGD LSEMTNLRTL NLRYNRISSI KTNASNLQNL FLTDNRISNF   1020
EDTLPKLRAL EIQENPITSI SFKDFYPKNM TSLTLNKAQL SSIPGELLTK LSFLEKLELN   1080
QNNLTRLPQE ISKLTKLVFL SVARNKLEYI PPELSQLKSL RTLDLHSNNI RDFVDGMENL   1140
ELTSLNISSN AFGNSSLENS FYHNMSYGSK LSKSLMFFIA ADNQFDDAMW PLFNCFVNLK   1200
VLNLSYNNFS DVSHMKLESI TELYLSGNKL TTLSGDTVLK WSSLKTLMLN SNQMLSLPAE   1260
LSNLSQLSVF DVGANQLKYN ISNYHYDWNW RNNKELKYLN FSGNRRFEIK SFISHDIDAD   1320
LSDLTVLPQL KVLGLMDVTL NTTKVPDENV NFRLRTTASI INGMRYGVAD TLGQRDYVSS   1380
RDVTFERFRG NDDECLLCLH DSKNQNADYG HNISRIVRDI YDKILIRQLE RYGDETDDNI   1440
KTALRFSFLQ LNKEINGMLN SVDNGADVAN LSYADLLSGA CSTVIYIRGK KLFAANLGDC   1500
MAILSKNNGD YQTLTKQHLP TKREEYERIR ISGGYVNNGK LDGVVDVSRA VGFFDLLPHI   1560
HASPDISVVT LTKADEMLIV ATHKLWEYMD VDTVCDIARE NSTDPLRAAA ELKDHAMAYG   1620
CTENITILCL ALYENIQQQN RFTLNKNSLM TRRSTFEDTT LRRLQPEISP PTGNLAMVFT   1680
DIKSSTFLWE LFPNAMRTAI KTHNDIMRRQ LRIYGGYEVK TEGDAFMVAF PTPTSGLTWC   1740
LSVQLKLLDA QWPEEITSVQ DGCQVTDRNG NIIYQGLSVR MGIHWGCPVP ELDLVTQRMD   1800
YLGPMVNKAA RVQGVADGGQ IAMSSDFYSE FNKIMKYHER VVKGKESLKE VYGEEIIGEV   1860
LEREIAMLES IGWAFFDFGE HKLKGLETKE LVTIAYPKIL ASRHEFASED EQSKLINETM   1920
LFRLRVISNR LESIMSALSG GFIELDSRTE GSYIKFNPKV ENGIMQSISE KDALLFFDHV   1980
ITRIESSVAL LHLRQQRCSG LEICRNDKTS ARSNIFNVVD ELLQMVKNAK DLST         2034

SEQ ID NO: 7           moltype = DNA  length = 6105
FEATURE                Location/Qualifiers
source                 1..6105
                       mol_type = other DNA
                       organism = Saccharomyces cerevisiae
SEQUENCE: 7
atgtcatcaa aacctgatac tggttcggaa atttctggcc ctcagcgaca ggaagaacaa     60
gaacaacaga tagagcagag ctcgcctacg gaagcaaacg atagaagcat tcatgatgag    120
gtaccaaaag tcaagaagcg tcacgaacaa atagtggtc acaaatcaag aaggaatagc    180
gcatatagtt attacagccc acggtcgctt tctatgacca aaagcaggga gagtatcact    240
ccaaatggta tggatgatgt aagtatttcg aacgtggaac atccaaggcc gacagaaccg    300
aaaatcaaaa ggggtccata tttactgaag aaaacattga gcagtctttc aatgacgagc    360
gcgaatagta ctcatgatga taataaagac cacggttacg ctttgaattc atccaagacg    420
cacaactaca catctactca taaccatcat gacggtcatc atgatcatca tcatgttcag    480
tttttttccca ataggaagcc atcattagcg gaaaccctat tcaaaaggtt ttcagggtca    540
aacagtcacg atggcaataa gtcaggaaag gaaagtaaag ttgctaacct ttcccttttca    600
acggtaaatc ctgcacctgc taataggaaa ccttctaaag actccacttt atctaatcac    660
ttggctgata acgtgccaag cacttttacga aggaaagtgt cctcattggt acgtggttct    720
tccgtccatg atataaataa tggtattgca gataaacaga ttagaccaag ggctgttgcg    780
caatcagaaa atacattaca ttcatccgat gttcccaata gcaaacgctc gcacagaaaa    840
agctttctgc taggctccac atcttcttca agcagtagaa gaggtcaaa tgtcagttca    900
atgactaaca gtgacagtgc aagtatgcg acgtcgggta gtcatgttct ccaacataac    960
gtatctaatg tttctccaac tactaaaagt aaggacagcg ttaacagcga atccgccatg   1020
cacactaata ataaatccga aaagtgact ccagaatata atgagaacat tccggaaaat   1080
tctaactctg acaacaaacg cgaagccaca acgcctacta tagaaacacc catttcatgt   1140
aaaccatccc ttttcaggct agatacaaac cttgaggatg ttactgatat tacaaagacg   1200
gtgccacccca ccgctgtcaa ttctcacacta aattctacac acgggactga gactgcctca   1260
cccaaaacgg tgatcatgcc tgaaggtcct aggaagtcgg tgtcaatggc tgatctctcc   1320
gtcgctgccg cagcacctaa tggtgaattc acatcaactt ccaatgatag atcacaatgg   1380
gtagcacctc aaagctggga tgtggaaacc aaaaggaaaa aaacaaaacc taagggagaa   1440
tcgaaatcaa gaaggtcaag tatagatgct gatgaacttg atcccatgtc accgggggcca   1500
ccttcaaaaa aagactctcg tcatcgtaag aaccgacact ctcgtcatca tcacgatcga   1560
aaggataacg aatcaatggt cactgcgggt gacagtaact caagttttgt tgatatatgt   1620
aaagaaaacg ttcgaatga tagcaagacc gcactcgata ctaaatctgt gaaccgctta   1680
aaaagtaatt tggctatgag tccccccaagt atacgatatg ctccatcaaa tttagatggg   1740
gactacgaca cgtcttccac ttcctcatct ttaccgtcct catctattag ttcagaagat   1800
acatcttcct gcagcgattc ctcttcgtac actaacgcgt atatggaggc caaccgagag   1860
caggataata aaacaccgat cctgaataaa acgaaatcgt ataccaagaa atttacatcc   1920
tcttcggtaa atatgaattc accagatggt gcccagagtc ctggattatt actacaagat   1980
gagaaggacg atgaggtcga gtgccaactg gaacattact ataaagattt cagtgattta   2040
gatccaaaga ggcactatgc tattcgtata ttcaatactg atgacacttt tacgactctc   2100
tcatgtactc cagcgactac cgtcgaagag ataatacctg cacttaaaag aaaatttaac   2160
attacagcgc aagggaattt tcaaatttcc ctgaaggtgg gaaagttgtc aaaaatttg   2220
agaccaactt cgaaactat tttaattgaa agaaaactt tacttttgaa tggttatcga   2280
aagtcagacc cacttcatat tatgggtata gaggatttaa gttttgtttt taagtttctt   2340
ttccatcctg tcacaccttc tcactttact cctgaacaag aacaaagaat aatgagaagc   2400
gaatttgttc acgtagattt aaggaatatg gatctgacta cacctcccat catttttac   2460
cagcatacgt cagaaataga aagtttagac gtttctaata acgcaaatat attcctacct   2520
ctggagttca ttgaaagctc gattaaatta ttaagtttga gaatggttaa tattagagca   2580
tctaaatttc cttccaatat cactgaggcg tataaactag tatctttgga attacagaga   2640
aacttcataa gaaaagtacc gaactcaatc atgaaactga gtaatttaac gatattaaac   2700
cttcaatgta atgagcttga aagcctaccg gctggatttg tgaactgaa aaatctgcaa   2760
ttgctagact tgtcttcaaa caagttcatg cactacccag aagttattaa ctactgcacc   2820
aatcttttca aaatagacct atcatataat aatcttaccaca gtccactaag   2880
tacctagtaa agcttgcgaa gatgaacctt tctcataaca aactaaattt tagggcgac   2940
ttatcggaaa tgacaaattt gaggacgctg aacctaagat ataacagaat atcatcaatt   3000
aagacaaatg cgtctaactt gcagaacctt ttttaacag ataatagaat tcgaactttt   3060
gaagacactt tgccgaaact aagagccctt gaaattcaag agaatccaat cacttctata   3120
tccttcaaag atttttatcc aaaaaacatg acaagttga cgttgaacaa ggcacagtta   3180
```

```
tcgagtattc ctggagaatt actcaccaaa ctatctttcc tcgagaaact tgaacttaat    3240
cagaataatt tgactagact gccacaggag atatccaagt tgactaaatt agttttcctt    3300
tcagtggcga gaaacaaact agagtatatt ccacccgagc tatctcaact gaaaagtttg    3360
aggacattag atctacattc taacaacata agggactttg ttgacggtat ggaaaacctt    3420
gaactaacat cgctaaatat ttcatcgaat gcattcgata actctagctt agaaaaattct   3480
```
Note: Above is partial. Full continuation:
```
tcgagtattc ctggagaatt actcaccaaa ctatctttcc tcgagaaact tgaacttaat    3240
cagaataatt tgactagact gccacaggag atatccaagt tgactaaatt agttttcctt    3300
tcagtggcga gaaacaaact agagtatatt ccacccgagc tatctcaact gaaaagtttg    3360
aggacattag atctacattc taacaacata agggactttg ttgacggtat ggaaaacctt    3420
gaactaacat cgctaaatat ttcatcgaat gcattcgata actctagctt agaaaattct    3480
ttttaccata acatgtcata tgggtcaaag ttatctaaaa gcctgatgtt tttattgct     3540
gcagacaatc aatttgatga tgctatgtgg cctcttttca attgctttgt caatctgaaa    3600
gtgctaaatc tttcttacaa caattttttca gatgtatcgc acatgaaact tgagagcatt   3660
accgaattgt acctctccgg taataagctc acgacattgt cgggtgatac agttttgaaa    3720
tggagctctt taaagacttt aatgttgaat agtaaccaaa tgttatctct gcctgcagaa    3780
ttatcaaatc tctcacagct aagtgtattt gatgttggag caaatcaatt aaagtataat    3840
atatcaaact atcattacga ttggaactgg aggaataata agaactaaa atatttgaat     3900
ttttcaggaa atcgaaggtt tgaaataaag tcatttataa gtcacgatat tgatgctgat    3960
ttgtcagatc tgacagtatt acctcagtta aaggtactag gttaatgaca cgtaactta     4020
aatactacca aagtaccgga tgaaaatgtc aattccgtt taaggacaac tgcatcaata    4080
ataaatggga tgcgctacgg tgttgctgat acattaggtc aaagagacta tgtgtcatct    4140
cgtgatgtta cctttgaaag attccgcgga aatgacgacg aatgcttact atgtcttcat    4200
gatagtaaaa accaaaatgc agattatggc cacaatattgt caagaattgt tagagatatt   4260
tacgataaaa tactgatcag acaactggaa aggtatggaa acgacacaga tgataatata    4320
aaaactgcac ttcgtttcag ttttttgcaa ctgaataagg agattaacgg aatgctaaat    4380
tctgttgata atggtgccga tgttgccaat cttcatatg cagacttgct aagtggcgct    4440
tgctctactg tgatatatat cagagggaag aaactcttcg ctgcaaattt aggtgactgt    4500
atggctattt tatccaaaaa caatggtgac taccaaacgc taaccaaaca acatctccca    4560
acaaagcggg aagaatacga gaggatcaga atatctggcg ggtatgtcaa caatggaaaa    4620
ttagatggtg ttgtagatgt gtctagagca gtgggttttt tgatttgct tccccacatt     4680
catgcttctc ccgacatatc tgtcgtgaca ttaacaaaag cagacgagat gcttattgta    4740
gcaacgcata agttatggga atacatggac gtggatacag tttgtgatat cgcgcgtgag    4800
aatagtactg atccactccg tgccgcagct gagttgaagg atcatgccat ggcttacggc    4860
tgtacagaga atattacaat tttgtgcctt gctcttttacg agaacattca gcaacaaat    4920
cggttcactt taaataaaa ctcttttaatg actagaagca gtactttcga ggatactaca    4980
ttaagaagac ttcaacctga gatttctccg ccaacaggta acctagcaat ggtcttcact    5040
gatatcaaaa gctcaacctt cttatggag ctattcccta acgcaatgag gaccgcaata    5100
aaaactcaca atgacattat gcgtcgtcaa ctacgaattt acggtggtta cgaagtaaag    5160
acagaaggag acgcctttat ggtggcattt cctacgcgaa ctagtggtct tacatggtgc    5220
ttaagtgttc aattaaaact cttggatgca caatggccgg aggaaattac ctcagttcaa    5280
gacggctgcc aagttacgga tagaaatggt aacattatct atcaaggcct atcagttaga    5340
atgggtattc attggggctg cccagttcca gagcttgatt tagtgactca agaatggac    5400
tatttgggc cgatggtcaa taaggcagca agggtccagg gcgtcgctga cggtggtcag    5460
attgcaatga gtagtgattt ttactctgaa ttcaacaaga taatgaagta tcatgaacga    5520
gtagtgaagg gcaaggaatc tctcaaggaa gtttatggtg aagaaattat cggagaggtt    5580
cttgaaaagag aaattgccat gctggaaagt attggttggg catttttga ctttggcgag    5640
cataagctaa agggactcga aaccaaagaa ctcgttacta ttgcgtatcc taagattctt    5700
gcttccagac acgaatttgc atctgaagat gagcagtcaa aattaatcaa tgaaacgatg    5760
ttgtttcatt taagagtcat ttcaaacaga ctgaatcta taatgtcagc tttaagcggc    5820
ggatttattg aactagactc tcggacggag ggaagttata ttaaatttaa ccctaaagtt    5880
gaaaatggta ttatgcaatc gatttctgag aaggatgcgt tgttatttt tgatcatgta    5940
attactagaa tcgaatccag tgtggcatta ttacatttac gacaacagga gtgttcagga    6000
ctggaaattt gcagaaacga taaaacatct gctcgaagca atattttcaa tgttgttgac    6060
gaacttttac aaatggttaa gaacgcaaag gatttatcaa cttga                    6105

SEQ ID NO: 8                 moltype = AA   length = 2034
FEATURE                      Location/Qualifiers
source                       1..2034
                             mol_type = protein
                             organism = Saccharomyces cerevisiae
SEQUENCE: 8
MSSKPDTGSE ISGPQRQEEQ EQQIEQSSPT EANDRSIHDE VPKVKKRHEQ NSGHKSRRNS      60
AYSYYSPRSL SMTKSRESIT PNGMDDVSIS NVEHPRPTEP KIKRGPYLLK KTLSSLSMTS    120
ANSTHDDNKD HGYALNSSKT HNYTSTHNHH DGHHDHHHVQ FFPNRKPSLA ETLFKRFSGS    180
NSHDGNKSGK ESKVANLSLS TVNPAPANRK PSKDSTLSNH LADNVPSTLR RKVSSLVRGS    240
SVHDINNGIA DKQIRPKAVA QSENTLHSSD VPNSKRSHRK SPLLGSTSSS SSRRGSNVSS    300
MTNSDSASMA TSGSHVLQHN VSNVSPTTKS KDSVNSESAD HTNNKSEKVT PEYNENIPEN    360
SNSDNKREAT TPTIETPISC KPSLFRLDTN LEDVTDITKT VPPTAVNSTL NSTHGTETAS    420
PKTVIMPEGP RKSVSMADLS VAAAAPNGEF TSTSNDRSQW VAPQSWDVET KRKKTKPKGR    480
SKSRRSSIDA DELDPMSPGP PSKKDSRHRK NRHSRHHHDR KDNESMVTAG DSNSSFVDIC    540
KENVPNDSKT ALDTKSVNRL KSNLAMSPPS IRYAPSNLDG DYDTSSTSSS LPSSSISSED    600
TSSCSDSSSY TNAYMEANRE QDNKTPILNK TKSYTKKFTS SSVNMNSPDG AQSSGLLLQD    660
EKDDEVECQL EHYYKDFSDL DPKRHYAIRI FNTDDTFTTL SCTPATTVEE IIPALRKFN     720
ITAQGNFQIS LKVGKLSKIL RPTSKPILIE RKLLLLNGYR KSDPLHIMGI EDLSFVFKFL    780
FHPVTPSHFT PEQEQRIMRS EFVHVDLRNM DLTTPPIIFY QHTSEIESLD VSNNANIFLP    840
LEFIESSIKL LSLRMVNIRA SKFPSNITEA YKLVSLELQR NFIRKVPNSI MKLSNLTILN    900
LQCNELESLP AGFVELKNLQ LLDLSSNKFM HYPEVINYCT NLLQIDLSYN KIQSLPQSTK    960
YLVKLAKMNL SHNKLNFIGD LSEMTNLRTL NLRYNRISSI KTNASNLQNL FLTDNRISNF   1020
EDTLPKLRAL EIQENPITSI SFKDFYPKNM TSLTLNKAQL SSIPGELLTK LSFLEKLELN   1080
QNNLTRLPQE ISKLTKLVFL SVARNKLEYI PPELSQLKSL RTLDLHSNNI RDFVDGMENL   1140
ELTSLNISSN AFGNSSLENS FYHNMSYGSK LSKSLMFFIA ADNQFDDAMW PLFNCFVNLK   1200
VLNLSYNNFS DVSHMKLESI TELYLSGNKL TTLSGDTVLK WSSLKTLMLN SNQMLSLPAE   1260
LSNLSQLSVF DVGANQLKYN ISNYHYDWNW RNNKELKYLN FSGNRRFEIK SFISHDIDAD   1320
LSDLTVLPQL KVLGLMDVTL NTTKVPDENV NFRLRTTASI INGMRYGVAD TLGQRDYVSS   1380
```

-continued

```
RDVTFERFRG NDDECLLCLH DSKNQNADYG HNISRIVRDI YDKILIRQLE RYGDDTDDNI 1440
KTALRFSFLQ LNKEINGMLN SVDNGADVAN LSYADLLSGA CSTVIYIRGK KLFAANLGDC 1500
MAILSKNNGD YQTLTKQHLP TKREEYERIR ISGGYVNNGK LDGVVDVSRA VGFFDLLPHI 1560
HASPDISVVT LTKADEMLIV ATHKLWEYMD VDTVCDIARE NSTDPLRAAA ELKDHAMAYG 1620
CTENITILCL ALYENIQQQN RFTLNKNSLM TRRSTFEDTT LRRLQPEISP PTGNLAMVFT 1680
DIKSSTFLWE LFPNAMRTAI KTHNDIMRRQ LRIYGGYEVK TEGDAFMVAF PTPTSGLTWC 1740
LSVQLKLLDA QWPEEITSVQ DGCQVTDRNG NIIYQGLSVR MGIHWGCPVP ELDLVTQRMD 1800
YLGPMVNKAA RVQGVADGGQ IAMSSDFYSE FNKIMKYHER VVKGKESLKE VYGEEIIGEV 1860
LEREIAMLES IGWAFFDFGE HKLKGLETKE LVTIAYPKIL ASRHEFASED EQSKLINETM 1920
LFHLRVISNR LESIMSALSG GFIELDSRTE GSYIKFNPKV ENGIMQSISE KDALLFFDHV 1980
ITRIESSVAL LHLRQQRCSG LEICRNDKTS ARSNIFNVVD ELLQMVKNAK DLST       2034
```

OPTIMIZATION OF YEAST HOST CELLS FOR THE PRODUCTION OF HETEROLOGOUS PROTEINS

CROSS-REFERENCE TO RELATED APPLICATIONS AND BIOLOGICAL DEPOSITS

The present application claims priority from U.S. provisional application 62/733,471 filed Sep. 19, 2018 and herewith incorporated in its entirety. The present application also includes the following biological deposits, all deposited at American Type Culture Collection (ATCC®) located at 10801 University Boulevard, Manassas, VA, U.S.A. 20110, an International Depositary Authority, under Budapest Treaty on Jul. 25, 2018: PTA-125175 (for strain M18151), PTA-125176 (for strain M18152) and PTA-125177 (for strain M18195) which are included herewith in their entirety.

REFERENCE TO AN ELECTRONIC SEQUENCE LISTING

The contents of the electronic sequence listing (419C1_SeqListing.xml; Size: 33,467 bytes; and Date of Creation: Dec. 18, 2023) is herein incorporated by reference in its entirety.

TECHNOLOGICAL FIELD

The present disclosure relates to yeast host cell capable of producing high yield of an heterologous protein having increased biological activity.

BACKGROUND

Heterologous proteins are often produced, on an industrial scale, in filamentous fungi or in bacteria using a fed batch fermentation. Filamentous fungi require growth on a complex (and usually highly viscous) medium and long fermentation times. Filamentous fungi are limited in expressing extracellular (secreted) heterologous proteins. *Bacillus* is often used as a bacterial host cell for the production of heterologous proteins. While *Bacillus* usually require a simple medium (that may be supplement with an additional protein source), they provide short fermentation times and offer interesting yields when the heterologous enzyme is produced in a recombinant fashion). *Bacillus* could be used to express heterologous proteins intracellularly as well as extracellularly.

It would be highly desirable to be provided with a host cell which could be used not only in a fed batch fermentation but in a continuous fermentation. It would also be desirable to be provided with a host cell capable of using a simple substrate and of generating the heterologous protein during a short fermentation. It would further be desirable to be provided with a host cell capable of producing not only a high yield of the heterologous protein but also heterologous proteins having high biological and/or specific activity.

BRIEF SUMMARY

The present disclosure concerns a recombinant yeast host cell capable of expressing a higher amount per cell of an heterologous protein.

In a first aspect, the present disclosure concerns a recombinant yeast host cell for making an increased amount of an heterologous protein. The recombinant yeast host cell has a first heterologous nucleic acid encoding the heterologous protein. The recombinant yeast host cell has an altered intracellular cyclic AMP (cAMP) signaling pathway. The recombinant yeast host cell can be obtained by introducing the first heterologous nucleic acid in an ancestral yeast host cell having the altered intracellular cAMP pathway. The altered intracellular cAMP pathway provides to the ancestral or the recombinant yeast host cell a substantially similar cAMP production in the presence and in the absence of a cAMP stimulus (understood to stimulate intracellular cAMP production in a control yeast cell). In an embodiment, the amount of heterologous protein per cell of the recombinant yeast host cell is increased with respect to a corresponding amount in a control yeast cell. In a further embodiment, the control yeast cell corresponds to biological deposit PTA-125176 or a yeast cell having the characteristics of the biological deposit PTA-125176. In another embodiment, the recombinant yeast host cell expresses a variant protein of the cAMP signaling pathway. In another embodiment, the variant protein is a variant CYR1 protein encoded by a variant CYR1 gene. In yet a further embodiment, the variant CYR1 gene is a native CYR1 gene. In an embodiment, the ancestral yeast host cell is biological deposit PTA-125175 or a yeast cell having the characteristics of the biological deposit PTA-125175. In still another embodiment, the ancestral yeast host cell is biological deposit PTA-125177 or a yeast cell having the characteristics of the biological deposit PTA-125177. In some embodiments, the recombinant yeast host cell comprises a second heterologous nucleic acid molecule comprising a variant CYR1 gene encoding a variant CYR1 protein. In some additional embodiments, the variant CYR1 gene has at least one single nucleotide polymorphism (SNP). For example, the at least one SNP can be G772A when using the numbering of the nucleic acid sequence of SEQ ID NO: 1 or 7, C2480T when using the numbering of the nucleic acid sequence of SEQ ID NO: 1, C2504T when using the numbering of the nucleic acid sequence of SEQ ID NO: 7, G2605A when using the numbering of the nucleic acid sequence of SEQ ID NO: 7; or C4305A when using the numbering of the nucleic acid sequence of SEQ ID NO: 7. In some embodiments, the variant CYR1 protein has at least one of the following variations: A258T when using the numbering of the amino acid sequence of SEQ ID NO: 2 or 8; A827V when using the numbering of the amino acid sequence of SEQ ID NO: 2; A835V when using the numbering of the amino acid sequence of SEQ ID NO: 8; E869K when using the numbering of the amino acid sequence of SEQ ID NO: 8; or D1435E when using the numbering of the amino acid sequence of SEQ ID NO: 8. In yet another embodiment, the recombinant yeast host cell exhibits polyploidy in at least one chromosome. For example, polyploidy can comprise triploidy in at least one first chromosome and tetraploidy in at least one second chromosome. In another embodiment, the heterologous protein is an heterologous enzyme such as, for example, a maltogenic alpha-amylase, an alpha-amylase, an oxidoreductase, a transferase, an hydrolase, a lyase, an isomerase, a phosphatase, a ligase, a glucoamylase, a fungal amylase, a phytase or a glucose oxidase. In an embodiment, the recombinant yeast host cell is from the genus *Saccharomyces*. In some additional embodiments, the recombinant yeast host cell is from the species *Saccharomyces cerevisiae*.

According to a second aspect, the present disclosure concerns a method of making a recombinant yeast host cell as defined herein. The method comprises a) selecting an ancestral yeast host cell having the altered intracellular cAMP pathway, wherein the altered intracellular cAMP pathway provides to the ancestral yeast host cell a substantially similar cAMP production in the presence and in the absence of a cAMP stimulus. The method also comprises b) introducing a first heterologous nucleic acid molecule encoding the heterologous protein in the selected ancestral yeast host cell to obtain the recombinant yeast host cell. In an embodiment, step a) comprises comparing the amount of the heterologous protein expressed in the ancestral yeast host cell to a corresponding amount in a control yeast cell and selecting the ancestral yeast host cell if the amount of the heterologous protein is higher than the corresponding amount in the control yeast cell. In an embodiment, control yeast cell corresponds to biological deposit PTA-125176 or a yeast cell having the characteristics of the biological deposit PTA-125176. In another embodiment, step a) comprises determining if the ancestral yeast host cell expresses a variant protein of the cAMP signaling pathway. In an embodiment, variant protein of the cAMP signaling pathway is a variant CYR1 gene encoding a variant CYR1 protein. In some embodiments, the variant CYR1 gene is a native CYR1 gene. In an embodiment, the selected ancestral yeast host cell is biological deposit PTA-125175 or a yeast cell having the characteristics of the biological deposit PTA-125175. In another embodiment, the selected ancestral yeast host cell is biological deposit PTA-125177 or a yeast cell having the characteristics of the biological deposit PTA-125177. In still another embodiment, the variant CYR1 gene is encoded by a second heterologous nucleic acid molecule. In some embodiments, the method further comprises introducing a second heterologous nucleic acid molecule encoding the variant CYR1 gene in the ancestral yeast host cell (prior to or after the selection step a). In an embodiment, the variant CYR1 gene has at least one single nucleotide polymorphism (SNP). In yet another embodiment, the at least one SNP is G772A when using the numbering of the nucleic acid sequence of SEQ ID NO: 1 or 7; C2480T when using the numbering of the nucleic acid sequence of SEQ ID NO: 1; C2504T when using the numbering of the nucleic acid sequence of SEQ ID NO: 7; G2605A when using the numbering of the nucleic acid sequence of SEQ ID NO: 7; or C4305A when using the numbering of the nucleic acid sequence of SEQ ID NO: 7. In still another embodiment, the variant CYR1 protein has at least one of the following variations: A258T when using the numbering of the amino acid sequence of SEQ ID NO: 2 or 8; A827V when using the numbering of the amino acid sequence of SEQ ID NO: 2; A835V when using the numbering of the amino acid sequence of SEQ ID NO: 8; E869K when using the numbering of the amino acid sequence of SEQ ID NO: 8; or D1435E when using the numbering of the amino acid sequence of SEQ ID NO: 8. In a further embodiment, the method further comprises determining if the ancestral yeast host cell exhibits polyploidy. In yet another embodiment, polyploidy is determined to be present if the ancestral yeast host cell exhibits triploidy in at least one first chromosome and tetraploidy in at least one second chromosome and selecting the ancestral yeast host cell exhibiting triploidy in the at least one first chromosome and tetraploidy in the at least one second chromosome. In a further embodiment, the heterologous protein is an heterologous enzyme such as, for example, at least one of a maltogenic alpha-amylase, an alpha-amylase, an oxidoreductase, a transferase, an hydrolase, a lyase, an isomerase, a phosphatase, a ligase, a glucoamylase, a fungal amylase, a phytase or a glucose oxidase. In an embodiment, the ancestral yeast host cell is from the genus *Saccharomyces*. In yet another embodiment, the ancestral yeast host cell is from the species *Saccharomyces cerevisiae*.

In a third aspect, the present disclosure concerns a recombinant yeast host cell obtainable or obtained by the method described herein.

In a fourth aspect, the present disclosure concerns a process for making a yeast product. The process comprises culturing the recombinant yeast host cell defined herein to obtain a cultured recombinant yeast host cell; and formulating the cultured yeast host cell into the yeast product. In some embodiments, the formulating step comprises lysing the cultured yeast host cell to obtain a lysed yeast product; and optionally drying the lysed recombinant yeast host cell to obtain a lysed and dried yeast product. In an embodiment, the yeast product is an autolysate, a yeast cell wall or a yeast extract. In a further embodiment, the yeast product is a substantially purified heterologous protein for example an heterologous enzyme.

In a fifth aspect, the present disclosure concerns a yeast product obtainable or obtained by the process described herein. In an embodiment, the yeast product can be a substantially purified heterologous protein such as, for example, an heterologous enzyme.

BRIEF DESCRIPTION OF THE DRAWINGS

Having thus generally described the nature of the invention, reference will now be made to the accompanying drawings, showing by way of illustration, a preferred embodiment thereof, and in which:

FIGS. 3A and C are representative of images taken after overnight growth in yeast extract peptone with 4% glucose whereas FIGS. 3B and D are representative images taken after one hour of transfer to fresh yeast extract peptone with 4% glucose. All images taken at 400× magnification.

FIGS. 6A and 6B provides the alignment of (FIG. 6A) the nucleic acid sequence of the CYR1 gene expressed in *S. cerevisiae* strain S288C (SEQ ID NO: 1), strain M18151 (SEQ ID NO: 5) and strain M18152 (SEQ ID NO: 7) and of (FIG. 6B) the amino acid sequence of the CYR1 protein expressed in *S. cerevisiae* strain S288C (SEQ ID NO: 2), strain M18151 (SEQ ID NO: 6) and strain M18152 (SEQ ID NO: 8).

DETAILED DESCRIPTION

Figure 1:
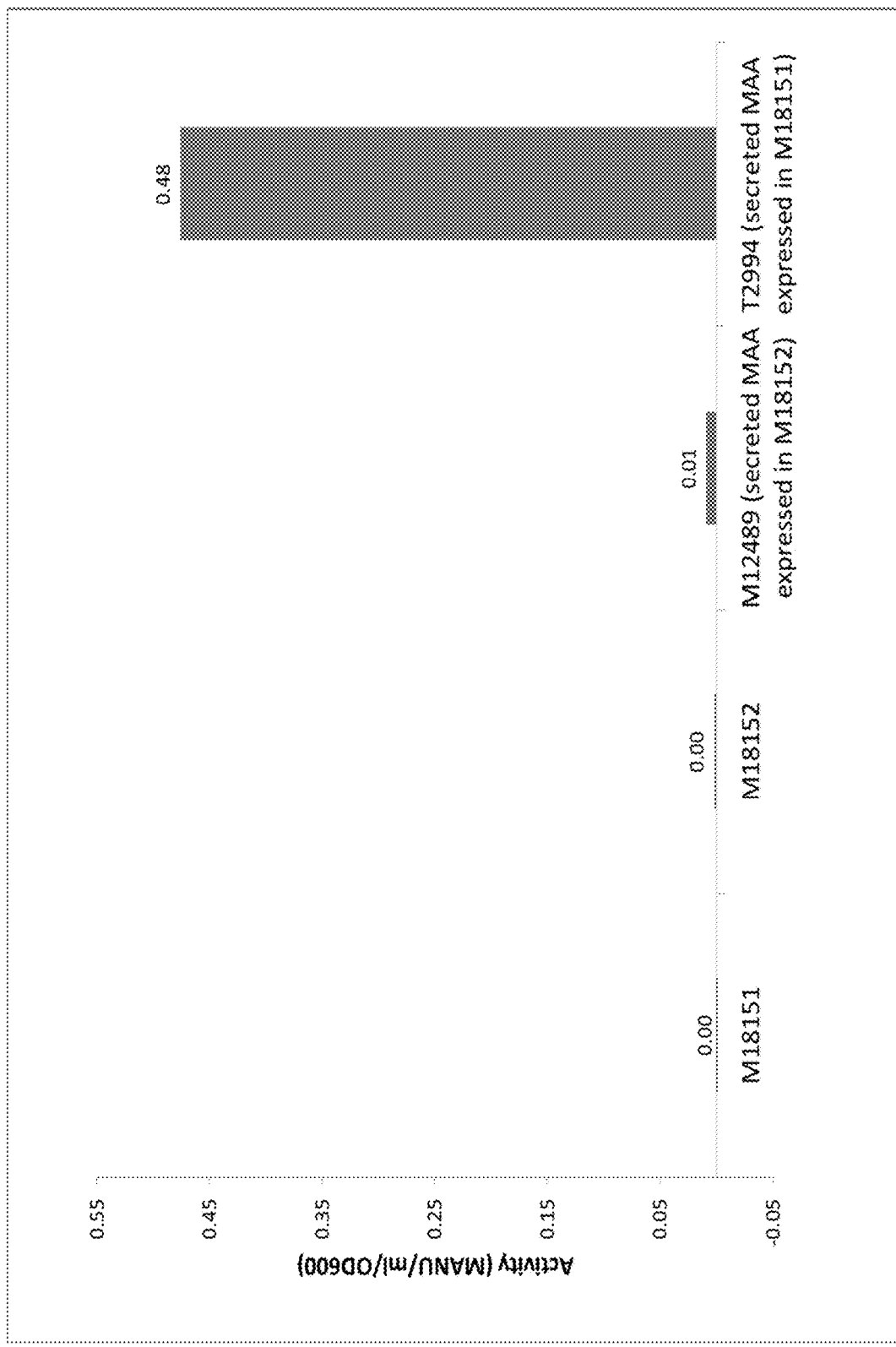
FIG. 1 illustrates the secreted maltogenic amylase activity (MAU/ml/OD$_{600}$) in culture supernatant of wild-type baking strains (M18151 or M18152) or strains expressing a maltogenic alpha-amylase from equivalent genetic cassettes in either M18151 or M18152 baking strain backgrounds. Results are shown as maltogenic alpha-amylase activity per milliliter and normalized to cell density (OD$_{600}$) for each strain tested.

The present disclosure concerns yeast host cell engineered to express an heterologous protein (such as an heterologous enzyme) and which is capable of achieving increased yield and/or biological activity of the expressed heterologous protein. As used in the context of the present disclosure, a recombinant yeast host cell exhibiting "an increased yield in the level of expressed heterologous protein" refers to a recombinant yeast host cell capable of producing a higher amount of the heterologous protein per cell when compared to the level of the heterologous protein expressed in a corresponding control host cell modified in the same manner (with respect to the expression of the heterologous protein) as the recombinant yeast host cell. As used in the context of the present disclosure, a recombinant yeast host cell exhibiting "an increased biological activity of the expressed heterologous protein" refers to a recombinant yeast host cell capable of exhibiting increased biological activity for the heterologous protein per cell when compared to the level of biological activity observed in a corresponding control host cell modified in the same manner (with respect to the expression of the heterologous protein) as the recombinant yeast host cell. When the heterologous protein is an enzyme, a recombinant yeast host cell exhibiting "an increased biological activity of the expressed heterologous protein" refers to a recombinant yeast host cell capable of producing an increased total activity per cell for the heterologous enzyme when compared to the level of total activity observed in a corresponding control host cell modified in the same manner (with respect to the expression of the heterologous protein) as the recombinant yeast host cell.

The recombinant host cell of the present disclosure is a yeast as it can be used in both fed batch and continuous fermentations for enzyme production, can use a simple substrate and, as shown herein, can achieve high yield (increase amount of heterologous protein per cell) and/or biological activity of the heterologous protein. One embodiment of the recombinant yeast host cell is from the species *Saccharomyces cerevisiae*. *S. cerevisiae* is not typically an industrial producer of heterologous proteins such as enzymes because it often lags behind other hosts in terms of the enzyme titer that can be achieved. *S. cerevisiae*, however, has many attributes that would make it a desirable host for production of enzymes for food, feed, and other industries, if it were able to produce high levels of enzyme. *S. cerevisiae* is a generally recognized as safe (GRAS) organism with a long history of safe use in food. Fractions of yeast or whole yeast cells, live or inactivated, are often used as ingredients and processing aids, so any carryover from enzyme production and purification will be considered safe. Yeasts have also long been used as a model organism for scientific research, so it is an extremely well-studied organism and has an extensive depth of genetic tools, and now genomics resources, available. *S. cerevisiae* is able to grow on inexpensive substrates (e.g., molasses) and has a relatively short fermentation time, making contamination control easier.

Recombinant Yeast Host Cell

The present disclosure concerns recombinant yeast host cells that have been genetically engineered. The genetic modification(s) is(are) aimed at increasing the expression of a specific targeted gene (which is considered heterologous to the yeast host cell) and can be made in one or multiple (e.g., 1, 2, 3, 4, 5, 6, 7, 8 or more) genetic locations. In the context of the present disclosure, when recombinant yeast cell is qualified as being "genetically engineered", it is understood to mean that it has been manipulated to add at least one or more heterologous or exogenous nucleic acid residue. In some embodiments, the one or more nucleic acid residues that are added can be derived from an heterologous cell or the recombinant host cell itself. In the latter scenario, the nucleic acid residue(s) is (are) added at one or more genomic location which is different than the native genomic location. The genetic manipulations did not occur in nature and are the results of in vitro manipulations of the yeast.

The genetic modifications in the recombinant yeast host cell of the present disclosure comprise, consist essentially of or consist of a first genetic modification for expression of the an heterologous polypeptide and, optionally a second genetic modification for altering the intracellular cyclic AMP signaling pathway. In the context of the present disclosure, the expression "the genetic modifications in the recombinant yeast host consist essentially of a first genetic modification for expression of the heterologous polypeptide and a second genetic modification for altering the intracellular cyclic AMP signaling pathway" refers to the fact that the recombinant yeast host cell can include other genetic modifications which are unrelated to the heterologous protein production or the alteration of the intracellular cyclic AMP signaling pathway.

When expressed in recombinant yeast host cells, the heterologous proteins described herein are encoded on one or more heterologous nucleic acid molecules. The term "heterologous" when used in reference to a nucleic acid molecule (such as a promoter, a terminator or a coding sequence) or a protein refers to a nucleic acid molecule or a protein that is not natively found in the recombinant host cell. "Heterologous" also includes a native coding region/promoter/terminator, or portion thereof, that was removed from the source organism and subsequently reintroduced into the source organism in a form that is different from the corresponding native gene, e.g., not in its natural location in the organism's genome. The heterologous nucleic acid molecule is purposively introduced into the recombinant host cell. For example, a heterologous element could be derived from a different strain of host cell, or from an organism of a different taxonomic group (e.g., different kingdom, phylum, class, order, family genus, or species, or any subgroup within one of these classifications).

The heterologous nucleic acid molecule present in the recombinant host cell can be integrated in the host cell's genome. The term "integrated" as used herein refers to genetic elements that are placed, through molecular biology techniques, into the genome of a host cell. For example, genetic elements can be placed into the chromosomes of the host cell as opposed to in a vector such as a plasmid carried by the host cell. Methods for integrating genetic elements into the genome of a host cell are well known in the art and include homologous recombination. The heterologous nucleic acid molecule can be present in one or more copies (e.g., 2, 3, 4, 5, 6, 7, 8 or even more copies) in the yeast host cell's genome. Alternatively, the heterologous nucleic acid molecule can be independently replicating from the yeast's genome. In such embodiment, the nucleic acid molecule can be stable and self-replicating.

Suitable yeast host cells that can be used in the context of the present disclosure can be, for example, from the genus *Saccharomyces, Kluyveromyces, Arxula, Debaryomyces,*

*Candida, Pichia, Phaffia, Schizosaccharomyces, Hansenula, Kloeckera, Schwanniomyces, Torula* or *Yarrowia*. Suitable yeast species can include, for example, *S. cerevisiae, S. bulderi, S. barnetti, S. exiguus, S. uvarum, S. diastaticus, C. utilis, K. lactis, K. marxianus* or *K. fragilis*. In some embodiments, the yeast is selected from the group consisting of *Saccharomyces cerevisiae, Schizzosaccharomyces pombe, Candida albicans, Pichia pastoris, Pichia stipitis, Yarrowia lipolytica, Hansenula polymorpha, Phaffia rhodozyma, Candida utilis, Arxula adeninivorans, Debaryomyces hansenii, Debaryomyces polymorphus, Schizosaccharomyces pombe* and *Schwanniomyces occidentalis*. In one particular embodiment, the yeast is *Saccharomyces cerevisiae*. In some embodiments, the host cell can be an oleaginous yeast cell. For example, the oleaginous yeast host cell can be from the genus *Blakeslea, Candida, Cryptococcus, Cunninghamella, Lipomyces, Mortierella, Mucor, Phycomyces, Pythium, Rhodosporidum, Rhodotorula, Trichosporon* or *Yarrowia*. In some alternative embodiment, the host cell can be an oleaginous microalgae host cell (e.g., for example, from the genus *Thraustochytrium* or *Schizochytrium*). In an embodiment, the recombinant yeast host cell is from the genus *Saccharomyces* and, in some embodiments, from the species *Saccharomyces cerevisiae*.

The recombinant yeast host cells of the present disclosure include a first heterologous nucleic acid molecule intended to allow the expression (e.g., encoding) of one or more heterologous proteins. In an embodiment, the heterologous protein is an heterologous enzyme. In the context of the present application, the heterologous enzyme can be, without limitation, an heterologous oxidoreductase, an heterologous transferase, an heterologous hydrolase, an heterologous lyase, an heterologous isomerase, an heterologous phosphatase and/or an heterologous ligase.

As used in the context of the present disclosure, the expression "oxidoreductase" (also referred to as an oxidase, E.C. 1) refers to a protein having enzymatic activity and capable of catalyzing the transfer of electrons from one molecule (the reductant or the electron donor) to another (the oxidant or the electron acceptor). In an embodiment, the oxidoreductase is a hexose oxidase (E.C. 1.1.3.5), for example, the hexose oxidase can be a glucose oxidase (E.C. 1.1.3.4). In some embodiments, oxidases (such as glucose oxidases) can improve dough machinability. In an embodiment, the one or more oxidoreductases is a glucose oxidase from *Aspergillus niger*. Oxidoreductases can be used in fermentation processes for making biofuels, distilling products, wine, beer and yeast-leavened bakery products. Oxidoreductases can be used for making food and beverages (e.g., non-yeast-leavened (chemically-leavened) bakery products), feed or other industrial products (e.g., detergents, textiles, leather, pulp and paper, oil and gas and/or biopolymers).

As used in the context of the present disclosure, the expression "transferase" (E.C. 2) refers to a protein having enzymatic activity and capable of catalyzing the transfer of specific functional groups (e.g., a methyl or glycosyl group for example) from one molecule (called the donor) to another (called the acceptor). For example, the transferases can be acyltransferases (E.C. 2.3 such as transglutaminases (E.C. 2.3.2.13) for example) or glycosyltransferases (E.C. 2.4 such as amylomaltases (E.C. 2.4.1.3) for example). A transglutaminase can be used in baking goods to improve dough strength.

As used in the context of the present disclosure, the expression "lyase" (E.C. 4) refers to a protein having enzymatic activity and capable of catalyzing the elimination of various chemical bonds by means other than hydrolysis (e.g., a "substitution" reaction) and oxidation. For example, the lyase can be a malolactic enzyme (EC 4.1.1.101), Acetolactate decarboxylase (or, alpha-acetolactate decarboxylase, EC 4.1.1.5) and/or a pectate lyase (E.C. 4.2.2.2). Lyases can be used in fermentation processes for making biofuels, distilling products, wine, beer and yeast-leavened bakery products. Lyases can also be used for making food and beverages (e.g., non-yeast-leavened (chemically-leavened) bakery products), feed or other industrial products (e.g., detergents, textiles, leather, pulp and paper, oil and gas and/or biopolymers).

As used in the context of the present disclosure, the expression "isomerase" (E.C. 5) refers to a protein having enzymatic activity and capable of catalyzing the conversion a molecule from one isomer to another. For example, the isomerase can be a glucose isomerase (E.C. 5.1.3) or xylose isomerase (EC 5.1.3.5). Isomerases can be used in fermentation processes for making biofuels, distilling products, wine, beer and yeast-leavened bakery products. Isomerases can also be used for making food and beverages (e.g., non-yeast-leavened (chemically-leavened) bakery products), feed or other industrial products (e.g., detergents, textiles, leather, pulp and paper, oil and gas and/or biopolymers).

As used in the context of the present disclosure, the expression "ligase" (E.C. 6) refers to a protein having enzymatic activity and capable of catalyzing the joining of two molecules by forming a new chemical bond. For example, the ligase can be an urea amidolyase (E.C. EC 6.3.4.6). Ligases can be used in fermentation processes for making biofuels, distilling products, wine, beer and yeast-leavened bakery products. Ligases can also be used for making food and beverages (e.g., non-yeast-leavened (chemically-leavened) bakery products), feed or other industrial products (e.g., detergents, textiles, leather, pulp and paper, oil and gas and/or biopolymers).

As used in the context of the present disclosure, the expression "hydrolase" (E.C. 3) refers to a protein having enzymatic activity and capable of catalyzing the hydrolysis of a chemical bound. For example, the hydrolase can be an esterase (E.C. 3.1 for example lipase, phospholipase A1 and/or phospholipase A2), can cleaved C—N non-peptide bonds (E.C. 3.5 for example an asparaginase), can be a glycosylase (E.C. 3.2 for example an amylase (E.C. 3.2.1.1), a glucanase, a glycosidase (E.C. 3.2.1), a cellulase (E.C. 3.2.1.4)), a pectinase and/or a lactase (E.C. 3.2.1.108)), a protease (E.C. 3.4 for example a bacterial protease, a plant protease or a fungal protease). When the hydrolase is an amylase, it can be, for example, a fungal alpha amylase, a bacterial alpha amylase, a maltogenic alpha amylase, a maltotetrahydrolase, a plant (e.g., barley) alpha or beta amylase and/or a glucoamylase. When the hydrolase is a glycosidase, it can be, for example, a beta glucosidase. When the hydrolase is a cellulase, it can be, for example, a cellulase, an hemicellulase and/or a xylanase.

As used herein, the expression "phosphatase" refers to a protein having enzymatic activity and capable, in the presence of water, of catalyzing the cleavage of a phosphoric acid monoester into a phosphate ion and an alcohol. An embodiment of a phosphatase is a phytase, a protein having enzymatic activity and capable of catalyzing the hydrolysis of phytic acid (myo-inositol hexakisphosphate) into inorganic phosphorus. There are four distinct classes of phytase: histidine acid phosphatases (HAPS), β-propeller phytases, purple acid phosphatases and protein tyrosine phosphatase-like phytases (PTP-like phytases). Phytic acid has six phosphate groups that may be released by phytases at different rates and in different order. Phytases hydrolyze phosphates from phytic acid in a stepwise manner, yielding products that again become substrates for further hydrolysis. Phytases have been grouped based on the first phosphate position of phytic acid that is hydrolyzed: are 3-phytase (EC 3.1.3.8), 4-phytase (EC 3.1.3.26) and 5-phytase (EC 3.1.3.72). In an embodiment, the phytase is derived from a bacterial species, such as, for example, a *Citrobacter* sp. or an *Escherichia* sp. In a specific embodiment, the heterologous phytase is derived from a *Citrobacter* sp., such as for example *Citrobacter braakii*, a variant thereof or a fragment thereof. In another embodiment, the heterologous phytase is derived from an *Escherichia* sp., such as, for example, *Escherichia coli*, a variant thereof or a fragment thereof.

As used herein, the expression "amylolytic enzyme" refers to a class of enzymes capable of hydrolyzing starch or hydrolyzed starch. Amylolytic enzymes include, but are not limited to alpha-amylases (EC 3.2.1.1, sometimes referred to fungal alpha-amylase, see below), maltogenic amylase (EC 3.2.1.133), glucoamylase (EC 3.2.1.3), glucan 1,4-alpha-maltotetraohydrolase (EC 3.2.1.60), pullulanase (EC 3.2.1.41), iso-amylase (EC 3.2.1.68) and amylomaltase (EC 2.4.1.25). In an embodiment, the one or more amylolytic enzymes can be an alpha-amylase from *Aspergillus oryzae*, a maltogenic alpha-amylase from *Geobacillus stearothermophilus* (and have, for example, the amino acid sequence of SEQ ID NO: 3, a variant thereof or a fragment thereof), an alpha-amylase from *Pyrococcus furiosus* (and have, for example, the amino acid sequence of SEQ ID NO: 4), a glucoamylase from *Saccharomycopsis fibuligera*, a glucan 1,4-alpha-maltotetraohydrolase from *Pseudomonas*, a pullulanase from *Bacillus naganoensis*, a pullulanase from *Bacillus acidopullulyticus*, an iso-amylase from *Pseudomonas amyloderamosa* and/or amylomaltase from *Thermus thermophilus*.

As used herein, the expression "cellulase/hemi-cellulase" refers to a class of enzymes capable of hydrolyzing, respectively, cellulose or hemi-cellulose. Cellulases/hemi-cellulases include, but are not limited to a cellulase (E.C. 3.2.1.4) and an endoB(1,4)D-xylanase (E.C. 3.2.1.8). In an embodiment, the one or more cellulase/hemi-cellulase can be a cellulase from *Penicillium funiculosum* and/or an endoB(1,4)D-xylanase from Rasamsonia *emersonii*.

As used herein, the expression "lipase" refers to a class of enzymes capable of hydrolyzing lipids. In an embodiment, the one or more lipase can be a triacylglycerol lipase from *Thermomyces lanuginosis*, a phospholipase A2 from *Sus scrofa*, a phospholipase A2 from *Streptomyces vialaceoruber* and/or a phospholipase A2 from *Aspergillus oryzea*.

As used in the present disclosure, the term "maltogenic amylase" refers to a polypeptide capable of hydrolyzing starch or hydrolyzed starch into maltose. Maltogenic amylases include, but are not limited to fungal alpha-amylases (derived, for example, from *Aspergillus* sp. (e.g., *A. Niger*, *A. kawachi* and *A. oryzae*); *Trichoderma* sp. (e.g., *T. reesie*), *Rhisopus* sp., *Mucor* sp. and *Penicillium* sp.), acid stable fungal amylase (derived, for example, from *Aspergillus niger*), β-amylases (derived, for example, from plant (wheat, barley, rye, shorgum, soy, sweet potato, rice) and/or microorganisms (*Bacillus cereus, Bacillus polymixa, Bacillus megaterium, Arabidopsis thaliana*), maltogenic amylases (E.C.3.2.1.133) (derived, for example, from microorganisms such as *Bacillus subtilis, Geobacillus stearothermophilus, Bacillus thermoalkalophilus, Lactobacillus gasseri, Thermus* sp.). In a specific embodiment, the recombinant yeast host cells of the present disclosure include an heterologous nucleic acid molecule coding for the heterologous maltogenic amylase derived from *Geobacillus stearothermophilus*.

The heterologous protein can be a variant of a known/native protein. A variant comprises at least one amino acid difference when compared to the amino acid sequence of the native/know protein. As used herein, a variant refers to alterations in the amino acid sequence that do not adversely affect the biological functions of the heterologous protein. A substitution, insertion or deletion is said to adversely affect the protein when the altered sequence prevents or disrupts a biological function associated with the heterologous protein. For example, the overall charge, structure or hydrophobic-hydrophilic properties of the protein can be altered without adversely affecting a biological activity. Accordingly, the amino acid sequence can be altered, for example to render the peptide more hydrophobic or hydrophilic, without adversely affecting the biological activities of the heterologous protein. The protein variants have at least 50%, 55%, 60%, 65%, 70%, 75%, 80%, 85%, 90%, 95%, 96%, 97%, 98% or 99% identity to the heterologous protein described herein. The term "percent identity", as known in the art, is a relationship between two or more polypeptide sequences or two or more polynucleotide sequences, as determined by comparing the sequences. The level of identity can be determined conventionally using known computer programs. Identity can be readily calculated by known methods, including but not limited to those described in: Computational Molecular Biology (Lesk, A. M., ed.) Oxford University Press, N Y (1988); Biocomputing: Informatics and Genome Projects (Smith, D. W., ed.) Academic Press, N Y (1993); Computer Analysis of Sequence Data, Part I (Griffin, A. M., and Griffin, H. G., eds.) Humana Press, N J (1994); Sequence Analysis in Molecular Biology (von Heinje, G., ed.) Academic Press (1987); and Sequence Analysis Primer (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PEN ALT Y=10). Default parameters for pairwise alignments using the Clustal method were KTUPLB 1, GAP PENALTY=3, WINDOW=5 and DIAGONALS SAVED=5.

The variant heterologous protein described herein may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide for purification of the polypeptide. A "variant" of the heterologous protein can be a conservative variant or an allelic variant.

The heterologous protein can be a fragment of a known/native protein or fragment of a variant of a known/native protein. In an embodiment, the fragment corresponds to the known/native protein to which the signal peptide sequence has been removed. In some embodiments, heterologous protein "fragments" have at least at least 100, 200, 300, 400, 500, 600, 700, 800, 900 or more consecutive amino acids of the heterologous protein. A fragment comprises at least one less amino acid residue when compared to the amino acid sequence of the known/native heterologous protein and still possess the enzymatic activity of the full-length heterologous protein. In an embodiment, the fragment corresponds to the amino acid sequence of the protein lacking the signal peptide. In some embodiments, fragments of the heterologous protein can be employed for producing the corresponding full-length heterologous by peptide synthesis. Therefore, the fragments can be employed as intermediates for producing the full-length proteins.

In the recombinant yeast host cell of the present disclosure, the heterologous protein can be physically associated or not with the recombinant yeast host cell. In an embodiment, the heterologous protein is secreted and, upon its secretion, becomes physically dissociated from the recombinant yeast host cell.

In another embodiment, the heterologous protein remains associated with the recombinant yeast host cell (e.g., is "cell-associated") once it has been expressed. In such embodiment, the heterologous protein can be expressed inside the recombinant yeast host cell (intracellularly). In such embodiment, the heterologous protein does not need to be associated to the recombinant yeast host cell's wall. When the heterologous protein is intended to be expressed intracellularly, its signal sequence, if present in the native sequence, can be deleted to allow intracellular expression.

In another embodiment of a cell-associated heterologous protein, it can be secreted upon expression, but when it is, it must remain physically associated with the recombinant yeast host cell. In an embodiment, at least one portion (usually at least one terminus) of the heterologous protein is bound, covalently, non-covalently and/or electrostatically for example, to cell wall (and in some embodiments to the cytoplasmic membrane). For example, the heterologous protein can be modified to bear one or more transmembrane domains, to have one or more lipid modifications (myristoylation, palmitoylation, farnesylation and/or prenylation), to interact with one or more membrane-associated protein and/or to interactions with the cellular lipid rafts. While the heterologous protein may not be directly bound to the cell membrane or cell wall (e.g., such as when binding occurs via a tethering moiety), the protein is nonetheless considered a "cell-associated" heterologous protein according to the present disclosure.

In some additional cell association embodiments, the heterologous protein can be expressed to be located at and associated to the cell wall of the recombinant yeast host cell. In some embodiments, the heterologous protein is expressed to be located at and associated to the external surface of the cell wall of the host cell. Recombinant yeast host cells all have a cell wall (which includes a cytoplasmic membrane) defining the intracellular (e.g., internally-facing the nucleus) and extracellular (e.g., externally-facing) environments. The heterologous protein can be located at (and in some embodiments, physically associated to) the external face of the recombinant yeast host's cell wall and, in further embodiments, to the external face of the recombinant yeast host's cytoplasmic membrane. In the context of the present disclosure, the expression "associated to the external face of the cell wall/cytoplasmic membrane of the recombinant yeast host cell" refers to the ability of the heterologous protein to physically integrate (in a covalent or non-covalent fashion), at least in part, in the cell wall (and in some embodiments in the cytoplasmic membrane) of the recombinant yeast host cell. The physical integration can be attributed to the presence of, for example, a transmembrane domain on the heterologous protein, a domain capable of interacting with a cytoplasmic membrane protein on the heterologous protein, a post-translational modification made to the heterologous protein (e.g., lipidation), etc.

Some heterologous proteins have the intrinsic ability to locate at and associate to the cell wall of a recombinant yeast host cell (e.g., being cell-associated). One example of an heterologous protein having the intrinsic ability of being cell-associated is the maltogenic alpha-amylase of Geobacillus stearothermophilus expressed in S. cerevisiae in the absence of a tethering moiety and clearly show that this heterologous protein is intrinsically "cell-associated" and exhibits enzymatic activity (e.g., maltogenic alpha-amylase activity).

However, in some circumstances, it may be warranted to increase or provide cell association to some heterologous proteins because they exhibit insufficient intrinsic cell association or simply lack intrinsic cell association. In such embodiment, it is possible to provide the heterologous protein as a chimeric construct by combining it with a tethering amino acid moiety which will provide or increase attachment to the cell wall of the recombinant yeast host cell. In such embodiment, the chimeric heterologous protein will be considered "tethered". It is preferred that the amino acid tethering moiety of the chimeric protein be neutral with respect to the biological activity of the heterologous protein, e.g., does not interfere with the biological activity (such as, for example, the enzymatic activity) of the heterologous protein. In some embodiments, the association of the amino acid tethering moiety with the heterologous protein can increase the biological activity of the heterologous protein (when compared to the non-tethered, "free" form). The tethering moiety can be a transmembrane domain found on another protein and allow the chimeric protein to have a transmembrane domain. Alternatively, the tethering moiety can be modified post-translation to include a glycosylphosphatidylinositol (GPI) anchor and allow the chimeric protein to have a GPI anchor. The tethering moiety may be directly associated with the heterologous protein or be indirectly associated by the use of a linker. Exemplary tethering moieties have been disclosed in PCT/IB2018/051671 (incorporate herewith in its entirety) and can be used to provide the heterologous protein of the present disclosure in a tethered form.

The recombinant yeast host cell can be derived from an ancestral yeast host cell having an altered intracellular cyclic AMP signaling pathway or of exhibiting a constitutive elevated level of intracellular cyclic AMP (cAMP). The intracellular production of cAMP is usually inducible in response to glucose addition to glucose starved yeast or yeast grown on non-fermentable carbon sources, as well as repletion of nitrogen or phosphorus when cells are starved for each nutrient. Modulation in the levels of intracellular cAMP mediates downstream signaling. As it is shown in the Examples below, yeast cells having an altered intracellular cAMP signaling pathway can be used as host cells to produce more biologically active heterologous proteins per cell. The recombinant yeast host cell of the present disclosure exhibits an "altered" intracellular cyclic AMP signaling pathway (or a "constitutive" elevated intracellular cAMP levels) when their levels of intracellular cAMP are not substantially modified in the presence of a cAMP stimulus known to stimulate intracellular cAMP production in a control cell (e.g., glucose, nitrogen and/or phosphorus when the yeast host cell is placed in glucose, nitrogen and/or phosphorus depletion conditions). The recombinant yeast host cell of the present disclosure is understood to exhibit an altered intracellular cAMP signaling pathway (or a constitutive "elevated" intracellular cAMP levels) when compared to a control yeast host cell placed in a corresponding condition. For example, when placed in the presence and absence of a cAMP stimulus (glucose, nitrogen or phosphorus), the selected ancestral or the recombinant yeast host cell of the present disclosure does not exhibit in a substantial difference in intracellular cAMP levels in contrast to the control yeast cell (which would exhibit increased intracellular cAMP levels in the presence of the cAMP stimulus).

In an embodiment, the ability of the recombinant yeast host cell to exhibit an altered intracellular cAMP signaling (or a constitutive intracellular cAMP level) can be native to the recombinant yeast host cell (e.g., it can be the results of a wild-type mutation that was not genetically introduced into the recombinant yeast host cell). Exemplary recombinant yeast host cell having such native ability include, but are not limited to biological deposit PTA-125175 (also referred to herewith to M18151, deposited on at the American Type Culture Collection on Jul. 25, 2018), biological deposit PTA-125177 (also referred to herewith as M18195, deposited on at the American Type Culture Collection on Jul. 25, 2018) or a yeast cell having the characteristics of the biological deposit PTA-125175 or PTA-125177.

In another embodiment, the ability of the recombinant yeast host cell to exhibit an altered intracellular cAMP signaling (or a constitutive intracellular cAMP level) is provided by the genetic modification of the recombinant yeast host cell (that can be introduced prior to or after the first genetic modification). For example, it is possible to inactivate a protein involved in the breakdown of cAMP (for example by removing one or more nucleic acid residues in a gene coding for a protein involved in the catabolism of cAMP). This could also be achieved by inactivating or downregulating the protein repressors of the cAMP pathway (IRA1 and/or IRA2 for example) and/or expressing constitutively active forms of RAS1 and/or RAS2.

Alternatively or in combination, it is possible to introduce of at least a second heterologous nucleic acid molecule which can encode a non-coding sequence (such as a promoter) or a coding sequence (such as one encoding a protein) which provides such activity. Exemplary embodiments of the second heterologous nucleic acid molecule include those of the promoters of gene encoding proteins capable of producing intracellular cAMP, such as, for example, an adenylate cyclase, those encoding proteins capable of producing intracellular cAMP, such as, for example, an adenylate cyclase as well as those encoding proteins regulating the activity of proteins capable of producing intracellular cAMP, such as, for example, an adenylate cyclase. In an embodiment, the second heterologous nucleic acid molecule can be, for example, a constitutive promoter intended to regulate the expression of a native or heterologous protein capable of producing intracellular cAMP, such as, for example, an adenylate cyclase. In another embodiment, the second heterologous nucleic acid molecule can be, for example, an heterologous protein capable of producing intracellular cAMP, such as, for example, an adenylate cyclase.

In yeasts, and specifically in *Saccharomyces cerevisiae*, the adenylate cyclase protein is encoded by the CYR1 gene. The ancestral yeast host cell can have a native CYR1 gene which is a variant CYR1 gene. Alternatively or in combination, the recombinant yeast host cell can have or be genetically modified to bear a variant CYR1 gene encoding a CYR1 protein which is constitutively expressed. The recombinant yeast host cell can further be modified to inactive or remove the gene(s) encoding the native adenylate cyclase. In still another example, the second nucleic acid molecule can include a gene encoding a protein capable of increasing the activity of adenylate cyclase and/or decreasing the activity of an inhibitor of adenylate cyclase.

In embodiments in which the recombinant yeast host cell bears a variant CYR1 gene encoding a variant CYR1 protein allowing the constitutive elevated expression of intracellular cAMP. For example, the variant CYR1 gene can include one or more genetic modifications (e.g., insertion, addition and/or modification of at least one nucleic acid residue) when compared to the wild-type CYR1 gene either located in its non-coding and/or coding sequence. The genetic modification can be, for example, a single polymorphic nucleotide (SNP) in the variant CYR1 gene. The genetic modification can lead to the presence of one or more variations (e.g., insertion, addition and/or modification of at least one amino acid residue) in the amino acid sequence of the variant CYR1 protein. The at least one variations may be located in the leucine rich repeats region of the protein (and in some embodiments altering its ability to bind to the Ras protein) and/or in the phosphatase region of the protein (and in some embodiments, altering its ability to remove phosphate moieties from its substrate).

In embodiments in which the wild-type (reference) CYR1 gene has the nucleic acid sequence of SEQ ID NO: 1, the variant CYR1 gene can include one or more SNP at the following corresponding positions: 772 or 2480. In some embodiments, the variant CYR1 gene can include the following two or more SNPs at positions corresponding to 772 and 2480. For example, the variant CYR1 gene can have, at a position corresponding to position 772 of SEQ ID NO: 1 another nucleic acid base than G (A for example). In another example, the variant CYR1 gene can have, at a position corresponding to position 2480 of SEQ ID NO: 1, another nucleic acid base than C (T for example). In some embodiments, the variant CYR1 gene can have, at a position corresponding to position 772 of SEQ ID NO: 1, another nucleic acid base than G (A for example) and, at a position corresponding to position 2480 of SEQ ID NO: 1, another nucleic acid base than C (T for example). In some embodiments, the variant CYR1 gene can have the nucleic acid sequence of SEQ ID NO: 5.

In embodiments in which the wild-type (reference) CYR1 gene has the nucleic acid sequence of SEQ ID NO: 7, the variant CYR1 gene can include one or more SNP at positions corresponding to 772, 2504, 2605 or 4305. In some embodiments, the variant CYR1 gene can include two or more SNPs at the positions corresponding to 772, 2504, 2605 and/or 4305. In additional embodiments, the variant CYR1 gene can include three or more SNPs at the positions corresponding to positions 772, 2504, 2605 and/or 4305. In some further embodiments, the variant CYR1 gene can include four or more SNPs at the following positions: 772, 2504, 2605 and 4305. For example, the variant CYR1 gene can have, at a position corresponding to position 772 of SEQ ID NO: 7, another nucleic acid base than G (A for example). In another example, the variant CYR1 gene can have, at a position corresponding to position 2504 of SEQ ID NO: 7, another nucleic acid base than C (T for example). In still another example, the variant CYR1 gene can have, at a position corresponding to position 2605 of SEQ ID NO: 7, a nucleic acid based other than G (A for example). In yet a further example, the variant CYR1 gene can have, at a position corresponding to position 4305 of SEQ ID NO: 7, another nucleic acid base than C (A for example). In an embodiment, the variant CYR1 gene can have, at a position corresponding to position 772 of SEQ ID NO: 7, another nucleic acid base than G (A for example) and at a position corresponding to position 2504 of SEQ ID NO: 7, another nucleic acid base than C (T for example). In an embodiment, the variant CYR1 gene can have, at a position corresponding to position 772 of SEQ ID NO: 7, another nucleic acid base than G (A for example) and at a position corresponding to position 2605 of SEQ ID NO: 7, a nucleic acid based other than G (A for example). In an embodiment, the variant CYR1 gene can have, at a position corresponding to position 772 of SEQ ID NO: 7, another nucleic acid base than G (A for example) and at a position corresponding to position 4305 of SEQ ID NO: 7, another nucleic acid base than C (A for example). In an embodiment, the variant CYR1 gene can have, at a position corresponding to position 2504 of SEQ ID NO: 7, another nucleic acid base than C (T for example) and at a position corresponding to position 2605 of SEQ ID NO: 7, a nucleic acid based other than G (A for example). In an embodiment, the variant CYR1 gene can have, at a position corresponding to position 2504 of SEQ ID NO: 7, another nucleic acid base than C (T for example) and at a position corresponding to position 4305 of SEQ ID NO: 7, another nucleic acid base than C (A for example). In still another embodiment, the variant CYR1 gene can have, at a position corresponding to position 2605 of SEQ ID NO: 7, a nucleic acid based other than G (A for example) and at a position corresponding to position 4305 of SEQ ID NO: 7, another nucleic acid base than C (A for example). In an embodiment, the variant CYR1 gene can have, at a position corresponding to position 772 of SEQ ID NO: 7, another nucleic acid base than G (A for example), at a position corresponding to position 2504 of SEQ ID NO: 7, another nucleic acid base than C (T for example) and at a position corresponding to position 2605 of SEQ ID NO: 7, a nucleic acid based other than G (A for example). In an embodiment, the variant CYR1 gene can have, at a position corresponding to position 2504 of SEQ ID NO: 7, another nucleic acid base than C (T for example), at a position corresponding to position 2605 of SEQ ID NO: 7, a nucleic acid based other than G (A for example) and at a position corresponding to position 4305 of SEQ ID NO: 7, another nucleic acid base than C (A for example). In an embodiment, the variant CYR1 gene can have, at a position corresponding to position 772 of SEQ ID NO: 7, another nucleic acid base than G (A for example), at a position corresponding to position 2605 of SEQ ID NO: 7, a nucleic acid based other than G (A for example) and at a position corresponding to position 4305 of SEQ ID NO: 7, another nucleic acid base than C (A for example). In an embodiment, the variant CYR1 gene can have, at a position corresponding to position 772 of SEQ ID NO: 7, another nucleic acid base than G (A for example), at a position corresponding to position 2504 of SEQ ID NO: 7, another nucleic acid base than C (T for example), at a position corresponding to position 2605 of SEQ ID NO: 7, a nucleic acid based other than G (A for example) and at a position corresponding to position 4305 of SEQ ID NO: 7, another nucleic acid base than C (A for example). In yet a further example, the variant CYR1 gene can have, at a position corresponding to position 4305 of SEQ ID NO: 7, another nucleic acid base than C (A for example). In an embodiment, the variant CYR1 gene can have, at a position corresponding to position 772 of SEQ ID NO: 7, another nucleic acid base than G (A for example), at a position corresponding to position 2504 of SEQ ID NO: 7, another nucleic acid base than C (T for example), at a position corresponding to position 2605 of SEQ ID NO: 7, a nucleic acid based other than G (A for example) and at a position corresponding to position 4305 of SEQ ID NO: 7, another nucleic acid base than C (A for example). In some embodiments, the variant CYR1 gene can have the nucleic acid sequence of SEQ ID NO: 5.

In embodiments in which the wild-type (reference) CYR1 protein has the amino acid sequence of SEQ ID NO: 2, the variant CYR1 protein can include one or more variations at the following corresponding positions: 258 and 827. In some embodiments, the variant CYR1 protein includes at least two variations at the following corresponding positions: 258 and/or 827. In an example, the variant CYR1 protein could have, at a position corresponding to position 258 of SEQ ID NO: 1, an amino acid residue which is not an alanine residue (a threonine residue for example). In another example, the variant CYR1 protein could have, at a position corresponding to position 835 of SEQ ID NO: 2, an amino acid residue different than an alanine residue (a valine residue for example). In an embodiment, the variant CYR1 protein could have, at a position corresponding to position 258 of SEQ ID NO: 1, an amino acid residue which is not an alanine residue (a threonine residue for example) and at a position corresponding to position 835 of SEQ ID NO: 2, an amino acid residue different than an alanine residue (a valine residue for example). In another embodiment, the variant CYR1 protein can have the amino acid sequence of SEQ ID NO: 6.

In embodiments in which the wild-type (reference) CYR1 protein has the amino acid sequence of SEQ ID NO: 8, the variant CYR1 protein can include one or more variations at the following corresponding positions: 258 835, 869 and/or 1435. In some embodiments, the variant CYR1 protein includes at least two variations at the following corresponding positions: 258 835, 869 and/or 1435. In some additional embodiments, the variant CYR1 protein includes at least three variations at the following positions: 258, 835, 869 and/or 1435. In still further embodiments, the variant CYR1 protein includes at least four variations at the following positions: 258, 835, 869 and 1435. In an example, the variant CYR1 protein could have, at position 258 of SEQ ID NO: 8, an amino acid residue which is not an alanine residue (a threonine residue for example). In another example, the variant CYR1 protein could have, at position 835 of SEQ ID NO: 8, an amino acid residue which is not an alanine residue (a valine residue for example). In a further example, the variant CYR1 protein could have, at position 869 of SEQ ID NO: 8, an amino acid residue which is not a glutamic acid residue (a lysine residue for example). In yet another example, the variant CYR1 protein could have, at position 1435 of SEQ ID NO: 8, an amino acid residue which is different from an aspartic acid residue (a glutamic acid residue for example). In an example, the variant CYR1 protein could have, at position 258 of SEQ ID NO: 8, an amino acid residue which is not an alanine residue (a threonine residue for example) and at position 835 of SEQ ID NO: 8, an amino acid residue which is not an alanine residue (a valine residue for example). In an example, the variant CYR1 protein could have, at position 258 of SEQ ID NO: 8, an amino acid residue which is not an alanine residue (a threonine residue for example) and at position 869 of SEQ ID NO: 8, an amino acid residue which is not a glutamic acid residue (a lysine residue for example). In an example, the variant CYR1 protein could have, at position 258 of SEQ ID NO: 8, an amino acid residue which is not an alanine residue (a threonine residue for example) and, at position 1435 of SEQ ID NO: 8, an amino acid residue which is different from an aspartic acid residue (a glutamic acid residue for example). In another example, the variant CYR1 protein could have, at position 835 of SEQ ID NO: 8, an amino acid residue which is not an alanine residue (a valine residue for example) and, at position 869 of SEQ ID NO: 8, an amino acid residue which is not a glutamic acid residue (a lysine residue for example). In another example, the variant CYR1 protein could have, at position 835 of SEQ ID NO: 8, an amino acid residue which is not an alanine residue (a valine residue for example) and, at position 1435 of SEQ ID NO: 8, an amino acid residue which is different from an aspartic acid residue (a glutamic acid residue for example). In an example, the variant CYR1 protein could have, at position 258 of SEQ ID NO: 8, an amino acid residue which is not an alanine residue (a threonine residue for example), at position 835 of SEQ ID NO: 8, an amino acid residue which is not an alanine residue (a valine residue for example) and, at position 869 of SEQ ID NO: 8, an amino acid residue which is not a glutamic acid residue (a lysine residue for example). In an example, the variant CYR1 protein could have, at position 258 of SEQ ID NO: 8, an amino acid residue which is not an alanine residue (a threonine residue for example). In another example, the variant CYR1 protein could have, at position 835 of SEQ ID NO: 8, an amino acid residue which is not an alanine residue (a valine residue for example) and, at position 1435 of SEQ ID NO: 8, an amino acid residue which is different from an aspartic acid residue (a glutamic acid residue for example). In an example, the variant CYR1 protein could have, at position 258 of SEQ ID NO: 8, an amino acid residue which is not an alanine residue (a threonine residue for example), at position 835 of SEQ ID NO: 8, an amino acid residue which is not an alanine residue (a valine residue for example) and, at position 1435 of SEQ ID NO: 8, an amino acid residue which is different from an aspartic acid residue (a glutamic acid residue for example). In an example, the variant CYR1 protein could have, at position 258 of SEQ ID NO: 8, an amino acid residue which is not an alanine residue (a threonine residue for example). In another example, the variant CYR1 protein could have, at position 835 of SEQ ID NO: 8, an amino acid residue which is not an alanine residue (a valine residue for example), at position 869 of SEQ ID NO: 8, an amino acid residue which is not a glutamic acid residue (a lysine residue for example) and, at position 1435 of SEQ ID NO: 8, an amino acid residue which is different from an aspartic acid residue (a glutamic acid residue for example). In another embodiment, the variant CYR1 protein can have the amino acid sequence of SEQ ID NO: 6.

Optionally, the recombinant yeast host cell can exhibit polyploidy in at least one of its chromosomes. In some embodiments, the recombinant yeast host cell exhibits polyploidy (e.g., triploidy or tetraploidy) in at least one, two, three, four, five, six, seven, eight, nine, ten, eleven, twelve, thirteen, fourteen, fifteen or sixteen chromosomes. In some embodiments, the recombinant yeast host cell exhibits triploidy in at least one, two, three, four, five, six, seven, eight, nine, ten, eleven, twelve, thirteen, fourteen, fifteen or sixteen chromosomes. Alternatively or in combination, the recombinant yeast host cell exhibits tetraploidy in at least one, two, three, four, five, six, seven, eight, nine, ten, eleven, twelve, thirteen, fourteen, fifteen or sixteen chromosomes. In some specific embodiments, the recombinant yeast host cell has a majority of triploid chromosomes. In some further specific embodiments, the recombinant yeast host cell does not have a single haploid or diploid chromosome. In some additional specific embodiments, the recombinant yeast host cell has two tetraploid chromosomes with the remainder of chromosomes triploid.

Method for Making Recombinant Yeast Host Cell

The present disclosure also provides a method for making the recombinant yeast host cell of the present disclosure. The method broadly comprises two steps: a first one in which an ancestral yeast host cell is selected and a second in which the selected ancestral yeast host cell is modified by introducing a first heterologous nucleic acid molecule (coding for the expression of the heterologous protein) to provide the recombinant yeast host cell. The steps of the method can be performed in any order. The selection step can be performed after the introduction step. The introduction step can be performed after the selection step.

In the selection step, an ancestral yeast host cell is chosen if it is shown to exhibit an altered intracellular cAMP signaling (or a constitutive intracellular cAMP level). This can be done, for example, by determining the intracellular level of cAMP in the ancestral yeast host cell in different conditions (in the presence and in the absence of glucose and/or in the presence or absence of nitrogen) to assess if the intracellular level of cAMP is increased or not or if it is constitutive. If the cAMP signaling is altered, the strain is not expected to exhibit an increase in cAMP levels in the presence or the absence of a cAMP stimulus (glucose, nitrogen and/or phosphorus). This can also be done, for example, by comparing the intracellular level of cAMP in the ancestral yeast host cell and in a control host cell in a control condition (e.g., in the presence of glucose and/or the absence of nitrogen or in the absence of glucose and/or in the presence of nitrogen). In such embodiment, the ancestral yeast host cell can be selected on the basis that its intracellular level cAMP is higher than the intracellular level of cAMP of the control yeast host cell. In some embodiments, the control yeast host cell corresponds to biological deposit PTA-125176 or a yeast cell having the characteristics of the biological deposit PTA-125176.

Since the presence of a constitutive and elevated intracellular cAMP level is associated with increased yield and/or increased biological activity of the heterologous protein per cell, the ancestral yeast host cell can be selected based on the fact that it produces a higher amount or a higher biological activity associated with the heterologous protein per cell. The selection can be based, for example, on a comparison with an amount/biological activity of the heterologous protein expressed by a control yeast cell. In some embodiments, the control yeast host cell corresponds to biological deposit PTA-125176 or a yeast cell having the characteristics of the biological deposit PTA-125176.

Since, in some embodiments, the nucleic acid sequence of the CYR1 is indicative of an altered intracellular cAMP signaling (or a constitutive intracellular cAMP level), the selection can be made by determining the nucleic acid sequence (e.g., sequencing) of the CYR1 gene or determining the amino acid sequence of the CYR1 protein expressed in the ancestral host cell. For example, the ancestral host cell can be selected based on the fact that it bears a variant CYR1 gene/natively expresses a variant CYR1 protein which includes one or more genetic modifications (e.g., insertion, addition and/or modification of at least one nucleic acid residue) when compared to the wild-type CYR1 gene either located in its non-coding and/or coding sequence. The genetic modification can be, for example, a single polymorphic nucleotide (SNP) in the CYR1 gene. The genetic modification can lead to the presence of one or more variations (e.g., insertion, addition and/or modification of at least one amino acid residue) in the amino acid sequence of the variant CYR1 protein. The at least one variations may be located in the leucine rich repeats region of the protein (and in some embodiments altering its ability to bind to the Ras protein) and/or in the phosphatase region of the protein (and in some embodiments, altering its ability to remove phosphate moieties from its substrate).

In embodiments in which the wild-type (reference) CYR1 gene has the nucleic acid sequence of SEQ ID NO: 1, the variant CYR1 gene can include one or more SNP at the following corresponding positions: 772 or 2480. In some embodiments, the variant CYR1 gene can include the following two or more SNPs at positions corresponding to 772 and 2480. For example, the variant CYR1 gene can have, at a position corresponding to position 772 of SEQ ID NO: 1 another nucleic acid base than G (A for example). In another example, the variant CYR1 gene can have, at a position corresponding to position 2480 of SEQ ID NO: 1, another nucleic acid base than C (T for example). In some embodiments, the variant CYR1 gene can have, at a position corresponding to position 772 of SEQ ID NO: 1, another nucleic acid base than G (A for example) and, at a position corresponding to position 2480 of SEQ ID NO: 1, another nucleic acid base than C (T for example). In some embodiments, the variant CYR1 gene can have the nucleic acid sequence of SEQ ID NO: 5.

In embodiments in which the wild-type (reference) CYR1 gene has the nucleic acid sequence of SEQ ID NO: 7, the variant CYR1 gene can include one or more SNP at positions corresponding to 772, 2504, 2605 or 4305. In some embodiments, the variant CYR1 gene can include two or more SNPs at the positions corresponding to 772, 2504, 2605 and/or 4305. In additional embodiments, the variant CYR1 gene can include three or more SNPs at the positions corresponding to positions 772, 2504, 2605 and/or 4305. In some further embodiments, the variant CYR1 gene can include four or more SNPs at the following positions: 772, 2504, 2605 and 4305. For example, the variant CYR1 gene can have, at a position corresponding to position 772 of SEQ ID NO: 7, another nucleic acid base than G (A for example). In another example, the variant CYR1 gene can have, at a position corresponding to position 2504 of SEQ ID NO: 7, another nucleic acid base than C (T for example). In still another example, the variant CYR1 gene can have, at a position corresponding to position 2605 of SEQ ID NO: 7, a nucleic acid based other than G (A for example). In yet a further example, the variant CYR1 gene can have, at a position corresponding to position 4305 of SEQ ID NO: 7, another nucleic acid base than C (A for example). In an embodiment, the variant CYR1 gene can have, at a position corresponding to position 772 of SEQ ID NO: 7, another nucleic acid base than G (A for example) and at a position corresponding to position 2504 of SEQ ID NO: 7, another nucleic acid base than C (T for example). In an embodiment, the variant CYR1 gene can have, at a position corresponding to position 772 of SEQ ID NO: 7, another nucleic acid base than G (A for example) and at a position corresponding to position 2605 of SEQ ID NO: 7, a nucleic acid based other than G (A for example). In an embodiment, the variant CYR1 gene can have, at a position corresponding to position 772 of SEQ ID NO: 7, another nucleic acid base than G (A for example) and at a position corresponding to position 4305 of SEQ ID NO: 7, another nucleic acid base than C (A for example). In an embodiment, the variant CYR1 gene can have, at a position corresponding to position 2504 of SEQ ID NO: 7, another nucleic acid base than C (T for example) and at a position corresponding to position 2605 of SEQ ID NO: 7, a nucleic acid based other than G (A for example). In an embodiment, the variant CYR1 gene can have, at a position corresponding to position 2504 of SEQ ID NO: 7, another nucleic acid base than C (T for example) and at a position corresponding to position 4305 of SEQ ID NO: 7, another nucleic acid base than C (A for example). In still another embodiment, the variant CYR1 gene can have, at a position corresponding to position 2605 of SEQ ID NO: 7, a nucleic acid based other than G (A for example) and at a position corresponding to position 4305 of SEQ ID NO: 7, another nucleic acid base than C (A for example). In an embodiment, the variant CYR1 gene can have, at a position corresponding to position 772 of SEQ ID NO: 7, another nucleic acid base than G (A for example), at a position corresponding to position 2504 of SEQ ID NO: 7, another nucleic acid base than C (T for example) and at a position corresponding to position 2605 of SEQ ID NO: 7, a nucleic acid based other than G (A for example). In an embodiment, the variant CYR1 gene can have, at a position corresponding to position 2504 of SEQ ID NO: 7, another nucleic acid base than C (T for example), at a position corresponding to position 2605 of SEQ ID NO: 7, a nucleic acid based other than G (A for example) and at a position corresponding to position 4305 of SEQ ID NO: 7, another nucleic acid base than C (A for example). In an embodiment, the variant CYR1 gene can have, at a position corresponding to position 772 of SEQ ID NO: 7, another nucleic acid base than G (A for example), at a position corresponding to position 2605 of SEQ ID NO: 7, a nucleic acid based other than G (A for example) and at a position corresponding to position 4305 of SEQ ID NO: 7, another nucleic acid base than C (A for example). In an embodiment, the variant CYR1 gene can have, at a position corresponding to position 772 of SEQ ID NO: 7, another nucleic acid base than G (A for example), at a position corresponding to position 2504 of SEQ ID NO: 7, another nucleic acid base than C (T for example) and at a position corresponding to position 4305 of SEQ ID NO: 7, another nucleic acid base than C (A for example). In yet a further example, the variant CYR1 gene can have, at a position corresponding to position 4305 of SEQ ID NO: 7, another nucleic acid base than C (A for example). In an embodiment, the variant CYR1 gene can have, at a position corresponding to position 772 of SEQ ID NO: 7, another nucleic acid base than G (A for example), at a position corresponding to position 2504 of SEQ ID NO: 7, another nucleic acid base than C (T for example), at a position corresponding to position 2605 of SEQ ID NO: 7, a nucleic acid based other than G (A for example) and at a position corresponding to position 4305 of SEQ ID NO: 7, another nucleic acid base than C (A for example). In some embodiments, the variant CYR1 gene can have the nucleic acid sequence of SEQ ID NO: 5.

In embodiments in which the wild-type (reference) CYR1 protein has the amino acid sequence of SEQ ID NO: 2, the variant CYR1 protein can include one or more variations at the following corresponding positions: 258 and 827. In some embodiments, the variant CYR1 protein includes at least two variations at the following corresponding positions: 258 and/or 827. In an example, the variant CYR1 protein could have, at a position corresponding to position 258 of SEQ ID NO: 1, an amino acid residue which is not an alanine residue (a threonine residue for example). In another example, the variant CYR1 protein could have, at a position corresponding to position 835 of SEQ ID NO: 2, an amino acid residue different than an alanine residue (a valine residue for example). In an embodiment, the variant CYR1 protein could have, at a position corresponding to position 258 of SEQ ID NO: 1, an amino acid residue which is not an alanine residue (a threonine residue for example) and at a position corresponding to position 835 of SEQ ID NO: 2, an amino acid residue different than an alanine residue (a valine residue for example). In another embodiment, the variant CYR1 protein can have the amino acid sequence of SEQ ID NO: 6.

In embodiments in which the wild-type (reference) CYR1 protein has the amino acid sequence of SEQ ID NO: 8, the variant CYR1 protein can include one or more variations at the following corresponding positions: 258 835, 869 and/or 1435. In some embodiments, the variant CYR1 protein includes at least two variations at the following corresponding positions: 258 835, 869 and/or 1435. In some additional embodiments, the variant CYR1 protein includes at least three variations at the following positions: 258, 835, 869 and/or 1435. In still further embodiments, the variant CYR1 protein includes at least four variations at the following positions: 258, 835, 869 and 1435. In an example, the variant CYR1 protein could have, at position 258 of SEQ ID NO: 8, an amino acid residue which is not an alanine residue (a threonine residue for example). In another example, the variant CYR1 protein could have, at position 835 of SEQ ID NO: 8, an amino acid residue which is not an alanine residue (a valine residue for example). In a further example, the variant CYR1 protein could have, at position 869 of SEQ ID NO: 8, an amino acid residue which is not a glutamic acid residue (a lysine residue for example). In yet another example, the variant CYR1 protein could have, at position 1435 of SEQ ID NO: 8, an amino acid residue which is different from an aspartic acid residue (a glutamic acid residue for example). In an example, the variant CYR1 protein could have, at position 258 of SEQ ID NO: 8, an amino acid residue which is not an alanine residue (a threonine residue for example) and at position 835 of SEQ ID NO: 8, an amino acid residue which is not an alanine residue (a valine residue for example). In an example, the variant CYR1 protein could have, at position 258 of SEQ ID NO: 8, an amino acid residue which is not an alanine residue (a threonine residue for example) and at position 869 of SEQ ID NO: 8, an amino acid residue which is not a glutamic acid residue (a lysine residue for example). In an example, the variant CYR1 protein could have, at position 258 of SEQ ID NO: 8, an amino acid residue which is not an alanine residue (a threonine residue for example) and, at position 1435 of SEQ ID NO: 8, an amino acid residue which is different from an aspartic acid residue (a glutamic acid residue for example). In another example, the variant CYR1 protein could have, at position 835 of SEQ ID NO: 8, an amino acid residue which is not an alanine residue (a valine residue for example) and, at position 869 of SEQ ID NO: 8, an amino acid residue which is not a glutamic acid residue (a lysine residue for example). In another example, the variant CYR1 protein could have, at position 835 of SEQ ID NO: 8, an amino acid residue which is not an alanine residue (a valine residue for example) and, at position 1435 of SEQ ID NO: 8, an amino acid residue which is different from an aspartic acid residue (a glutamic acid residue for example). In an example, the variant CYR1 protein could have, at position 258 of SEQ ID NO: 8, an amino acid residue which is not an alanine residue (a threonine residue for example), at position 835 of SEQ ID NO: 8, an amino acid residue which is not an alanine residue (a valine residue for example) and, at position 869 of SEQ ID NO: 8, an amino acid residue which is not a glutamic acid residue (a lysine residue for example). In an example, the variant CYR1 protein could have, at position 258 of SEQ ID NO: 8, an amino acid residue which is not an alanine residue (a threonine residue for example). In another example, the variant CYR1 protein could have, at position 835 of SEQ ID NO: 8, an amino acid residue which is not an alanine residue (a valine residue for example) and, at position 1435 of SEQ ID NO: 8, an amino acid residue which is different from an aspartic acid residue (a glutamic acid residue for example). In an example, the variant CYR1 protein could have, at position 258 of SEQ ID NO: 8, an amino acid residue which is not an alanine residue (a threonine residue for example), at position 835 of SEQ ID NO: 8, an amino acid residue which is not an alanine residue (a valine residue for example) and, at position 1435 of SEQ ID NO: 8, an amino acid residue which is different from an aspartic acid residue (a glutamic acid residue for example). In an example, the variant CYR1 protein could have, at position 258 of SEQ ID NO: 8, an amino acid residue which is not an alanine residue (a threonine residue for example), at position 835 of SEQ ID NO: 8, an amino acid residue which is not an alanine residue (a valine residue for example) and, at position 1435 of SEQ ID NO: 8, an amino acid residue which is different from an aspartic acid residue (a glutamic acid residue for example). In another example, the variant CYR1 protein could have, at position 835 of SEQ ID NO: 8, an amino acid residue which is not an alanine residue (a valine residue for example), at position 869 of SEQ ID NO: 8, an amino acid residue which is not a glutamic acid residue (a lysine residue for example) and, at position 1435 of SEQ ID NO: 8, an amino acid residue which is different from an aspartic acid residue (a glutamic acid residue for example). In another embodiment, the variant CYR1 protein can have the amino acid sequence of SEQ ID NO: 6.

In some embodiments, the method includes, prior to the selection step, introducing a second heterologous nucleic acid encoding for a variant CYR1 gene (as disclosed herein) encoding a variant CYR1 protein (as disclosed herein).

In some additional embodiments, it may be beneficial to have a recombinant yeast host cell having at least one or more polyploid chromosome. This can allow, for example, the presence of numerous copies of the gene encoding the heterologous protein and/or the variant CYR1 gene. As such, it may be advisable to select the ancestral host cell based on the status of ploidy of its chromosomes. In some embodiments, the ancestral yeast host cell is selected based on the presence of polyploidy (e.g., triploidy or tetraploidy) in at least one, two, three, four, five, six, seven, eight, nine, ten, eleven, twelve, thirteen, fourteen, fifteen or sixteen chromosomes. In some embodiments, the ancestral yeast host cell is selected based on the presence of triploidy in at least one, two, three, four, five, six, seven, eight, nine, ten, eleven, twelve, thirteen, fourteen, fifteen or sixteen chromosomes. Alternatively or in combination, the ancestral yeast host cell is selected based on the presence of tetraploidy in at least one, two, three, four, five, six, seven, eight, nine, ten, eleven, twelve, thirteen, fourteen, fifteen or sixteen chromosomes. In some specific embodiments, the ancestral yeast host cell is selected based on the presence of a majority of triploid chromosomes. In some further specific embodiments, the ancestral yeast host cell is selected based on the absence of haploid or diploid chromosomes. In some additional specific embodiments, the recombinant yeast host cell has two tetraploid chromosomes with the remainder of chromosomes triploid.

In some embodiments, the method includes, prior or after to the selection step, modifying the ploidy of the ancestral yeast host cell by using mating techniques known in the art. The step of modifying ploidy can occur before or after introducing the optional second heterologous nucleic acid encoding for a variant CYR1 gene (as disclosed herein) encoding a variant CYR1 protein (as disclosed herein).

In order to make the recombinant yeast host cells of the present disclosure, one or more heterologous nucleic acid molecules (also referred to as expression cassettes) are made in vitro and introduced into the yeast host cell in order to allow the recombinant expression of the heterologous protein.

The heterologous nucleic acid molecules of the present disclosure comprise a coding region. A DNA or RNA "coding region" is a DNA or RNA molecule (preferably a DNA molecule) which is transcribed and/or translated into a protein in a cell in vitro or in vivo when placed under the control of appropriate regulatory sequences. "Suitable regulatory regions" refer to nucleic acid regions located upstream (5' non-coding sequences), within, or downstream (3' non-coding sequences) of a coding region, and which influence the transcription, RNA processing or stability, or translation of the associated coding region. Regulatory regions may include promoters, translation leader sequences, RNA processing site, effector binding site and stem-loop structure. The boundaries of the coding region are determined by a start codon at the 5' (amino) terminus and a translation stop codon at the 3' (carboxyl) terminus. A coding region can include, but is not limited to, prokaryotic regions, cDNA from mRNA, genomic DNA molecules, synthetic DNA molecules, or RNA molecules. If the coding region is intended for expression in a eukaryotic cell, a polyadenylation signal and transcription termination sequence will usually be located 3' to the coding region. In an embodiment, the coding region can be referred to as an open reading frame. "Open reading frame" is abbreviated ORF and means a length of nucleic acid, either DNA, cDNA or RNA, that comprises a translation start signal or initiation codon, such as an ATG or AUG, and a termination codon and can be potentially translated into a protein.

The heterologous nucleic acid molecules described herein can comprise non-coding sequence such as transcriptional and/or translational control regions. "Transcriptional and translational control regions" are DNA regulatory regions, such as promoters, enhancers, terminators, and the like, that provide for the expression of a coding region in a host cell. In eukaryotic cells, polyadenylation signals are control regions.

In some embodiments, the heterologous nucleic acid molecules of the present disclosure include a promoter as well as a coding sequence for a protein. The heterologous nucleic acid sequence can also include a terminator. In the heterologous nucleic acid molecules of the present disclosure, the promoter and the terminator (when present) are operatively linked to the nucleic acid coding sequence of the protein, e.g., they control the expression and the termination of expression of the nucleic acid sequence of the protein. The heterologous nucleic acid molecules of the present disclosure can also include a nucleic acid coding for a signal peptide, e.g., a short peptide sequence for exporting the heterologous protein outside the host cell. When present, the nucleic acid sequence coding for the signal peptide is directly located upstream and is in frame with the nucleic acid sequence coding for the protein.

In the heterologous nucleic acid molecule described herein, the promoter and the nucleic acid molecule coding for the protein. In the context of the present disclosure, the expressions "operatively linked" or "operatively associated" refers to fact that the promoter is physically associated to the nucleotide acid molecule coding for the protein in a manner that allows, under certain conditions, for expression of the heterologous protein from the nucleic acid molecule. In an embodiment, the promoter can be located upstream (5') of the nucleic acid sequence coding for the heterologous protein. In still another embodiment, the promoter can be located downstream (3') of the nucleic acid sequence coding for the protein. In the context of the present disclosure, one or more than one promoter can be included in the heterologous nucleic acid molecule. When more than one promoter is included in the heterologous nucleic acid molecule, each of the promoters is operatively linked to the nucleic acid sequence coding for the protein. The promoters can be located, in view of the nucleic acid molecule coding for the heterologous protein, upstream, downstream as well as both upstream and downstream.

"Promoter" refers to a DNA fragment capable of controlling the expression of a coding sequence or functional RNA. The term "expression," as used herein, refers to the transcription and stable accumulation of sense (mRNA) from the heterologous nucleic acid molecule described herein. Expression may also refer to translation of mRNA into a polypeptide. Promoters may be derived in their entirety from a native gene, or be composed of different elements derived from different promoters found in nature, or even comprise synthetic DNA segments. It is understood by those skilled in the art that different promoters may direct the expression at different stages of development, or in response to different environmental or physiological conditions. Promoters which cause a gene to be expressed in most cells at most times at a substantial similar level are commonly referred to as "constitutive promoters". It is further recognized that since in most cases the exact boundaries of regulatory sequences have not been completely defined, DNA fragments of different lengths may have identical promoter activity. A promoter is generally bounded at its 3' terminus by the transcription initiation site and extends upstream (5 direction) to include the minimum number of bases or elements necessary to initiate transcription at levels detectable above background. Within the promoter will be found a transcription initiation site (conveniently defined for example, by mapping with nuclease S1), as well as protein binding domains (consensus sequences) responsible for the binding of the polymerase.

The promoter can be native or heterologous to the nucleic acid molecule encoding the protein. The promoter can be heterologous or derived from a strain being from the same genus or species as the recombinant host cell. In an embodiment, the promoter is derived from the same genus or species of the yeast host cell and the heterologous protein is derived from a different genus than the host cell. The promoter can be a single promoter or a combination of different promoters.

Promoters that can be included in the heterologous nucleic acid molecule of the present disclosure include, without limitation, the promoter of the tdh1 gene (referred to as tdh1p), of the hor7 gene (referred to as hor7p), of the hsp150 gene (referred to as hsp150p), of the hxt7 gene (referred to as hxt7p), of the gpm1 gene (referred to as gpm1p), of the pgk1 gene (referred to as pgk1p) and/or of the stl1 gene (referred to as stl1p).

One or more promoters can be used to allow the expression of each heterologous polypeptides in the recombinant yeast host cell. In the context of the present disclosure, the expression "functional fragment of a promoter" when used in combination to a promoter refers to a shorter nucleic acid sequence than the native promoter which retain the ability to control the expression of the nucleic acid sequence encoding the protein. Usually, functional fragments are either 5' and/or 3' truncation of one or more nucleic acid residue from the native promoter nucleic acid sequence.

In some embodiments, the nucleic acid molecules include one or a combination of terminator sequence(s) to end the translation of the protein. The terminator can be native or heterologous to the nucleic acid sequence encoding the protein. In some embodiments, one or more terminators can be used. In some embodiments, the terminator comprises the terminator derived from is from the dit1 gene (referred to as dit1t), from the idp1 gene (referred to as idp1t), from the gpm1 gene (referred to as gpm1t), from the pma1 gene (referred to as pma1t), from the tdh3 gene (referred to as tdh3t), from the hxt2 gene (referred to as hxt2t), from the adh3 gene (referred to as adh3t), and/or from the ira2 gene (referred to as ira2t). In the context of the present disclosure, the expression "functional variant of a terminator" refers to a nucleic acid sequence that has been substituted in at least one nucleic acid position when compared to the native terminator which retain the ability to end the expression of the nucleic acid sequence coding for the protein. In the context of the present disclosure, the expression "functional fragment of a terminator" refers to a shorter nucleic acid sequence than the native terminator which retain the ability to end the expression of the nucleic acid sequence coding for the protein.

In some embodiments, the heterologous nucleic acid molecules include one or a combination of signal sequence(s) allowing the export of the heterologous protein outside the yeast host cell's wall. The signal sequence can simply be added to the nucleic acid molecule (usually in frame with the sequence encoding the heterologous protein) or replace the signal sequence already present in the heterologous protein. The signal sequence can be native or heterologous to the nucleic acid sequence encoding the heterologous protein. In some embodiments, one or more signal sequences can be used. In some embodiments, the signal sequence is from the invertase protein, the AGA2 protein or the fungal amylase, including variants and fragments thereof. In the context of the present disclosure, the expression "functional variant of a signal sequence" refers to a nucleic acid sequence that has been substituted in at least one nucleic acid position when compared to the native signal sequence which retain the ability to direct the expression of the heterologous protein outside the cell. In the context of the present disclosure, the expression "functional fragment of a signal sequence" refers to a shorter nucleic acid sequence than the native signal sequence which retain the ability to direct the expression of the protein outside the cell.

In some embodiments in which it is desirable to express the heterologous protein inside the recombinant yeast host cell, the heterologous nucleic acid molecule can exclude the portion coding for the signal sequence which is found in the native gene encoding the protein.

The heterologous nucleic acid molecules can be integrated in the genome of the yeast host cell. The term "integrated" as used herein refers to genetic elements that are placed, through molecular biology techniques, into the genome of a host cell. For example, genetic elements can be placed into the chromosomes of the host cell as opposed to in a vector such as a plasmid carried by the host cell. Methods for integrating genetic elements into the genome of a host cell are well known in the art and include homologous recombination. The heterologous nucleic acid molecule can be present in one or more copies in the yeast host cell's genome. Alternatively, the heterologous nucleic acid molecule can be independently replicating from the yeast's genome. In such embodiment, the nucleic acid molecule can be stable and self-replicating.

The present disclosure also provides nucleic acid molecules for modifying the yeast host cell so as to allow the expression of the heterologous protein(s) and optionally the variant CYR1 protein. The nucleic acid molecule may be DNA (such as complementary DNA, synthetic DNA or genomic DNA) or RNA (which includes synthetic RNA) and can be provided in a single stranded (in either the sense or the antisense strand) or a double stranded form. The contemplated nucleic acid molecules can include alterations in the coding regions, non-coding regions, or both. Examples are nucleic acid molecule variants containing alterations which produce silent substitutions, additions, or deletions, but do not alter the properties or activities of the encoded heterologous proteins, variants or fragments.

In some embodiments, the heterologous nucleic acid molecules which can be introduced into the recombinant host cells are codon-optimized with respect to the intended recipient recombinant yeast host cell. As used herein the term "codon-optimized coding region" means a nucleic acid coding region that has been adapted for expression in the cells of a given organism by replacing at least one, or more than one, codons with one or more codons that are more frequently used in the genes of that organism. In general, highly expressed genes in an organism are biased towards codons that are recognized by the most abundant tRNA species in that organism. One measure of this bias is the "codon adaptation index" or "CAI," which measures the extent to which the codons used to encode each amino acid in a particular gene are those which occur most frequently in a reference set of highly expressed genes from an organism. The CAI of codon optimized heterologous nucleic acid molecule described herein corresponds to between about 0.8 and 1.0, between about 0.8 and 0.9, or about 1.0.

The heterologous nucleic acid molecules can be introduced in the yeast host cell using a vector. A "vector," e.g., a "plasmid", "cosmid" or "artificial chromosome" (such as, for example, a yeast artificial chromosome) refers to an extra chromosomal element and is usually in the form of a circular double-stranded DNA molecule. Such vectors may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The present disclosure also provides nucleic acid molecules that are hybridizable to the complement nucleic acid molecules encoding the proteins as well as variants or fragments. A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified, e.g., in Sambrook, J., Fritsch, E. F. and Maniatis, T. MOLECULAR CLONING: A LABORATORY MANUAL, Second Edition, Cold Spring Harbor Laboratory Press, Cold Spring Harbor (1989), particularly Chapter 11 and Table 11.1 therein. The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. For more stringent conditions, washes are performed at higher temperatures in which the washes are identical to those above except for the temperature of the final two 30 min washes in 0.2×SSC, 0.5% SDS are increased to 60° C. Another set of highly stringent conditions uses two final washes in 0.1×SSC, 0.1% SDS at 65° C. An additional set of highly stringent conditions are defined by hybridization at 0.1×SSC, 0.1% SDS, 65° C. and washed with 2×SSC, 0.1% SDS followed by 0.1×SSC, 0.1% SDS.

Hybridization requires that the two nucleic acid molecules contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA: RNA, DNA:RNA, DNA:DNA. For hybrids of greater than 100 nucleotides in length, equations for calculating Tm have been derived. For hybridizations with shorter nucleic acids, i.e., oligonucleotides, the position of mismatches becomes more important, and the length of the oligonucleotide determines its specificity. In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

Processes Using the Recombinant Yeast Host Cell

The recombinant yeast host cells of the present disclosure are intended to be used in the processes for making a yeast product. The recombinant yeast host cell of the present disclosure (and, by the same token the yeast product) expresses and comprises the heterologous protein. As used in the context of the present disclosure, a "yeast product" is a composition comprising the recombinant yeast host cell of the present disclosure which has been cultured or a product made by the recombinant yeast host cell of the present disclosure during fermentation and comprising the heterologous protein. In yet another embodiment, the yeast product can be a metabolite produced by the recombinant yeast host cell of the present disclosure, for example, the heterologous protein produced by the recombinant yeast host cell.

The recombinant yeast host cells of the present disclosure can optionally be used in a fermentation process (which can be continuous or fed batch). In an embodiment, the fermentation process can be a relatively long one and the recombinant yeast host cells can be used, for example, in making biofuels, distilling products, wine and beer. In another embodiment, the fermentation process can be a relatively short one and the recombinant yeast host cells can be used, for example, in making yeast-leavened bakery products.

The recombinant yeast host cells of the present disclosure can also be used in a process which does not include a fermentation step. For example, the recombinant yeast host cell can be used for making food and beverages (e.g., non-yeast-leavened (chemically-leavened) bakery products, dairy products, yeast extracts, juices, fat and oils as well as starch), feed or other industrial products (e.g., detergents, textiles, leather, pulp and paper, oil and gas and/or biopolymers).

The yeast products of the present disclosure can be provided in an active form (e.g., liquid, compressed, or fluid-bed dried yeast), in a semi-active form (e.g., liquid, compressed, or fluid-bed dried), in an inactive form (e.g., drum- or spray-dried) as well as a mixture therefore. For example, the recombinant yeast host cells can be a combination of active and semi-active or inactive forms to provide the ratio and dose of the heterologous protein required for making the yeast composition.

As indicated herein, the present disclosure allows for making a yeast product from the recombinant yeast host cell of the present disclosure. In an embodiment, the yeast product comprises at 0.5, 0.6, 0.7, 0.8, 0.9, 1.0, 1.1, 1.2, 1.3, 1.4, 1.5, 1.6, 1.7, 1.8, 1.9, 2.0, 2.1, 2.1, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 2.2, 4.3, 4.4, 4.5, 4.6, 4.7, 4.8, 4.9, 5.0 weight % or more of the heterologous protein when compared to the total proteins of the yeast product. In another embodiment, the yeast product comprises at least 0.001, 0.002, 0.003, 0.004, 0.005, 0.006, 0.007, 0.008, 0.009, 0.01, 0.011, 0.012, 0.013, 0.014, 0.015, 0.016, 0.017, 0.018, 0.019, 0.02, 0.021, 0.022, 0.023, 0.024, 0.025 g or more of the heterologous protein/g of the total proteins of the recombinant yeast host cell. In yet another embodiment, the yeast product comprises at least 0.05, 0.075, 0.1, 0.2, 0.3, 0.4, 0.5, 0.6, 0.7, 0.8, 0.9, 1.0, 1.1, 1.2, 1.3, 1.4, 1.5 weight % or more of the heterologous protein when compared to the total weight of the recombinant yeast host cell. In still a further embodiment, the yeast product comprises at least 0.0005, 0.0006, 0.0007, 0.0008, 0.0009, 0.001, 0.0011, 0.0012, 0.0013, 0.0014, 0.0015, 0.0016, 0.0017, 0.0018, 0.0019, 0.002, 0.003, 0.004, 0.005, 0.006, 0.007, 0.008, 0.009, 0.01 g or more of the heterologous protein when compared to the dry weight of the recombinant yeast host cell. In an embodiment in which the recombinant yeast host cell is formulated as a yeast cream, the yeast cream comprises at least 45, 46, 47, 48, 49, 50, 50.2, 51, 52, 53, 54, 55 weight % or more of the heterologous protein when compared to the total weight of the yeast cream. In another embodiment in which the heterologous protein is an heterologous enzyme, the present disclosure provides processes as well as yeast products having a specific minimal enzymatic activity and/or a specific range of enzymatic activity. For example, the yeast product can comprise a minimal amount of enzymatic activity which can provide a minimal enzymatic activity/g dry cell weight, which can be, for example, at least 150, 200, 250, 300, 350, 400, 450, 500, 550, 600, 650, 700, 750, 800, 850, 900, 950, 1000, 2000, 3000, 4000, 5000, 6000, 7000, 8000 or more enzymatic activity units/g of dry cell weight. Alternatively or in combination, the yeast product can provide a minimal enzymatic activity/g or mg of the total protein of the recombinant yeast host cell, which can be, for example, 50, 100, 150, 200, 250, 300, 350, 400, 450, 500, 550, 600, 650, 700, 750, 800, 850, 900, 950 or more enzymatic activity units/g or mg of total proteins of the recombinant yeast host cell. In another example, when the heterologous enzyme is an amylase such as a maltogenic amylase, the yeast product can comprises a minimal amount of maltogenic amylase activity (for example, measured as MAU/g of dry weight of the yeast product) which can be, for example, at least about 150, 200, 250, 300, 350, 400, 450, 500, 550, 600, 650, 700, 750, 800, 850, 900, 950, 1000, 2000, 3000, 4000, 5000, 6000, 7000, 8000 or more MAU/g of dry cell weight or 50, 100, 150, 200, 250, 300, 350, 400, 450, 500, 550, 600, 650, 700, 750, 800, 850, 900, 950 or more MAU/g of total proteins of the recombinant yeast host cell. In still another example, when the heterologous enzyme is an amylase such as a glucoamylase, the yeast product can comprise a minimal amount of glucoamylase activity (for example, measured as units of glucoamylase activity/g of dry weight of the yeast product), which can be, for example, 150, 200, 250, 300, 350, 400, 450, 500, 550, 600, 650, 700, 750, 800, 850, 900, 950, 1000, 2000, 3000, 4000, 5000, 6000, 7000, 8000 or more glucoamylase units/g of dry cell weight. In a further embodiment, when the heterologous enzyme is an amylase such as an alpha-amylase, the yeast product can comprise a minimal amount of alpha-amylase activity (for example, measured as units of alpha-amylase activity/g of dry weight of the yeast product), which can be, for example, 150, 200, 250, 300, 350, 400, 450, 500, 550, 600, 650, 700, 750, 800, 850, 900, 950, 1000, 2000, 3000, 4000, 5000, 6000, 7000, 8000 or more alpha-amylase units/g of dry cell weight. In still another embodiment, when the heterologous enzyme is a phosphatase such as a phytase, the yeast product can comprise a minimal amount of phytase activity (for example, measured as units of phytase activity/g of dry weight of the yeast product), which can be, for example, 150, 200, 250, 300, 350, 400, 450, 500, 550, 600, 650, 700, 750, 800, 850, 900, 950, 1000, 2000, 3000, 4000, 5000, 6000, 7000, 8000 or more phytase activity units/g of dry cell weight. In still another example, when the heterologous enzyme is an oxidase such as a glucose oxidase, the yeast product can comprise a minimal amount of glucose oxidase activity (for example, measured as units of glucose oxidase activity/g of dry weight of the yeast product), which can be, for example, 150, 200, 250, 300, 350, 400, 450, 500, 550, 600, 650, 700, 750, 800, 850, 900, 950, 1000, 2000, 3000, 4000, 5000, 6000, 7000, 8000 or more glucose oxidase activity units/g of dry cell weight.

The process for making the yeast product broadly comprises two steps: a first step of culturing (either continuously or in batch) the recombinant yeast host cell and a second step of formulating the yeast product. In the formulating step, the mixture obtained after culture can be modified to provide a yeast product. In an embodiment for providing a yeast product, at least one component of the mixture obtained after culture is removed from the culture medium to provide the yeast product. This component can be, without limitation, water, amino acids, peptides and proteins, nucleic acid residues and nucleic acid molecules, cellular debris, fermentation products, etc. In an embodiment, the formulating step comprises substantially isolating the cultured yeast recombinant host cells (e.g., the biomass) from the components of the culture medium. As used in the context of the present disclosure, the expression "substantially purifying/isolating" refers to the removal of the majority of the components of the culture medium from the cultured recombinant yeast host cells. In some embodiments, "substantially purifying/isolating" refers to concentrating the cultured recombinant yeast host cell to at least 5, 10, 15, 20, 25, 30, 35, 45% or more when compared to the concentration of the recombinant yeast host cell prior to the isolation. In order to provide the yeast product, the cultured recombinant yeast host cells can be centrifuged (and the resulting cellular pellet comprising the cultured recombinant yeast host cells can optionally be washed), filtered and/or dried (optionally using a vacuum-drying technique). The isolated recombinant yeast host cells can then be formulated in a yeast product. The formulation step can, in some embodiments, preserve the viability (at least in part) of the recombinant yeast host cells. As such, the yeast product can be provided in an active or a semi-active form. The yeast product can be provided in a liquid, semi-solid or dry form. In an embodiment, the yeast product can be provided in the form of a cream yeast.

In another embodiment in which the heterologous protein is an heterologous enzyme, the present disclosure provides processes as well as yeast products having a specific minimal enzymatic activity and/or a specific range of enzymatic activity. In addition, when the recombinant yeast host cell expresses a cell-associated heterologous protein, the yeast composition can be concentrated during processing and can remains biologically active to perform its intended function in the yeast products.

In some embodiments, the process for making the yeast product further comprises an additional step of lysing the cultured yeast host cells. The process can include an optional separating step and an optional drying step. For example, the cultured recombinant host cells can be provided, for example, as a 20% cream yeast even though additional embodiments of the cultured recombinant host cells can be provided. Then, the cultured recombinant yeast host cells can be lysed to provide lysed recombinant yeast host cells. For example, the cells can be lysed using autolysis (which can be optionally be performed in the presence of additional exogenous enzymes) or homogenized (for example using a bead-milling technique). In an embodiment, the cultured recombinant yeast host cells can be lysed using autolysis. For example, the cultured recombinant cells can be submitted to a combined heat and pH treatment for a specific amount of time (e.g., 24 h) in order to cause the autolysis of the cultured recombinant yeast host cells to provide the lysed recombinant yeast host cells. The cultured recombinant cells can be submitted to a temperature of between about 40° C. to about 70° C. or between about 50° C. to about 60° C. The cultured recombinant cells can be submitted to a temperature of at least about 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C. or 70° C. Alternatively or in combination the cultured recombinant cells can be submitted to a temperature of no more than about 70° C., 69° C., 68° C., 67° C., 66° C., 65° C., 64° C., 63° C., 62° C., 61° C., 60° C., 59° C., 58° C., 57° C., 56° C., 55° C., 54° C., 53° C., 52° C., 51° C., 50° C., 49° C., 48° C., 47° C., 46° C., 45° C., 44° C., 43° C., 42° C., 41° C. or 40° C. In another example, the cultured recombinant cells can be submitted to a pH between about 4.0 and 8.5 or between about 5.0 and 7.5. The cultured recombinant cells can be submitted to a pH of at least about, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4 or 8.5. Alternatively or in combination, the cultured recombinant cells can be submitted to a pH of no more than 8.5, 8.4, 8.3, 8.2, 8.1, 8.0, 7.9, 7.8, 7.7, 7.6, 7.5, 7.4, 7.3, 7.2, 7.1, 7.0, 6.9, 6.8, 6.7, 6.6, 6.5, 6.4, 6.3, 6.2, 6.1, 6.0, 5.9, 5.8, 5.7, 5.6, 5.5, 5.4, 5.3, 5.2, 5.1, 5.0, 4.9, 4.8, 4.7, 4.6 or 4.5.

The process for making the yeast product can also include a drying step. The drying step can include, for example, with spray-drying and/or fluid-bed drying. When the yeast product is an autolysate, the process includes directly drying the lysed recombinant yeast host cells after the lysis step without performing an additional separation of the lysed mixture.

To provide additional yeast products, it may be necessary to further separate the components of the lysed recombinant yeast host cells. For example, the cellular wall components (referred to as a "insoluble fraction") of the lysed recombinant yeast host cell may be separated from the other components (referred to as a "soluble fraction") of the lysed recombinant yeast host cells. This separating step can be done, for example, by using centrifugation and/or filtration.

In some embodiments, the insoluble fraction is not submitted to a washing step prior to the subsequent drying step to provide the cell walls as the yeast product or the subsequent drying step to provide the yeast extract as the yeast product. However, the process of the present disclosure can include one or more washing step(s).

In an embodiment of the process, the insoluble fraction can be further separated prior to drying. For example, the components of the soluble fraction having a molecular weight of more than 10 kDa can be separated out of the soluble fraction. This separation can be achieved, for example, by using filtration (and more specifically ultrafiltration). When filtration is used to separate the components, it is possible to filter out (e.g., remove) the components having a molecular weight less than about 10 kDa and retain the components having a molecular weight of more than about 10 kDa. The components of the soluble fraction having a molecular weight of more than 10 kDa can then optionally be dried to provide a retentate as the yeast product. In the process described herein, the yeast product is provided as an inactive form. The yeast product can be provided in a liquid, semi-liquid or dry form.

In an embodiment, the process can also comprise substantially isolating/purifying the heterologous proteins from the yeast product. As used in the context of the present disclosure, the expression "substantially isolating/purifying the heterologous proteins from the lysed recombinant yeast host cells" refers to the removal of the majority of the components of the lysed recombinant yeast host cells from the heterologous proteins and providing same in an isolated/purified form. The heterologous protein can be provided in a liquid form or in a solid (dried) form. As such, the present disclosure provides an isolated heterologous protein obtainable or obtained by the process described herein. In an embodiment, the isolated heterologous protein is produced by a recombinant yeast host cell having and its signal sequenced has been swapped with a signal peptide from a protein naturally expressed in an heterologous organism, such as prokaryotes, a bacteria for example. In an alternative embodiment, a signal sequence has been added to the heterologous protein and this new signal sequence is from protein naturally expressed in prokaryotes such as bacteria.

The present invention will be more readily understood by referring to the following examples which are given to illustrate the invention rather than to limit its scope.

Example I—Heterologous Protein Expression in a M18151 Strain

Background

TABLE 1

Genotypes of the *Saccharomyces cerevisiae* strains used in the examples

| Name | Heterologous enzyme Expressed | Original Strain background | Copies of genes coding for heterologous enzyme integrated per chromosome | Promoter | Terminator |
| --- | --- | --- | --- | --- | --- |
| M18151 | Not applicable-wild-type yeast strain used in baking (biological deposit PTA-125175) | | | | |
| M18152 | Not applicable-wild-type yeast strain used in baking (biological deposit PTA-125176) | | | | |
| M2390 | Not applicable-wild type yeast strain used in fuel ethanol | | | | |
| M12489 | Maltogenic alpha amylase (SEQ ID NO: 3) | M18152 | 2 | TDH1p/HOR7p | DIT1t/IDP1t |
| T2994 | Maltogenic alpha amylase (SEQ ID NO: 3) | M18151 | 2 | TDH1p/HOR7p | DIT1t/IDP1t |
| M15532 | Maltogenic alpha amylase (SEQ ID NO: 3) | M18151 | 2 | TDH1p/HOR7p | DIT1t/IDP1t |
| M16147 | *Pyrococcus furiosus* alpha-amylase (SEQ ID NO: 4) | M2390 | 2 | ADH1p/TEF2p | DIT1t/IDP1t |
| M16446 | *Pyrococcus furiosus* alpha-amylase (SEQ ID NO: 4) | M18151 | 2 | ADH1p/TEF2p | DIT1t!IDP1t |
| M16834 | *Pyrococcus furiosus* alpha-amylase (SEQ ID NO: 4) | M18152 | 2 | ADH1p/TEF2p | DIT1t/IDP1t |
| M16440 | *Pyrococcus furiosus* alpha-amylase (SEQ ID NO: 4) | M18195 | 2 | ADH1p/TEF2p | DIT1t/IDP1t |
| M16548 | *Pyrococcus furiosus* alpha-amylase (SEQ ID NO: 4) | M15344 | 2 | ADH1p/TEF2p | DIT1t/IDP1t |

TABLE 1-continued

Genotypes of the *Saccharomyces cerevisiae* strains used in the examples

| Name | Heterologous enzyme Expressed | Original Strain background | Copies of genes coding for heterologous enzyme integrated per chromosome | Promoter | Terminator |
|---|---|---|---|---|---|
| M16452 | *Pyrococcus furiosus* alpha-amylase (SEQ ID NO: 4) | M7101 | 2 | ADH1p/TEF2p | DIT1t/IDP1t |
| M16835 | *Pyrococcus furiosus* alpha-amylase (SEQ ID NO: 4) | M12548 | 2 | ADH1p/TEF2p | DIT1t/IDP1t |

Maltogenic alpha-amylase activity (FIG. 1). Samples were incubated with 2 mg/ml maltodextrin, reducing sugars were reacted with 3,5-dinitrosalicylic acid and measured at 540 nm. Enzyme activity of each samples was compared to a standard curve of known concentrations of a reference commercial maltogenic amylase.

Figure 2:
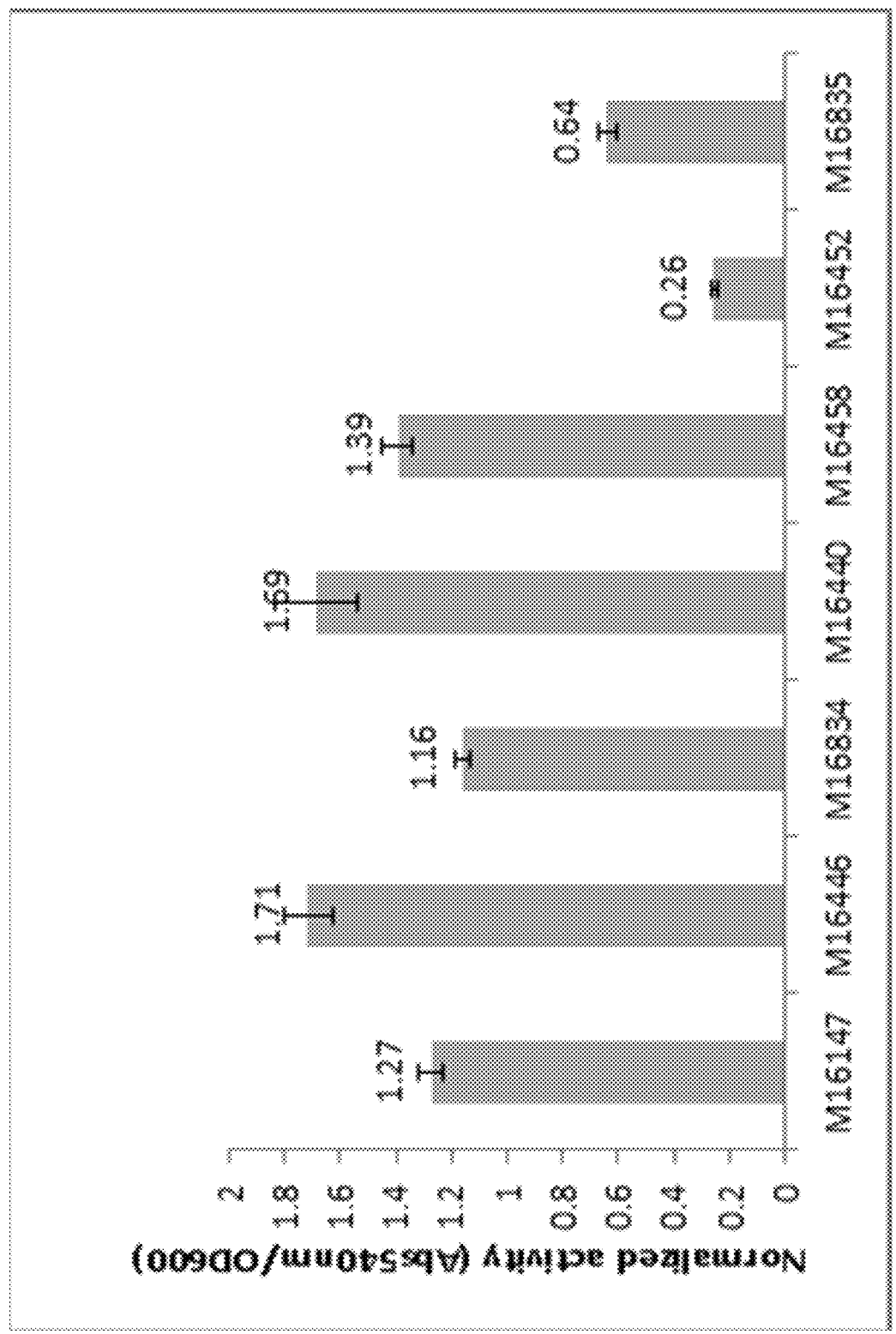
FIG. 2 illustrates the secreted alpha-amylase enzyme activity (measured as absorbance at 540 nm) in the culture supernatant of strains M16147, M16446, M16834, M16440, M16458, M16452, M16835 modified to express a heterologous alpha-amylase. Results are shown as absorbance at 540 nm normalized to cell density (OD$_{600}$) in function of strain tested.

Alpha amylase activity (FIG. 2). The strains were initially grown in 600 µL of $YPD_{40}$ at 35° C. for 48 h in 96-well plates on a shaker at 900 rpm. Alpha-amylase activity was determined by adding 25 µL of washed cells or cell-free supernatant to 100 µL of 1% raw starch with 50 mM sodium acetate buffer (pH 5.2). The assay was treated for 30 min at 85° C. using an Eppendorf Gradient Cycler. The reducing sugars were measured using the Dinitrosalicylic Acid Reagent Solution (DNS) method, using a 2:1 DNS:starch assay ratio and boiled at 10000 for 5 min. The absorbance was measured at 540 nm.

Cell growth. Cells were grown overnight in 5 mL YPD (10 g/L yeast extract, 20 g/L bacteriological peptone, 40 g/L glucose). One (1) mL of whole culture as harvested and cells were pelleted by centrifugation. Cell-free supernatant was removed and saved for later analysis. Cell pellet was washed once and resuspended in deionized water.

Cream yeast. After the fermentation, the harvested fermentation broth was centrifuged and washed using a laboratory scale separator (from GEA) to prepare yeast cream with a final dry weight close to 20%. To make the inactivated cream yeast, about 600 g of cream yeast was heated on a temperature controlled stirring/hot plate until 75° C. was reached. The cream was kept for 15 minutes at 75° C. and then removed from heat source.

Spray drying. Spray dried samples were prepared by drying with an inlet temperature of 150° C.-200 C. The feeding rate was kept to maintain outlet temperature around 85-90° C.

Fermenter autolysis. 2 000 L-22 000 liters of cream at 18-21% solids was incubated at 55° C. and pH 5.5 with mixing either with an impeller or recirculation. The autolysate (~20% dry weight) was harvested after 30 hours of incubation and separated as described below.

Separation of autolysate. Separations were performed by centrifuging fermenter autolysate in either a disc stack centrifuge with addition of a wash factor of water of 0.6 volumes, or with cross-flow microfiltration through a 0.8 micron membrane and addition of 2 diafiltration volumes of water.

Ultrafiltration. Yeast extract fractions were further concentrated by ultrafiltration with a 10 kDa molecular weight cutoff membrane. The retentate fraction is retained by the membrane and permeate fraction passes through the membrane.

Phadebas MAU enzyme activity assay. Phadebas tablets contain a water insoluble starch substrate and a blue dye, bound to the dye with crosslinks. The substrate is hydrolyzed by maltogenic amylase, releasing blue dye which is soluble. After terminating the reaction and centrifuging, the absorbance of the solution was measured spectrophotometrically and is considered a proxy for enzyme activity. For each sample, one Phadebas tablet was added to 4.9 mL of citrate-phosphate buffer (70 mM disodium hydrogen phosphate, 30 mM citric acid, pH 5.5), incubated in a 60° C. water bath for 5 minutes. Then, 0.1 mL of standard or sample, diluted in citrate-phosphate buffer, was added to the tablet and buffer solution and incubated for 15 minutes in the 60° C. water bath. The reaction was terminated by adding 1 mL of 0.5 M sodium hydroxide solution and mixing. The tubes were centrifuged to remove solids and absorbance of the substrate was measured at 620 nm with a spectrophotometer. Samples (dry or liquid) are compared to a dose curve of standards with known activity. This methods was applied to generate all of the MAU results, except for FIG. 1.

Determination of protein content. Protein content was either estimated as a percentage of total biomass by Kjeldahl method (Table 2) or was measured by Bradford assay with Bio-rad Bradford reagent and a standard curve of bovine gamma globulin dilutions.

Strain M18151 has been used for fermentation in the baking industry and it was found that this strain is an exceptionally good producer of heterologous protein. Several features appear to set this strain apart from many other *S. cerevisiae* isolates. Additionally, when strain M18151 was engineered to produce an heterologous enzyme (e.g., a maltogenic alpha-amylase or an alpha amlyase), it produced higher enzyme activity per cell than other strains engineered with a similar expression cassette (FIGS. 1 and 2). As shown in FIG. 1, the enzyme activity from the heterologous enzyme engineered to be expressed in the M18151 background strain is far greater (~60x) than the equivalent strain build in another baking strain background, M18152. While strain M18151 has significantly higher protein content than M18152 (53% compared to 44%, respectively), protein content cannot fully explain such a dramatic difference in heterologous enzyme expression.

Strain M18151 can make and release high levels of enzyme using industrially relevant processes, including homogenization and autolysis (Tables 2 and 3). Strain M155332 uses the M18151 background which was modified to express an intracellular *G. stearothermophilus* maltogenic alpha-amylase (MAA) (M15532). Strain M155332 was propagated by aerobic fed-batch on molasses and a yeast cream was then made. Its MAU activity was determined. As shown in Table 2, the heterologous enzyme is calculated to be 3.7% of total cellular protein.

TABLE 2

Calculations for maltogenic amylase as a percent of total cell protein. Enzyme activity of cream yeast and of purified enzyme was determined in a Phadebas enzyme assay with comparison to a dose curve of the standards with known maltogenic amylase units (MAU).

| | |
|---|---|
| Percent protein in cream | 53.66% |
| Enzyme activity (MAU/g dry cell weight), measured after release by autolysis | 19000 |
| Specific activity of pure enzyme (MAU/mg) | 872 |
| Specific activity of pure enzyme (MAU/g) | 872000 |
| Enzyme per gram dry weight (g/g) | 0.022 |
| Enzyme per total protein (g/g) | 0.041 |
| Enzyme as % of total protein | 4.1% |

TABLE 3

Calculations for maltogenic amylase as a percent of four different batches of dried enzyme material, obtained after autolysis of yeast expressing maltogenic amylase, separation of cell walls, further concentration and purification of the enzyme by ultrafiltration, and spray drying.

| Lot | MAU/g material | Specific activity (MAU/g enzyme) | Estimated enzyme % of material | mg total protein/g material | Enzyme % of protein |
|---|---|---|---|---|---|
| 1 | 208782 | 872000 | 24% | 373.25 | 64% |
| 2 | 287001 | | 33% | 450 | 73% |

TABLE 4

Dry weight and enzyme activity balances in autolysate yeast cell wall, yeast extract, ultrafiltration retentate, and ultrafiltration permeate preparations. Enzyme activity was determined in Phadebas enzyme assays with comparison to a dose curve of a reference commercial enzyme standards with known maltogenic amylase units (MAU). Mass and MAU balances are calculated from experimental data and do not always sum to 100% due to error in dry weight and enzyme assay measurements.

| | STEP YIELD (%) | | TOTAL YIELD (%) | |
|---|---|---|---|---|
| FRACTION | MASS | MAU | MASS | MAU |
| Autolysate | 100 | 100 | 100 | 100 |
| Cell wall | 38 | 21 | 38 | 21 |
| Yeast extract | 54 | 80 | 54 | 80 |
| UF retentate | 33 | 90 | 18 | 71 |
| UF permeate | 57 | 0 | 31 | 0 |

Example II—Characterization of the M18151 Strain

Fed-batch aerobic propagation (Table 5). Percent protein (weight protein/weight biomass) was determined by Kjeldahl method on yeast propagated in aerobic fed-batch on molasses.

Figure 3:
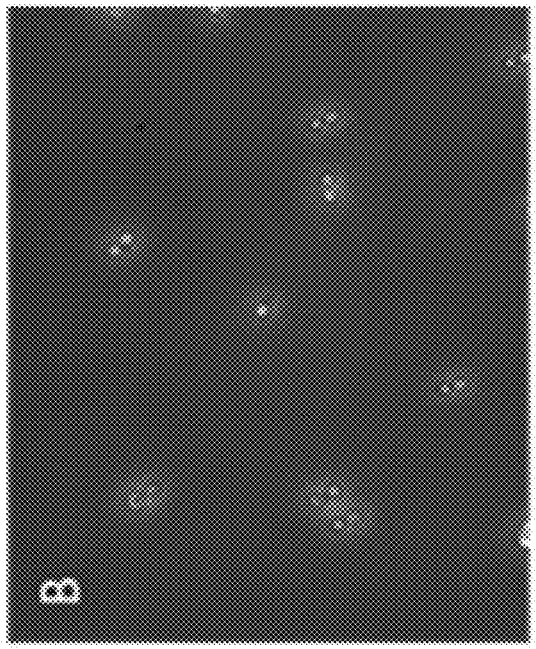
FIGS. 3A to 3D provide light microscopy images of cells of strain M2390 (FIGS. 3A and 3B) or the M18151 strain (FIGS. 3C and D).
Figure 3:
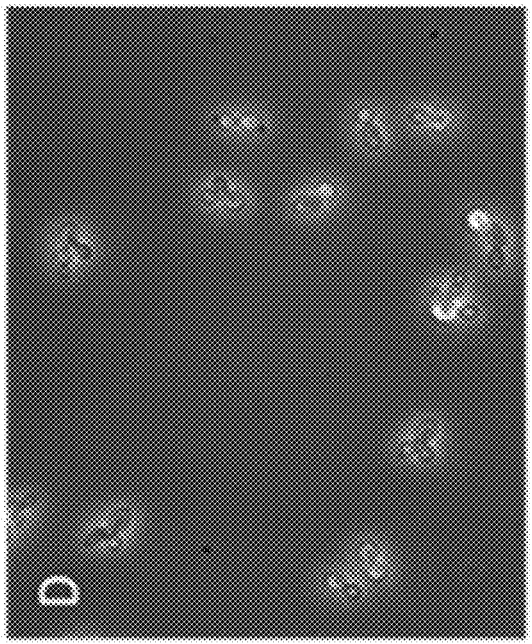
Figure 3:
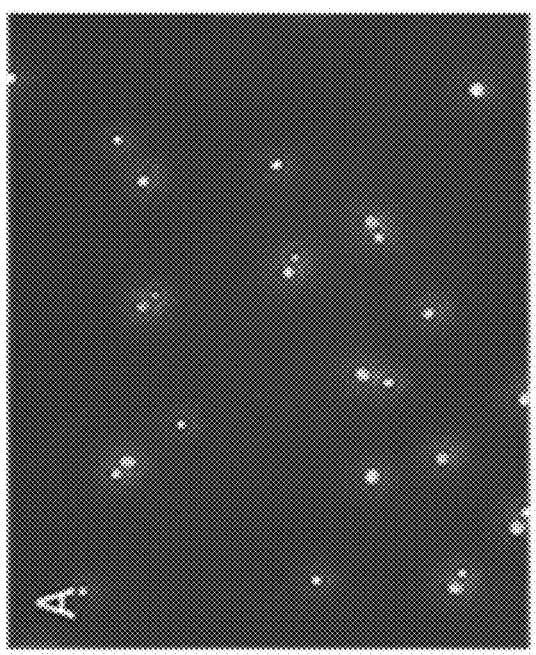
Figure 3:
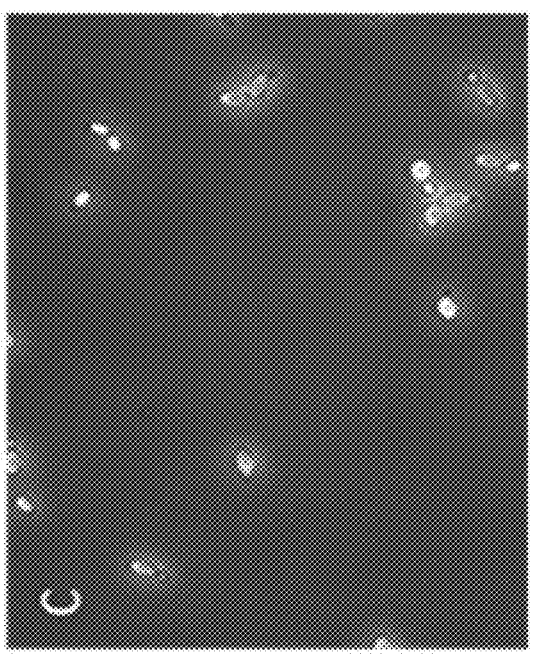

Shape characterization (FIG. 3). Yeast strains M2390 and M18151 were grown in yeast extract peptone media with 4% glucose overnight and then transferred into fresh yeast extract peptone media with 4% glucose medium. Cells were imaged under light microscopy at 400× magnification after 1 hr incubation in fresh medium.

Determination of sporulation efficiency. Yeast strains M2390 and M18151 were grown as patches overnight on yeast extract peptone agar plates with 4% glucose. A colony-sized amount of cells were picked from each patch and resuspended in 100 µL sterile deionized water. The cell suspension was plated onto sporulation medium (0.05% yeast extract, 0.5% potassium acetate, 0.025% glucose, 1% agar) and incubated at room temperature for 5 days. To measure sporulation efficiency, a colony sized amount of cells was picked from the sporulation plates and resuspended in 100 µL of sterile deionized water. 8 µL of each cell suspension was transferred to a microscope slide and examined at 1000× magnification for the presence of spores. Per strain, 210 cells were characterized as "sporulated" or "not sporulated" and the "% sporulated" was calculated by dividing the number of sporulated cells by 210.

Morphology on solid media. Strain M18151 was grown on solid yeast extract peptone supplemented with 4% glucose medium.

Ploidy determination. Whole genome de novo sequencing for M18151 was performed. The sequence was compared to the publicly available S288C reference genome, and read coverage as well as frequencies of all single nucleotide polymorphisms, divided by read coverage were aligned to the sequences of the 16 chromosomes of S288C and plotted.

Figure 4:
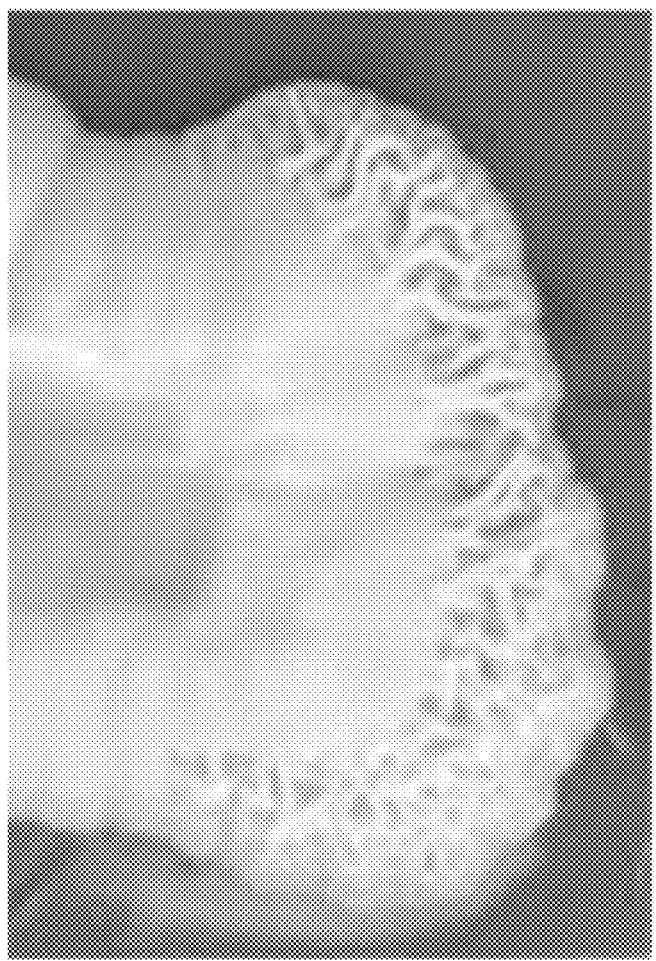
FIG. 4 provides a macroscopic view of the M18151 strain exhibiting complex colony morphology after a few days' growth on solid yeast extract peptone plus 4% glucose medium.
Figure 5:
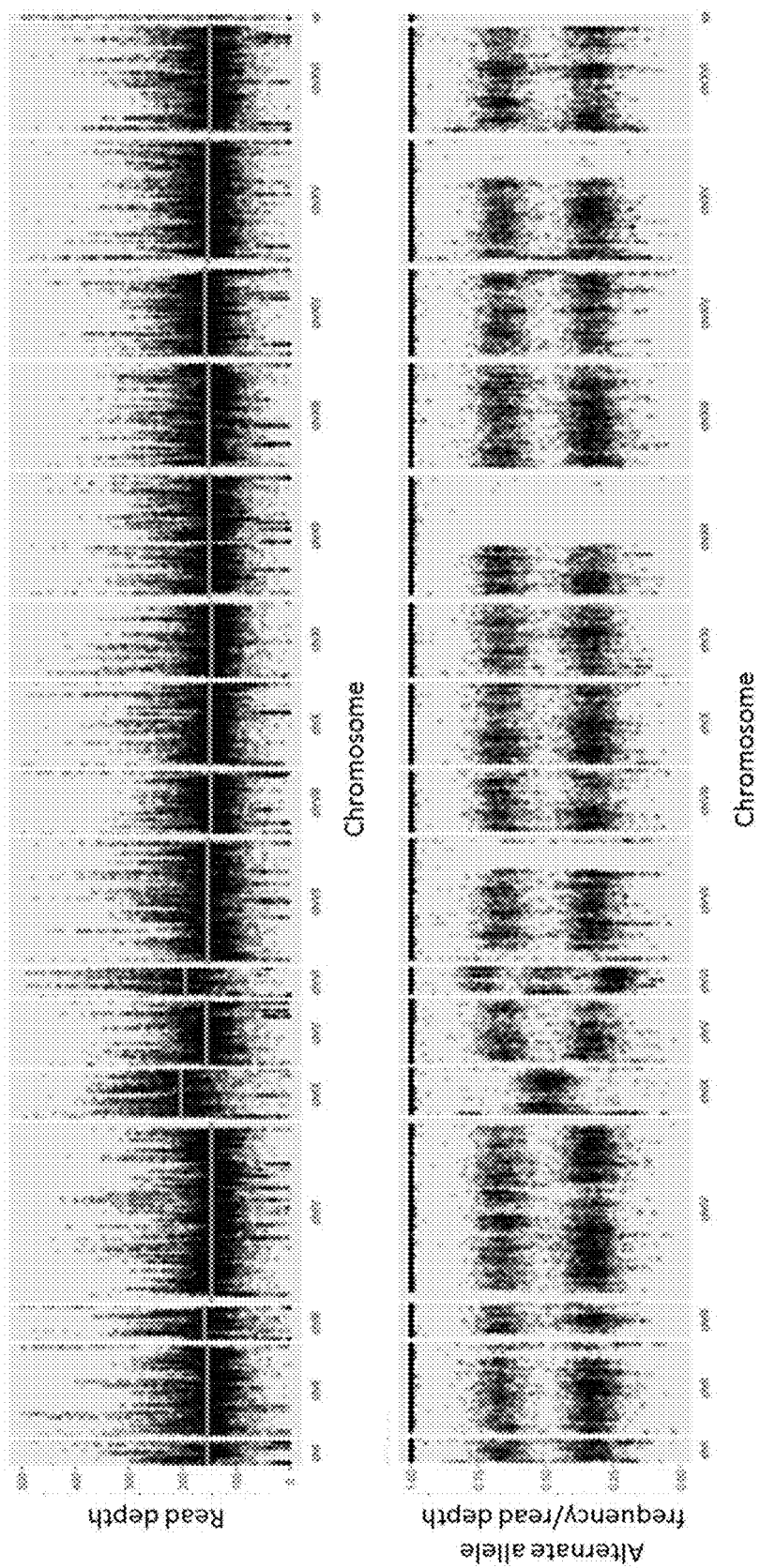
FIG. 5 illustrates the frequency of single nucleotide polymorphisms (SNPs) across chromosomes of M18151 strain. Data plots from chromosomes 1-16 are shown in numerical order from left to right and top to bottom. SNP frequencies can infer the ploidy: 0.5 indicates diploid; 0.33 and 0.67 indicate triploid; 0.25, 0.5, and 0.75 indicate tetraploid. Two chromosomes are tetraploid and the remaining chromosomes are triploid.

After fed-batch aerobic propagation, strain M18151 cells have high protein content relative to other strains propagated under the same conditions (Table 5). In addition, the shape of strain M18151 remained elongated, even in rich media (FIG. 3). Further, strain M18151 has poor sporulation efficiency in response to nitrogen starvation (Table 6). Strain M18151 has a low production yield after fed-batch aerobic propagation, relative to other strains (Table 7). Interestingly, strain M18151 has a complex morphology when grown on solid media (FIG. 4). Furthermore, strain M18151 has higher than diploid ploidy: most of its chromosomes appear to be triploid (present in three copies), with two tetraploid chromosomes, one of which is semi-homozygosed (FIG. 5).

TABLE 5

Comparison of protein content of strains at least
duplicate fed-batch aerobic propagations on molasses.

| Strain | Average protein content (%) |
|---|---|
| M18151 | 53.3 |
| M18152 | 43.8 |
| M18195 | 49.4 |

TABLE 6

Percentage of sporulated cells in the M2390 and the
M18151 strains after incubation on sporulation medium.

| Strain | % sporulated |
|---|---|
| M2390 | 77 |
| M18152 | 13 |

TABLE 7

Yield of various yeast strains after a least
duplicate aerobic fed-batch propagations
on molasses

| Strain | Biomass yield (relative to M18152) |
|---|---|
| M18151 | 89% |
| M18152 | 100% |
| M18195 | 85% |

Without wishing to be bound to theory, some of the M18151 strain's phenotypes could be attributed to the higher ploidy of the strain. One example is elongated cell shape; higher ploidy cells have been shown to have both an increased cell size and an increased aspect ratio. Other features of the strain seem to point to altered physiology not necessarily related to ploidy. Specifically, many of the M18151 strain phenotypes are consistent with constitutively upregulated production of cyclic AMP (cAMP), an intracellular signaling molecule central to nutrient signaling and the regulation of several metabolic systems in *Saccharomyces cerevisiae*. Modulations of the Ras/cAMP/PKA pathway result in an array of different phenotypes, including altered sporulation efficiency, pseudohyphal growth, altered stress tolerance, altered levels of the storage carbohydrates glycogen and trehalose, etc. Elevated cAMP in *S. cerevisiae* has been shown to cause complex morphology when strains are grown on solid media and low sporulation efficiency during nitrogen starvation. This condition has also been shown to decrease the production yield for a strain during growth in conditions similar to those of fed-batch propagation.

It was found that strain M18151 has a few mutations in CYR1, a gene that directly affects cAMP levels as the enzyme responsible for converting ATP to cAMP in yeast (Table 8).

TABLE 8

Mutations the CYR1 gene and protein present in the M18151 strain but not in the
M18152. NT = nucleotide (corresponding to the numbering of SEQ ID NO: 5 or 7);
AA = amino acid (corresponding to the numbering of SEQ ID NO: 6 or 8).

| CYR1 MUTANTS | | AA at position | | |
|---|---|---|---|---|
| NT position | AA position | M18151 | M18152 | Protein domain information (if any) |
| 772 | 258 | T | A | |
| 2504 | 835 | V | A | Leucine-rich repeats (LRR), to which Ras binds |
| 2605 | 869 | K | E | Leucine-rich repeats (LRR), to which Ras binds |
| 4305 | 1435 | E | D | PPM-type phosphatase region |

Elevated levels of cAMP could make a strain a good heterologous protein expression host. Increased cAMP levels have been associated with increased protein content in *S. cerevisiae*, the prevention of the downregulation of ribosome biogenesis and autophagy of cellular components, including proteins. This could lead to higher heterologous enzyme production due to increased rate of translation and a decrease in the degradation of heterologous protein via autophagy.

Increased ploidy could also benefit heterologous protein expression, because any stably engineered genetic construct, if it is present on every copy of a chromosome, will have higher copy number per cell than in a lower ploidy strain.

M18151 strain's elongated, and potentially larger, cell shape could add to the benefit of the strain as an heterologous protein expression host. Its elongated shape provides a higher surface area-to-volume ratio than a spherical shape. Greater cell surface area has been correlated with increased rate of glucose uptake in *S. cerevisiae* strains adapted to glucose-limited conditions, speculated to be due to more space in the cell membrane for the insertion of nutrient transporters. Faster nutrient uptake could quicken general cell metabolism, including heterologous protein production. A larger cell surface may also result in an increase in heterologous enzyme secretion or release during autolysis processes, since there would be more area from which protein release can occur.

While the invention has been described in connection with specific embodiments thereof, it will be understood that the scope of the claims should not be limited by the preferred embodiments set forth in the examples, but should be given the broadest interpretation consistent with the description as a whole.

What is claimed is:

1. A recombinant yeast host cell for making an increased amount of a heterologous protein, wherein the recombinant yeast host cell:
   (i) (a) has a first heterologous nucleic acid encoding the heterologous protein; and
   (b) expresses a variant CYR1 protein; and/or
   (ii) is obtained by introducing the first heterologous nucleic acid encoding the heterologous protein in an ancestral yeast host cell that expresses a variant CYR1 protein;
   wherein the variant CYR1 protein:
      provides to the recombinant yeast host cell or the ancestral yeast host cell a similar intracellular cAMP production in the presence and in the absence of a cAMP stimulus known to stimulate intracellular cAMP production in a control yeast cell, and
      comprises the amino acid sequence of SEQ ID NO: 8 with a substitution at position 258, 835, and/or 1435 or a variant thereof having 90% identity with the amino acid sequence of SEQ ID NO: 8 with a substitution at position 258, 835, and/or 1435.

2. The recombinant yeast host cell of claim 1, wherein the amount of heterologous protein per cell of the recombinant yeast host cell is increased with respect to a corresponding amount in a control yeast cell.

3. The recombinant yeast host cell of claim 1, wherein the control yeast cell corresponds to biological deposit PTA-125176 or a yeast cell having the characteristics of the biological deposit PTA-125176; the ancestral yeast host cell is biological deposit PTA-125175 or a yeast cell having the characteristics of the biological deposit PTA-125175; and/or the ancestral yeast host cell is biological deposit PTA-125177 or a yeast cell having the characteristics of the biological deposit PTA-125177.

4. The recombinant yeast host cell of claim 1, wherein the variant CYR1 protein is encoded by a variant CYR1 gene,
   the variant CYR1 gene is a native CYR1 gene in the yeast ancestral host cell, or the recombinant yeast host cell comprises a second heterologous nucleic acid molecule comprising the variant CYR1 gene.

5. The recombinant yeast host cell of claim 4, wherein the variant CYR1 gene has at least one single nucleotide polymorphism (SNP).

6. The recombinant yeast host cell of claim 5, wherein the at least one SNP comprises G772A, C2480T and/or C4305A when using the numbering of the nucleic acid sequence of SEQ ID NO: 7.

7. The recombinant yeast host cell of claim 1, wherein the variant CYR1 protein has an A258T, A835V and/or D1435E substitution when using the numbering of the amino acid sequence of SEQ ID NO: 8 or a variant thereof having 90% identity with the amino acid sequence of SEQ ID NO: 8 with a substitution at position A258T, A835V, and/or D1435E.

8. The recombinant yeast host cell of claim 1 exhibiting polyploidy in at least one chromosome.

9. The recombinant yeast host cell of claim 8, wherein polyploidy comprises triploidy in at least one first chromosome and tetraploidy in at least one second chromosome.

10. The recombinant yeast host cell of claim 1, wherein the heterologous protein is a heterologous enzyme.

11. The recombinant yeast host cell of claim 10, wherein the heterologous enzyme is at least one of a maltogenic alpha-amylase, an alpha-amylase, an oxidoreductase, a transferase, an hydrolase, a lyase, an isomerase, a phosphatase, a ligase, a glucoamylase, a fungal amylase, a phytase or a glucose oxidase.

12. The recombinant yeast host cell of claim 1 being a cell of genus *Saccharomyces* or a cell of species *Saccharomyces cerevisiae*.

13. A method of making the recombinant yeast host cell of claim 1, the method comprising:
   a) selecting an ancestral yeast host cell as defined in claim 1; and
   b) introducing a first heterologous nucleic acid molecule encoding the heterologous protein in the selected ancestral host cell to obtain the recombinant yeast host cell.

14. A process for making a yeast product, the process comprising:
   i) culturing the recombinant yeast host cell of claim 1 to obtain a cultured recombinant yeast host cell; and
   ii) formulating the cultured yeast host cell into the yeast product.

15. The process of claim 14 comprising, at step ii):
   a) lysing the cultured yeast host cell to obtain a lysed yeast product.

16. The process of claim 14, wherein the yeast product is an autolysate, a yeast cell wall, a yeast extract, or a purified heterologous protein.

17. The process of claim 16, wherein the purified heterologous protein is a heterologous enzyme.

18. The recombinant yeast host cell of claim 1, wherein the variant CYR1 protein comprises a further substitution at position 869 when using the numbering of the amino acid sequence of SEQ ID NO: 8.

19. The recombinant yeast host cell of claim 18, wherein the further substitution at position 869 is E869K.

20. The recombinant yeast host cell of claim 19, wherein the variant CYR1 protein is encoded by a variant CYR1 gene having a further single nucleotide polymorphism (SNP), wherein the further SNP is G2605A.

21. The process of claim 15 comprising, at step ii):
   b) drying the lysed yeast product to obtain a lysed and dried yeast product.

* * * * *